(12) United States Patent
Stam et al.

(10) Patent No.: US 8,859,502 B2
(45) Date of Patent: Oct. 14, 2014

(54) THERAPY FOR MLL-REARRANGED LEUKEMIA

(75) Inventors: Ronald Stam, Rhoon (NL); Dominique J. P. M. Stumpel, Rotterdam (NL)

(73) Assignee: Celgene Corporation, Summit, NJ (US)

( * ) Notice: Subject to any disclaimer, the term of this patent is extended or adjusted under 35 U.S.C. 154(b) by 143 days.

(21) Appl. No.: 13/229,581

(22) Filed: Sep. 9, 2011

(65) Prior Publication Data

US 2012/0094927 A1 Apr. 19, 2012

Related U.S. Application Data

(60) Provisional application No. 61/382,459, filed on Sep. 13, 2010.

(51) Int. Cl.
| | | |
|---|---|---|
| A61K 38/15 | (2006.01) | |
| A61K 45/06 | (2006.01) | |
| A61K 31/165 | (2006.01) | |
| A61K 31/245 | (2006.01) | |
| A61K 31/7068 | (2006.01) | |
| A61K 31/4402 | (2006.01) | |
| A61K 31/20 | (2006.01) | |
| C12Q 1/68 | (2006.01) | |
| A61K 31/167 | (2006.01) | |
| A61K 31/19 | (2006.01) | |
| G01N 33/574 | (2006.01) | |
| A61K 31/4406 | (2006.01) | |

(52) U.S. Cl.
CPC ........... *A61K 31/165* (2013.01); *A61K 31/4402* (2013.01); *A61K 31/20* (2013.01); *A61K 31/245* (2013.01); *C12Q 2600/106* (2013.01); *C12Q 2600/118* (2013.01); *C12Q 1/6886* (2013.01); *G01N 2800/52* (2013.01); *A61K 31/167* (2013.01); *A61K 31/19* (2013.01); *A61K 38/15* (2013.01); *G01N 33/57426* (2013.01); *A61K 45/06* (2013.01); *C12Q 2600/158* (2013.01); *A61K 31/4406* (2013.01); *A61K 31/7068* (2013.01); *C12Q 2600/154* (2013.01)
USPC ....... 514/19.2; 514/19.3; 514/19.6; 514/19.9; 514/43; 514/49; 514/537; 514/557; 514/575

(58) Field of Classification Search
CPC ..... A61K 38/15; A61K 45/06; A61K 31/165; A61K 31/245; A61K 31/7068; A61K 2300/00
USPC ......... 514/19.2, 19.3, 19.6, 19.9, 43, 49, 537, 514/557, 575
See application file for complete search history.

(56) References Cited

U.S. PATENT DOCUMENTS

| | | | |
|---|---|---|---|
| 4,328,235 A | 5/1982 | Yu et al. | |
| 4,409,239 A | 10/1983 | Yu et al. | |
| 4,410,545 A | 10/1983 | Yu et al. | |
| 4,977,138 A | 12/1990 | Okuhara et al. | |
| 5,510,270 A | 4/1996 | Fodor et al. | |
| 5,545,522 A | 8/1996 | Van Gelder et al. | |
| 5,556,752 A | 9/1996 | Lockhart et al. | |
| 5,578,832 A | 11/1996 | Trulson et al. | |
| 5,605,793 A | 2/1997 | Stemmer | |
| 5,716,785 A | 2/1998 | Van Gelder et al. | |
| 5,776,905 A | 7/1998 | Gibbons et al. | |
| 5,817,667 A * | 10/1998 | Chu et al. ...................... | 514/274 |
| 5,830,721 A | 11/1998 | Stemmer et al. | |
| 5,837,458 A | 11/1998 | Minshull et al. | |
| 5,891,636 A | 4/1999 | Van Gelder et al. | |
| 6,117,679 A | 9/2000 | Stemmer | |
| 6,350,458 B1 | 2/2002 | Modi et al. | |
| 6,391,640 B1 | 5/2002 | Minshull et al. | |
| 6,403,555 B1 | 6/2002 | Skov et al. | |
| 6,548,479 B1 | 4/2003 | Skov et al. | |
| 6,706,686 B2 | 3/2004 | Long et al. | |
| 6,777,217 B1 | 8/2004 | Schreiber et al. | |
| 6,809,118 B2 | 10/2004 | Chung et al. | |
| 6,828,302 B1 | 12/2004 | Skov et al. | |
| 6,905,669 B2 | 6/2005 | DiMartino | |
| 6,946,441 B2 | 9/2005 | Long et al. | |
| 7,041,639 B2 | 5/2006 | Skov et al. | |
| 7,056,883 B2 | 6/2006 | Ito et al. | |
| 7,056,884 B2 | 6/2006 | Nakajima et al. | |
| 7,148,204 B2 | 12/2006 | Bennett et al. | |

(Continued)

FOREIGN PATENT DOCUMENTS

| | | |
|---|---|---|
| CA | 2317003 | 8/2001 |
| EP | 0352646 | 1/1990 |
| EP | 1010705 | 6/2000 |
| EP | 1426054 | 6/2004 |
| JP | 7(1995)-64872 | 7/1995 |
| JP | 11-335375 | 12/1999 |
| JP | 2001-348340 | 12/2001 |
| WO | WO 98/39965 | 9/1998 |
| WO | WO 98/40080 | 9/1998 |
| WO | WO 01/18171 | 3/2001 |

(Continued)

OTHER PUBLICATIONS

Overview of Leukemia from Merck manual, pp. 1-4. Accessed Jul. 10, 2013.*
Acute Leukemia from Merck manual, pp. 1-6. Accessed Jul. 10, 2013.*
Introduction to cancer from Merck manual, p. 1. Accessed Mar. 5, 2008.*

(Continued)

*Primary Examiner* — Julie Ha
(74) *Attorney, Agent, or Firm* — Jones Day

(57) ABSTRACT

Provided are methods for treating MLL-rearranged ALL by administering to a patient an HDAC inhibitor alone or in combination with a DNA demethylating agent. Also provided are methods of treating MLL-rearranged infant ALL. Methods of treating cells by these agents are also provided. Additionally, disclosed is a method for screening for compounds capable to treat MLL-rearranged ALL, in particular, MLL-rearranged infant ALL. In one embodiment, the HDAC inhibitor is romidepsin.

11 Claims, 25 Drawing Sheets

(56) References Cited

U.S. PATENT DOCUMENTS

| | | | |
|---|---|---|---|
| 7,171,311 | B2 | 1/2007 | Dai et al. |
| 7,314,862 | B2 | 1/2008 | Naoe et al. |
| 7,354,928 | B2 | 4/2008 | Wang et al. |
| 7,396,665 | B2 | 7/2008 | Ueda et al. |
| 7,470,722 | B2 | 12/2008 | Malecha et al. |
| 7,488,712 | B2 | 2/2009 | Yoshida et al. |
| 7,857,804 | B2 | 12/2010 | McCaffrey et al. |
| 2003/0162293 | A1 | 8/2003 | Chu et al. |
| 2004/0018968 | A1 | 1/2004 | Sgouros et al. |
| 2004/0053820 | A1 | 3/2004 | Nakajima et al. |
| 2004/0072735 | A1 | 4/2004 | Richon et al. |
| 2004/0077591 | A1 | 4/2004 | Dangond |
| 2004/0127523 | A1 | 7/2004 | Bacopoupos et al. |
| 2004/0228909 | A1 | 11/2004 | Sarris et al. |
| 2005/0059682 | A1 | 3/2005 | Rubinfeld |
| 2005/0070467 | A1 | 3/2005 | Naoe et al. |
| 2005/0187148 | A1 | 8/2005 | Naoe et al. |
| 2005/0187149 | A1 | 8/2005 | Naoe et al. |
| 2005/0191713 | A1 | 9/2005 | Sasakawa et al. |
| 2005/0222013 | A1 | 10/2005 | Jung et al. |
| 2005/0272647 | A1 | 12/2005 | Yamaji et al. |
| 2006/0018921 | A1 | 1/2006 | Levenson et al. |
| 2006/0019883 | A1 | 1/2006 | Kronblad et al. |
| 2006/0100140 | A1 | 5/2006 | Dent et al. |
| 2006/0106049 | A1 | 5/2006 | Odenike |
| 2006/0128660 | A1 | 6/2006 | Rajski et al. |
| 2006/0135413 | A1 | 6/2006 | Naoe et al. |
| 2006/0223747 | A1 | 10/2006 | Ito et al. |
| 2006/0270016 | A1 | 11/2006 | Holm |
| 2007/0015787 | A1 | 1/2007 | Bruncko et al. |
| 2007/0110719 | A1 | 5/2007 | Holm |
| 2007/0129290 | A1 | 6/2007 | Or et al. |
| 2007/0148228 | A1 | 6/2007 | Cumming et al. |
| 2007/0292512 | A1 | 12/2007 | Leonard et al. |
| 2008/0214446 | A1 | 9/2008 | Okada et al. |
| 2008/0233562 | A1 | 9/2008 | Sasakawa et al. |
| 2009/0186382 | A1 | 7/2009 | Verdine et al. |
| 2009/0209616 | A1 | 8/2009 | Verdine et al. |
| 2009/0221473 | A1 | 9/2009 | Chan et al. |
| 2010/0093610 | A1* | 4/2010 | Vrolijk et al. ............... 514/9 |
| 2010/0152100 | A1* | 6/2010 | McCulloch et al. ............ 514/10 |

FOREIGN PATENT DOCUMENTS

| | | |
|---|---|---|
| WO | WO 01/42282 | 6/2001 |
| WO | WO 02/06307 | 1/2002 |
| WO | WO 02/15921 | 2/2002 |
| WO | WO 02/20817 | 3/2002 |
| WO | WO 02/86498 | 4/2002 |
| WO | WO 02/97053 | 5/2002 |
| WO | WO 02/055017 | 7/2002 |
| WO | WO 02/055688 | 7/2002 |
| WO | WO 02/085400 | 10/2002 |
| WO | WO 02/090534 | 11/2002 |
| WO | WO 03/015810 | 2/2003 |
| WO | WO 03/017763 | 3/2003 |
| WO | WO 03/024442 | 3/2003 |
| WO | WO 03/035843 | 5/2003 |
| WO | WO 03/053468 | 7/2003 |
| WO | WO 03/070188 | 8/2003 |
| WO | WO 03/083067 | 10/2003 |
| WO | WO 03/084611 | 10/2003 |
| WO | WO 03/088954 | 10/2003 |
| WO | WO 03/103613 | 12/2003 |
| WO | WO 2004/009771 | 1/2004 |
| WO | WO 2004/017996 | 3/2004 |
| WO | WO 2004/024160 | 3/2004 |
| WO | WO 2004/062654 | 7/2004 |
| WO | WO 2004/064727 | 8/2004 |
| WO | WO 2004/074478 | 9/2004 |
| WO | WO 2004/096289 | 11/2004 |
| WO | WO 2004/098495 | 11/2004 |
| WO | WO 2005/000282 | 1/2005 |
| WO | WO 2005/000289 | 1/2005 |
| WO | WO 2005/000332 | 1/2005 |
| WO | WO 2005/009961 | 2/2005 |
| WO | WO 2005/018578 | 3/2005 |
| WO | WO 2005/023179 | 3/2005 |
| WO | WO 2005/027842 | 3/2005 |
| WO | WO 2005/030239 | 4/2005 |
| WO | WO 2005/039498 | 5/2005 |
| WO | WO 2005/051430 | 6/2005 |
| WO | WO 2005/052143 | 6/2005 |
| WO | WO 2005/053609 | 6/2005 |
| WO | WO 2005/058298 | 6/2005 |
| WO | WO 2005/079827 | 9/2005 |
| WO | WO 2005/085864 | 9/2005 |
| WO | WO 2005/087206 | 9/2005 |
| WO | WO 2005/105055 | 11/2005 |
| WO | WO 2005/105066 | 11/2005 |
| WO | WO 2005/115149 | 12/2005 |
| WO | WO 2005/117930 | 12/2005 |
| WO | WO 2006/027346 | 3/2006 |
| WO | WO 2006/055621 | 5/2006 |
| WO | WO 2006/060382 | 6/2006 |
| WO | WO 2006/060429 | 6/2006 |
| WO | WO 2006/129105 | 12/2006 |
| WO | WO 2007/009539 | 1/2007 |
| WO | WO 2007/040522 | 4/2007 ............. A61K 38/12 |
| WO | WO 2007/058896 | 5/2007 |
| WO | WO 2007/061939 | 5/2007 |
| WO | WO 2007/145704 | 12/2007 |
| WO | WO 2007/146730 | 12/2007 |
| WO | WO 2008/013589 | 1/2008 |
| WO | WO 2009/064300 | * 5/2009 ............. A61K 31/19 |

OTHER PUBLICATIONS

Clinical Aspects of cancer from Merck manual, pp. 1-4. Accessed Mar. 5, 2008.*

Auerbach R, Akhtar N, Lewis RL, Shinners BL, "Angiogenesis assays: Problems and pitfalls," Cancer and Metastasis Reviews, 2000, 19: 167-172.*

Jain RK, "Barriers to drug delivery in solid tumors," Scientific American, Jul. 1994, pp. 58-65.*

Gura T, "Systems for identifying new drugs are often faulty," Science, 1997, 278: 1041-1042.*

Romaza: Phase I study of romidepsin and azacitidine in acute myeloid leukaemia patients, from www.nhs.uk/Conditions/Leukaemia-acute/Pages/clinical-trials-details.aspx?TrialId=IS, pp. 1-2. Accessed May 5, 2014.*

Armstrong et al., "MLL translocations specify a distinct gene expression profile that distinguishes a unique leukemia," Nat Genet 30(1):41-47 (2002).

Aron et al., "Depsipeptide (FR901228) induces histone acetylation and inhibition of histone deacetylase in chronic lymphocytic leukemia cells concurrent with activation of caspase 8-mediated apoptosis and down-regulation of c-Flip protein," Blood, 102(2):652-658 (2003).

Baylin et al., "Alternations in DNA Methylation: A Fundamental Aspect of Neoplasia," Adv. Cancer Res, 72:141-96 (1998).

Bates et al., "Final Clinical Results of a Phase 2 NCI Multicenter Study of romidepsin In Recurrent Cutaneous T-Cell Lymphoma (Molecular Analyses Included)," ASH Annual Meeting Abstracts, 112(11): p. 1568 (2008).

Bennjamini, "Controlling the False Discovery Rate: a Practical and Powerful Approach to Multiple Testing," J Roy Stat Soc B, 57(1):289-300 (1995).

Berge et al., "Pharmaceutical Salts," J Pharm Science 66:1-19, 1977.

Bhalla, "Epigenetic and chromatin modicifers as targeted therapy of hematologic malignancies," J Clin Oncol, 23(17):3971-3993 (2005).

Bishton et al., "Epigenetic target in hematological malignancies: combination therapies with HDAC's and demethylating agents," Expert Rev Anticancer Ther, 7(10):1439-1449 (2007).

Blyth et al., "The Runx Genes: Gain or Loss of Function in Cancer," Nat Rev Cancer, 5(5):376-387 (2005).

Bogden et al., "Growth of Human Tumor Xenografts Implanted under the Renal Capsule of Normal Immunocompetent Mice," Exp Cell Biol 47:281-293 (1979).

(56) References Cited

OTHER PUBLICATIONS

Bolden et al., "Anticancer activities of histone deacetylase inhibitors," Nat Rev Drug Discovery, 5(9):769-784 (2006).
Budillon et al., "Growth arrest, apoptosis and potentiation of 5-fluorouracil and Raltitrexed cytotoxic effect induced by histone deacetylase inhibitor SAHA in colorectal cancer cells," Eur J Cancer 38:S29 (2002).
Butler et al., "Suberoylanilide Hydroxamic Acid, an Inhibitor of Histone Deacetylase, Suppresses the Growth of Prostate Cancer Cells in Vitro and in Vivo," Cancer Res 60:5165-5170 (2000).
Byrd et al., "A phase 1 and pharmacodynamic study of depsipeptide (FK228) In chronic lymphocytic leukemia and acute myeloid leukemia,"Blood, 105(3):959-967 (2005).
Byrd et al., "Depsipeptide (FR901228): a novel therapeutic agent with Selective in vitro activity against human B-cell chronic lymphocytic leukemia cells," Blood, 94(4):1401-1408 (1999).
Catley et al., "Aggresome induction by proteasome inhibitor bortezpmib and {alpha}-tubulin hyperacetylation by tubulin deacetylase (TDAC) inhibitor LBH589 are synergistic in myeloma cells," Blood 108(10):3441-3449 (2006).
Cervoni et al., "the Oncoprotein Set/TAF-1β, an Inhibitor of Histone Acetyltransferase, Inhibits Active Demthylation of DNA, Integrating DNA Methylation and Transcriptional Silencing," J Biol Chem. 277(28):25026-25031 (2002).
Chan et al., "Depsipeptide (FR901228, NSC-630176) pharmacokinetics in the rat by LC/MS/MS," Invest New Drugs, 15(3):195-206 (1997).
Chen et al. "DNA hypomethylation leads to elevated mutation rates," Nature. 395(6697):89-93 (1998).
Chen et al., "Runxl is required for the endothelial to haematopoietic cell transition but not thereafter," Nature, 457(7231):887-891 (2009).
Cheson et al., "New Drugs for the Treatment of Chronic Lymphocytic Leukemia," Reviews Clin Exp Hematol 4(2):145-166 (2000).
Conway et al., "Vincristine-and Cisplatin-induced Apoptosis in Human Retinoblastoma. Potentiation by Sodium Butyrate," Eur J Cancer, 34(11):1741-1748 (1998).
Dai et al., "Interactions between bortezomib and romidepsin and belinostat in chronic lymphocytic leukemia cells," Clin Cancer Res, 14(2):549-558 (2008).
Database Biosis 'Online, AN-PREV200400024248, XP-002342749, "Anti-Tumor Efficacy of Four Different Histone Deacetylase Inhibitors on Hepatoma Cells in Vitro", 2003 (Abstract No. T1786).
Dennis et al., "David: Database for Annotation, Visualization, and Integrated Discovery," Genome Biol 4(5):P3 (2003).
De Ryckere et al., "Pre-clinical development of syberoylanilide hydroxamic acid for the treatment of pediatric acute leukemias," Blood, 108(11):645A (2006).
Dokmanovic & Marks, "Prospects: histone deacetylase inhibitors," J Cell Biochem, 96(2):293-304 (2005).
Edgar et al., "Gene Expression Omnibus: NCBI gene expression hybridization array data repository," Nucleic Acids Res, 30(1):207-210 (2002).
Fiebig et al., "Bcl-XL is qualitatively different from and ten times more effective than Bcl-2 when expressed in a breast cancer cell line," Cancer, 6:213 (2006).
Findley et al., "Expression and Regulation of Bcl-2, Bcl-xl, and Bax Correlate With p53 Status and Sensitivity to Apoptosis in Childhood Acute Lymphoblastic Leukemia," Blood, 89(8): 2986-2993 (1997).
Finnin et al., "Structures of a histone deacetylase homologue bound to the TSA and SAHA Inhibitors," Nature, 401(6749):188-193 (1999).
Fischer et al., 41$^{st}$ Annual Meeting of the American Society of Clinical Oncology, Abstr # 3106 (2005).
Fukumura et al., "A sensitive transcriptome analysis method that can detect unknown transcripts," Nuel Acids Res 31(16):e94 (2003).
Furumai et al.,"FK228 (depsipeptide) as a natural prodrug that inhibits class I histone deacetylases," Cancer Res, 62(17):4916-4921 (2002).

Garcia-Manero et al., "Phase 1/2study of the combination of 5-aza-2'-deoxycytidine with valporic acid inpatients with leukemia," Blood, 108(10):3271-3279 (2006).
Geldof et al., "Cytotoxicity and neurocytoxicity of new marine anticancer agents evaluacated using in vitro assays," Cancer Chemother & Pharmacol 44(4):312-318 (1999).
Glaser et al., "HDAC inhibitors: Clinical update and mechanism-based potential," Biochemical Pharmacology. 74(5):659-671 (2007).
Gore et al., "Combined DNA methyltransferase and histone deacetylase inhibition in the treatment of myeloid neoplasms," Cancer Res. 66(12):6361-6369 (2006).
Gore et al., "Impact of the putative differentiating agent sodium phenylbutyrate on myelodysplastic syndromes and acute myeloid leukemia," Clin Cancer Res, 7(8):2330-2339 (2001).
Guenther et al., "Aberrant chromatin at genes encoding stem cell regulators in human mixed-lineage leukemia," Genes Dev, 22(24):3403-3408 (2008).
Han et al., "Apicidin, a Histone Deacetylase Inhibitor Inhibits Proliferation of Tumor Cells via Induction of p21 WAF1/Cip1 and Gelsolin," Cancer Res 60(21):6068-6074 (2000).
Harrison et al., "High Response Rates with the Combination of Bortezomib, Dexamethasone and the Pan-Histone Deacetylase Inhibitor Romidepsin In Patients with Relapsed or Refractory Multiple Myeloma in Phase I/II Clinical Trial," ASH Annual Meeting Abstracts. 112(11):3698 (2008).
Huang et al., "Systematic and integrative analysis of large gene lists using DAVID bioinformatics resources," Nat Protoc, 4(1):44-57 (2009).
Inoue et al., "Subrenal capsule assay-an experimental study and clinical application to chemosensitivity tests," Gan to Kagaku Ryoho 14(5Pt2):1629-1635 (1987) (Abstract).
Jones & Baylin. "The Epigenomics of Cancer," Cell 128:683-692 (2007).
Jones & Baylin, "The fundamental role of epigenetic events in Cancer," Nat Rev Genet, 3(6):415-428 (2002).
Jung et al., "Amide Analogues of Trichostatin A as Inhibitors of Histone Deacetylase and Inducers of Terminal Cell Differentiation," J Med Chem US 42(22):4669-4679 (1999).
Kahn et al., "Total Synthesis of the Antitumor Depsipeptide FR-901. 228," J Am Chem Soc 118:7237-7238, (1996).
Kano et al., "The Joint Meeting of the 64$^{th}$ Annual Meeting of the Japanese Society of Hematology and the 44$^{th}$ Annual Meeting of the Japanese Society of Clinical Hematology," Japanese J Clin Hematology 43(8):116 (2002).
Kano et al., "Cytotoxic effects of histone deacetylase inhibitor FK228 in combination with conventional anti-leukemia/lymphoma agents against human leukemia/lymphoma cell lines," The Journal of New Anticancer Agents, 25(1):31-40 (2006).
Kawamoto et al., "Expression Profiling by iAFLP: A PCR-Based Method for Genome-Wide Gene Expression Profiling," Genome Res 12:1305-1312 (1999).
Khan et al., "Analysis of histone deacetylase inhibitor, depsipeptide (FR901228), effect on multiple myeloma," Br J Haematol, 125(2):156-161 (2004).
Kim et al., "Clinically significant responses Achieved with Romidepsin in Treatment-Refractory Cutaneous T-Cell Lymphoma: Final Results from a Phase 2B. International, Multicenter. Registration Study," ASH Annual Meeting Abstracts, 112(11):263 (2008).
Kisselev & Goldberg, "Proteasome inhibitors: from research tools to drug candidates," Chem Biol 8:739-758 (2001).
Kitazono et al., "Enhanced Adenovirus Transgene Expression in Malignant Cells Treated with the Histone Deacetylase Inhibitor FR901228," Cancer Res 61:6328-6330 (2001).
Kitazono et al., "Adenovirus HSV-TK Construct with Thyroid-Specific Promoter: Enhancement of Activity and Specificity with Histone Deacetylase Inhibitors and Agents Modulating the Camp Pathway," Int J Cancer 99:453-459 (2002).
Kitazono et al., "Low Concentrations of the Histone Deacetylase Inhibitor, Depsipeptide (FR901228), Increase Expression of the Na/I Symporter and Iodine Accumulation in Poorly Differentiated Thyroid Carcinoma Cells," J Clin Endocrin 86(7):3430-3435 (2001).
Kitazono et al., Proc Amer Assoc Cancer Res Annual 43:799 (2002) (Abstract only).

(56) References Cited

OTHER PUBLICATIONS

Klimek et al., "Tolerability, pharmacodynamics, and pharmacokinetics studies fo depsipeptide (romidepsin) in patients with acute myelogenous leukemia or advanced myelodysplastic syndromes," Clin Cancer Res. 14(3):826-832 (2008).
Klisovic et al., "Depsipeptide (FR9801228) Inhibits Proliferation and Induces Apoptosis in Primary and metastatic Human Uveal Melanoma Cell Lines," Invest Ophthalmol Vis Sci, 44(6):2390-2398 (2003).
Komatsu et al., "Cyclic Cyfroxamic-acid-containing Peptide 31, a Potent Syntheic Histone Deacetylase Inhibitor with Antitumor Activity," Cancer Res 61(11):4459-4466 (2001).
Kosaka, "Infant acute lymphoblastic leukemia with MLL gene rearrangements: outcome following intensive chemotherapy and hematopoietic stem cell transplantation," Blood, 104(12):3527-3534 (2004).
Kosugi et al., "In vivo Effects of a Histone Deacetylase Inhibitor, FK228, on Human Acute Promyelocytic Leukemia in NOD/Shi-scid/ scid Mice," Japanese J Cancer Res 92(5):529-536 (2001).
Krivtsov et al., "H3K79 Methylation Profiles Define Murine and Human MLL AF4 Leukemias," Cancer Cell 14(5):355-368 (2008).
Krivtsov et al., "MLL translocations, histone modifications and leukaemia stem cell development," Nat Rev Cancer 7(11):823-833 (2007).
Kuendgen et al., "Treatment of myelodysplastic syndromes with valproic acid alone or in combination with all-trans retinoic acid," Blood, 104(5):1266-1269 (2004).
Lamb et al., "The Connectivity Map: Using Gene-Expression Signatures to Connect Small Molecules, Genes, and Disease," Science, 313(5795):1929-1935 (2006).
Lamb, "The Connectivity Map: a new tool for biomedical research," Nat Rev Cancer, 7(1):54-60 (2007).
Lee-Sherick et al., "Targeting Pediatric Acute Lymphoblastic Leukemia: novel therapies currently in development," British Journal of Hematology, 151(4):295 (2010).
Liakopoulou et al., "Stimulation of Fetal Hemoglobin Production by Short Chain Fatty Acids," Blood, 86:3227 (1995).
Lotfi et al., "AT9283, A Novel Aurora Kinase/Jak2 Inhibitor Demonstrates Activity against Refractory Infant Leukemia Cells: Studies on Growth Inhibition, Biological Correlates, Drug Synergy and Effects on Leukemia Stem-Like Cells," Blood, 114(22):1197 (2009).
Maeda et al., "Up-regulation of costimulatory/adhesion molecules by histone deacefylase ihibitors in acute myeloid leukemia cells," Blood, 96(12):3847-3856 (2000).
Magner et al.. "Activation of MHC class I, II, and CD40 gene expression by histone deacetylose inhibitors," J Immunol, 165(12):7017-7024 (2000).
Marks et al., "Histone deacetylase inhibitors: Inducers of differentiation or apoptosis of transformed cells," J Natl Cancer Inst, 92(15):1210-1216 (2000).
Marshall et at., "A phase I trial of depsipeptide (FR901228) in patients with advanced cancer," J Exp Ther Oncol, 2(6):325-332 (2002).
Mertins et al., Proc Amer Assoc Cancer Res Annual Meetins 40:623 (1999).
Meyer et al., "Reflecting on 25 years with MYC," Nat Rev Cancer, 8(12):976-990 (2008).
Mitsiades et al., "Transcriptional signature of histone deacetylase inhibition in multiple myeloma: biological and clinical implications," Proc Natl Acad Sci USA, 101(2):540-545 (2004).
Molife et al.," Phase II study of FK228 in patients with hormone refractory prostate cancer (HRPC)," J Clin Oncol (Meeting Abstracts), 24(18 Suppl):14554 (2006).
Murata et al., "Apoptotic Cytotoxic Effects of a Histone Deacetylase Inhibitor, FK228, on Malignant Lymphoid Cells," Japanese J Cancer Res 91:1154-1160 (2000).
Nakajima et al., "FR901228, a potent antitumor antibiotic, is a novel histone deticetylose inhibitor," Exp Cell Res, 241(1)126-133 (1998).
Nakayama et al., "GSTP1 CpG Island Hypermethylation as a Molecular Biomarker for Prostate Cancer," J Cell Biochem, 91(3):540-552 (2004).
Nebbioso et al., "Tumor-selective action of HDAC inhibitors involves TRAIL induction in acute myeloid leukemia cells," Nat Med, 11(1):77-84 (2005).
Nebozhyn et at., "Quantitative PCR on 5 genes reliably Identifies CTCL patients with 5% to 99% circulating tumor cells with 90% accuracy," Blood, 107(8):3189-3196 (2006).
Newbold et al., "Characterisation of the novel apoptotic and therapeutic activities of the histone deacetylase inhibitor romidepsin," Mol Cancer Ther, 7(5):1066-1079 (2008).
Niesvizky et al., "Multicenter Phase II Trial of the Histone Deacetylase Inhibitor Depsipeptide (FK228) for the Treatment of Relapsed or Refractory Multiple Myeloma (MM)," Blood ASH Annual Meeting Abstracts, 106(11):2574 (2005).
Nishimura et al., "A New Antitumor Antibiotic, FE900840," J Antibiot XLII(4):553-557 (1989).
Nuijen et al., "Development of a lyophilized parenteral pharmaceutical formulation the investicational polypeptide marine anticancer agent kahalalide F.," Medline (2001) XP-002206588.
Odenike et al., "Histone deacetylase inhibitor romidepsin has differential activity in core binding factor acute myeloid leukemia," Cancer Res, 14(21):7095-7101 (2008).
Paoluzzi et al., "Romidepsin and belinos at synergize the antineoplastic effect of bortezomib in mantle cell lymphoma," Clin Cancer Res, 16(2):554-565 (2010).
Peart et al., "Novel mechanisms of apoptosis induced by histone deacetylase inhibitors," Cancer Res, 63(15):4460-4471 (2003).
Peart et al., "Identification and functional significance of genes regulated by structurally different histone deacetylose inhibitors," Proc Natl Acad Sci USA, 102(10):3697-3702 (2005).
Pei et al., "Synergistic induction of oxidative injury and apoptosis in human multiple myeloma cells by the proteasome inhibitor bortezpmib and histone deacetylase inhibitors," Clin Cancer Res, 10(11):3839-3852 (2004).
Piekarz et al., "Completion of the First Cohort of Patients with Cutaneous T-Cell Lymphoma Enrolled on a Phase II Trial of Depsipeptide," ASH Annual Meeting Abstracts, 106(11):231 (2005).
Piekarz et at., "Results of a Phase 2 NCI Multicenter Study of Romidepsin in Patients with Relapsed Peripheral T-Cell Lymphoma (PTCL)," ASH Annual Meeting Abstracts 112(11):1567 (2008).
Piekarz et al., "T-cell lymphoma as a model for the use of histone deacetylase inhibitors in cancer therapy: impact of depsipeptide on molecular markers, therapeutic targes, and mechanisms of resistance," Blood, 103(12):4636-4643 (2004).
Piekarz et al., "Inhibitor of histone deactylation, depsipeptide (FR901228), in the treatment of peripheral and cutaneous T-cell lymphoma: a case report," Blood, 98(9):2865-2868 (2001).
Piekarz et al., "Cardiac studies In patients treated with depsipeptide, FK228, In a phase II trial for T-cell lymphoma," Clin Cancer Res, 12(12):3762-3773 (2006).
Piekarz et al., "Epigenetic modifiers: basic understanding and clinical development," Clin Cancer Res, 15(12):3918-3926 (2009).
Piekarz et al., "Phase II Multi-Institutional Trial of the Histone Deacetylase Inhibitor Romidepsin As Monotherapy for Patients With Cutaneous T-Cell Lymphoma," J Clin Oncol, 27(32):5410-5417 (2009).
Piekarz et al., "A Review of Depsipeptide and Other Histone Deacetylase Inhibitors in Clinical Trials," Curr Pharm Des 10:2289-2298 (2004).
Piekarz, R., et al, "Update of the NCI multiinstutional phase II trial of romidepsin. FK228, for patients with cutaneous or peripheral T-cell lymphoma," J Clio Oncol (Meeting Abstracts), 2007.25(18_suppl): p. 8027 (2007).
Pieters et al., "A treatment protocol for infants younger than 1 year with acute lymphoblastic leukaemia (Interfant-99): an observational study and a multicentre randomised trial," Lancet, 70(9583):240-250 (2007).
Pocock et al., "BCL-2 expression by leukaemic blasts in a SCID mouse model of biphenotypic leultaemia associated with the t(4;11)(q21;q23) translocation," Br J Haematol, 90(4):855-867 (1995).

(56) References Cited

OTHER PUBLICATIONS

Prince et al., "Clinical studies of histone deacetylase inhibitors," Clin Cancer Res, 15(12):3958-3969 (2009).
Program of the 4th Japanese Foundation for Cancer Research, International Symposium on Cancer Therapy (ISCC), Feb. 12, 1999.
Pui et al., "Acute lymphoblastic leukaemia," Lancet, 371(9617):1030-1043 (2008).
Rasheed et al., "Histone deacetylase inhibitors in cancer therapy," Expert Opin Investig Drugs, 16(5):659-678 (2007).
Reich et al., "GenePattern 2.0," Nat Genet, 38(5):500-501 (2006).
Rensen et al., "The GTPase Ran: regulation of cell life and potential roles in cell transformation," Front Biosci 13:4097-4121 (2008).
Richon et al., "Histone Deacetylase Inhibitors: A New Class of Potential Therapeutic Agents for Cancer Treatment," Clin Cancer Res 8(3):662-664 (2002).
Richon et al., "Histone deacetylasei inhibitor selectively induces p21 WAFI expression and gene-associated histone acetylation," Proc Natl Acad Sci USA, 97(18):10014-10019 (2000).
Robey et al., "Increased MDRI expression in normal and malignant peripheral blood mononuclear cells obtained from patients receiving depsipetide (FR901228, FK228, NSC630176)," Clin Cancer Res, 12(5):1547-1555 (2006).
Robinson et al., "Amplification of AML1 in acute lymphoblastic leukemia is associated with a poor Outcome," Leukemia, 17(11):2249-2250 (2003).
Roychowdhury et al., "Selective efficacy of depsipeptide in a xenograft model of Epstein-Barr virus-positive lymphoproliferative disorder," J Natl Cancer Inst, 96(19):1447-1457 (2004).
Sakai et al., "MBD3 and HDACI, two components of the NuRDcomplex, are localized at Aurora-A-positive centrosomes in M phase," J Biol Chem, 277(50):48714-48723 (2002).
Sandor et al., "P21-dependent G arrent with downregulation of cyclin D1 upregulation of cyclin E by the histone deacetylase inhibitor FR901228," Br J Cancer 83(6):817-825, (2000).
Sandor et al., "Phase I trial of the histone deacetylase Inhibitor, depsipeptide (FR901228, NSC 630176), In patients with refractory neoplasms," Clin Cancer Res, 8(3):718-728 (2002).
Sarmento-Ribeiro et al., "Epigenetic Modulation—A New Therapeutic Approach to Lymphoid Malignancies," The Hematology Journal, 93(1):538 (2008).
Sasakawa et al., "Effects of FK228, a novel histone deacetylase inhibitor, on human lymphoma U-937 cells in vitro and in vivo," B Pharmacol, 64(7):1079-1090 (2002).
Sawa et al., "Histone deacetylase Inhibitor, FK228, Induces apoptosis and suppresses cell roliferation of human glioblastoma cells In vitro and In vivo," Acta Neuropathol (Berlin), 07(6):523-531 (2004).
Sawa et al., "Anti-tumor effects of Hitone deacetylase inhibitors against human glioma cells," Proc of Japanese Cancer Assoc 60:597 (2001) (w/English translation).
Schrump et al., "Clinical and molecular responses in lung cancer patients receiving romidepsin," Clin Cancer Res, 14(1):188-198 (2008).
Schwartsmann et al., "Marine organisms as a source of new anticancer agents," The Lancet Oncology 2(4):221-225 (2001).
Shimoyama et al., "Synergistic action of MLL, a TRX protein with template activating factor-I, a histone chaperone," FEBS LETT, 579(3):757-752 (2005).
Silverman et al., "P131 Phase I trial of the combination of the epigenetic modulator vorinostat and azacitidine in patients with the myelodysplastic syndrome and acute myeloid leukemia. An update from the NY Cancer Consortium," Leukemia Research, 33:S135-S136 (2009).
Sreedharan et al., "Relevance of circadian closing time for the tolerability of germcitabine as a single agent of combined with cisplatin in mice," Proc Amer Assoc Cancer Res 44(2 ed.):742 (2003) (XP-001154773).
Stadler et al., "A phase II study of depsipeptide in refractory metastatic renal cell cancer" Clin Genitourin Cancer, 5(1):57-60 (2006).
Stam et al., "Targeting FLT3 in primary MLL gene-rearranged infant acute lymphoblastic leukemia," Blood, 106(7):2484-2490 (2005).

Stam et al., "D-HPLC analysis of the entire FLT3 gene in MLL rearranged and hyperdiploid acute lymphoblastic leukemia," Haematologica, 92(11):1565-1568 (2007).
Stam et al., "Gene expression profiling-based dissection of MLL-translocated and MLL germline acute lymphoblastic leukemia in infants," Blood, 115(14):2835-2844 (2010).
Strong et al., "Strong Acute Leukemia Cell Line With the t(4;11) Chromosomal Rearrangement Exhibits B Lineage and Monocytic Characteristics," Blood, 65(1):21-31 (1985).
Stumpel et al., "Specific promoter methylation identifies different subgroups of MLL-rearranged infant acute lymphoblastic leukemia, influences clinical outcome, and provides therapeutic options," Blood, 114(27):5490-5498 (2009).
Su et al., "A phase II study of single agent depsipeptide (DEP) in patients (pts) with radioactive iodine (RAI)-refractory, metastatic, thyroid carcinoma: Preliminary toxicity and efficacy experience," J Clin Oncol (Meeting Abstracts), 24(18 Suppl):5554 (2006).
Sutheesophon et al., "Histone deacetylase inhibitor depsipeptide (FK228) induces apoptosis in leukemic cells by facilitating mitochondrial translocation of Bax, which is enhanced by the proteasome Inhibitor bonezpmib," Acta Haematol, 115(1-2):78-90 (2006).
Ueda et al., "Action of FR901228, a novel antitumor bicyclic depsipeptide produced by Chromobacterium violaceum No. 968, on Ha-ras transformed NIH3T3 cells," Biosci Biotechnol Biochem, 58(9):1579-1583 (1994).
Ueda et al., "FR901228, a novel antitumor bicyclic depsipeptide produced by Chromobacterium violaceum No. 968. I. Taxonomy, fermentation, isolation, physico-chemical and biological properties, and antitumor activity," J Antibiot (Tokyo), 47:301-310, (1994).
Ueda et al., "FR901228, A Novel Antitumor Bicyclic Depsipeptide Produced by Chromobacterium violaceum No. 968," J Antibiot (Tokyo) 47:315-323 (1994).
Ueda et al., "Expression of a full-length cDNA for the human "MDR1" gene confers resistance to colchicines, doxorubicin, and vinblastine," PNAS USA 84:3004 (1987).
Villar-Garea et al., "Procaine Is a DNA-demethylating Agent with Growth-inhibitory Effects in Human Cancer Cells," Cancer Research, 63 (16):4984-4989 (2003).
Vrana et al., "Induction of apoptosis in U937 human leukemia cells by suberoylanilide hydroxamic acid (SAHA) proceeds through pathways that are regulated by Bcl-2/Bcl-XL, c-Jun, and p21CIPI, but independent of p53," Oncogene, 18(50):7016-7025 (1999).
Wang et al., "Fungal metabolite FR901228 inhibits c-Myc Fas ligand expression," Oncogene 17:1503-1508 (1998).
Watanabe et al., "Induction of autophagy in malignant rhabdoid tumor cells by the histone deacetylase inhibitor FK228 through AIF translocation," Int J Cancer,124(1):55-67 (2009).
Weidle et al. "Inhibition of Histone Deacetylases: a New Strategy to Target Epigenetic Modifications for Anticancer Treatment," Anticancer Res 20:1471-1486 (2000).
Weinberg et al., "Cooperation between Cellular Oncogenes in the Transformation of Primary Rat Embryo Fibroblasts," Prog Med Virol, 32:115-128 (1985).
Whitehead et al., "Phase II trial of depsipeptide (NSC-630176) in colorectal cancer patients who have received either one or two prior chemotherapy regimens for nwrARrux or locally advanced, unresectable disease: A Southwest Oncology Group study," J Clin Oncol (Meeting Abstracts), 24(18 Suppl):3598 (2006).
Whittaker et al., "International multicenter phaSe II study of the HDAC inhibitor (HDAC) depsipeptide (FK228) in cutaneous T-cell lymphoma (CTCL): Interim report," J Clin Oncol (Meeting Abstracts), 24(18 Suppl):3063 (2006).
Xiao et al., "Identification of thiols and glutathione conjugates of depsipeptide FK228 (FR901228), a novel hostone protein deacetylase inhibitor, in the blood," Rapid Commun Mass Spectrom 17:757-766 (2003).
Xiao et al., "Efflux of Depsipeptide FK228(FR901228, NSC-630176) Is Mediated by P-Glycoprotein and Multidrug Resistance-Associate Protein 1," J Pharm & Exp Therapeutics 313(1):268-276 (2005).
Yu et al., "The proteasome inhibitor bortezpmib interacts synergistically with histone deacetylase inhibitors to induce apoptosis in Bcr/Abl+ cells sensitive and resistant to STI571," Blood, 102(10):3765-3774 (2003).

* cited by examiner

SEQUENCE LISTING

<160> NUMBER OF SEQ ID NOS: 20

<210> SEQ ID NO 1
<211> LENGTH: 18
<212> TYPE: DNA
<213> ORGANISM: Artificial Sequence
<220> FEATURE:
<223> OTHER INFORMATION: Forward DIAPH1 primer

<400> SEQUENCE: 1
atcccacagc acagtcat                                                 18

<210> SEQ ID NO 2
<211> LENGTH: 19
<212> TYPE: DNA
<213> ORGANISM: Artificial Sequence
<220> FEATURE:
<223> OTHER INFORMATION: Reverse DIAPH1 primer

<400> SEQUENCE: 2
gggttgttgt tgagagaca                                                19

<210> SEQ ID NO 3
<211> LENGTH: 19
<212> TYPE: DNA
<213> ORGANISM: Artificial Sequence
<220> FEATURE:
<223> OTHER INFORMATION: Forward SFM8T1 primer

```
<400> SEQUENCE: 3
gagctgcctc aatgtgtag                                                 19

<210> SEQ ID NO 4
<211> LENGTH: 21
<212> TYPE: DNA
<213> ORGANISM: Artificial Sequence
<220> FEATURE:
<223> OTHER INFORMATION: Reverse SFM8T1 primer

<400> SEQUENCE: 4
gacagcattc cagtttgata c                                              21

<210> SEQ ID NO 5
<211> LENGTH: 20
<212> TYPE: DNA
<213> ORGANISM: Artificial Sequence
<220> FEATURE:
<223> OTHER INFORMATION: Forward RAN primer

<400> SEQUENCE: 5
tggcaacaaa gtggatatta                                                20

<210> SEQ ID NO 6
<211> LENGTH: 17
<212> TYPE: DNA
<213> ORGANISM: Artificial Sequence
<220> FEATURE:
<223> OTHER INFORMATION: Reverse RAN primer

<400> SEQUENCE: 6
cgggagagca gttgtct                                                   17

<210> SEQ ID NO 7
<211> LENGTH: 21
<212> TYPE: DNA
<213> ORGANISM: Artificial Sequence
<220> FEATURE:
<223> OTHER INFORMATION: Forward PARK7 primer

<400> SEQUENCE: 7
gttcgctcta aacaaaacag t                                              21

<210> SEQ ID NO 8
<211> LENGTH: 21
<212> TYPE: DNA
<213> ORGANISM: Artificial Sequence
<220> FEATURE:
<223> OTHER INFORMATION: Reverse PARK7 primer

<400> SEQUENCE: 8
taggctgaga aatctctgtg t                                              21

<210> SEQ ID NO 9
<211> LENGTH: 19
<212> TYPE: DNA
<213> ORGANISM: Artificial Sequence
<220> FEATURE:
<223> OTHER INFORMATION: Forward HOXA9'9 primer

<400> SEQUENCE: 9
cacgcttgac actcacact                                                 19
```

```
<210> SEQ ID NO 10
<211> LENGTH: 19
<212> TYPE: DNA
<213> ORGANISM: Artificial Sequence
<220> FEATURE:
<223> OTHER INFORMATION: Reverse HOXA9'9 primer

<400> SEQUENCE: 10
cagggtctgg tgttttgta                                              19

<210> SEQ ID NO 11
<211> LENGTH: 15
<212> TYPE: DNA
<213> ORGANISM: Artificial Sequence
<220> FEATURE:
<223> OTHER INFORMATION: Forward MYC primer

<400> SEQUENCE: 11
cgtcctcgga ttctc                                                  15

<210> SEQ ID NO 12
<211> LENGTH: 17
<212> TYPE: DNA
<213> ORGANISM: Artificial Sequence
<220> FEATURE:
<223> OTHER INFORMATION: Reverse MYC primer

<400> SEQUENCE: 12
gctgcgtagt tgtgctg                                                17

<210> SEQ ID NO 13
<211> LENGTH: 18
<212> TYPE: DNA
<213> ORGANISM: Artificial Sequence
<220> FEATURE:
<223> OTHER INFORMATION: Forward SEro primer

<400> SEQUENCE: 13
ttcccgatat ggatgatg                                               18

<210> SEQ ID NO 14
<211> LENGTH: 18
<212> TYPE: DNA
<213> ORGANISM: Artificial Sequence
<220> FEATURE:
<223> OTHER INFORMATION: Reverse SEro primer

<400> SEQUENCE: 14 cccccaaat aaattgag                                                18

<210> SEQ ID NO 15
<211> LENGTH: 16
<212> TYPE: DNA
<213> ORGANISM: Artificial Sequence
<220> FEATURE:
<223> OTHER INFORMATION: Forward RUNX1 primer

<400> SEQUENCE: 15
gacagcccca ccttcc                                                 16

<210> SEQ ID NO 16
<211> LENGTH: 16
<212> TYPE: DNA
<213> ORGANISM: Artificial Sequence
<220> FEATURE:
<223> OTHER INFORMATION: Reverse RUNX1 primer
```

```
-continued

<400> SEQUENCE: 16
ccacttcgac cgacaa                                                         16

<210> SEQ ID NO 17
<211> LENGTH: 16
<212> TYPE: DNA
<213> ORGANISM: Artificial Sequence
<220> FEATURE:
<223> OTHER INFORMATION: Forward MLL-AF4 primer

<400> SEQUENCE: 17
ggaccgccaa gaaaag                                                         16

<210> SEQ ID NO 18
<211> LENGTH: 18
<212> TYPE: DNA
<213> ORGANISM: Artificial Sequence
<220> FEATURE:
<223> OTHER INFORMATION: Reverse MLL-AF4 primer

<400> SEQUENCE: 18
ctggggtttg ttcactgt                                                       18

<210> SEQ ID NO 19
<211> LENGTH: 19
<212> TYPE: DNA
<213> ORGANISM: Artificial Sequence
<220> FEATURE:
<223> OTHER INFORMATION: Forward 82M" primer

<400> SEQUENCE: 19
ggagcattca gacttgttt                                                      19

<210> SEQ ID NO 20
<211> LENGTH: 16
<212> TYPE: DNA
<213> ORGANISM: Artificial Sequence
<220> FEATURE:
<223> OTHER INFORMATION: Reverse 82M" primer

<400> SEQUENCE: 20
atgcggcatc ttcaaa                                                         16
```

THERAPY FOR MLL-REARRANGED LEUKEMIA

This application claims the benefit of U.S. provisional application No. 61/382,459, filed Sep. 13, 2010, the content of which is incorporated by reference herein in its entirety.

FIELD

Provided are methods for treating leukemias using histone deacetylase (HDAC) inhibitors. In one embodiment, the leukemia is MLL-rearranged acute lymphoid leukemia (ALL). Also provided are methods of treating MLL-rearranged ALL cell lines using HDAC inhibitors. In one embodiment, the methods comprise using a combination of an HDAC inhibitor and a demethylating agent.

SEQUENCE LISTING

Filed with the present specification is a paper and a computer readable form (CRF) copies of the Sequence Listing. The CRF entitled "12827-044-999-seqlist-final.txt" is created on Dec. 22, 2011 and is 22 kB in size. The content of the Sequence Listing information recorded in CRF is identical to the paper copy of the Sequence Listing, and includes no new matter, as required under 37 CFR 1.821(e), 1.821(f), 1.821 (g), 1.825(b), or 1.825(d). The Sequence Listing is incorporated herein by reference in its entirety.

BACKGROUND

MLL-rearranged infant ALL remains the most aggressive type of childhood leukemia for which adequate treatment regimens are still lacking (Pieters et al., Lancet 370(9583): 240-250, 2007; Pui et al., Lancet 371(9617):1030-1043, 2008). Conventional combination chemotherapy, successfully used to treat older children with ALL without MLL rearrangements, fails in over 50% of the infant MLL-rearranged leukemia cases. Despite recent efforts in the optimization of therapeutic approaches for infants, defined as children below the age of one year, with ALL, the prognosis for the majority of these patients remains dismal.

MLL-rearranged infant leukemia is a malignancy of white blood cells characterized by rearrangement of the mixed lineage leukemia (MLL) gene on chromosome 11q23. Unlike most other recurrent translocations, MLL rearrangements are found in leukemias classified as acute myelogenous leukemia (AML) and acute lymphoblastic leukemia (ALL). MLL-rearranged leukemias often express both myeloid- and lymphoid-associated genes. Approximately 80% of infants with ALL carry leukemia-specific translocations involving the MLL gene.

MLL-rearranged leukemias are distinguishable from other types of leukemias by their unique genome-wide gene expression profiles and leukemia-specific histone modifications (Armstrong et al. Nat Genet 30(1):41-47, 2002; Krivtsov et al. Cancer Cell 14(5):355-368, 2008; Krivtsov & Armstrong, Nat Rev Cancer 7(11):823-833, 2007; Stam et al., Blood 115(14):2835-2844, 2010). As the wild-type MLL gene is normally functioning as an epigenetic regulator through histone methyltransferase activity, abrogation of the normal function of MLL in hematopoietic cells leads to erroneous histone modifications. Apparently, such epigenetic deregulation favors leukemia development (Guenther et al., Genes Dev 22(24):3403-3408, 2008). Recently, it was shown that apart from inappropriate histone modifications, the epigenetic landscape in MLL-rearranged infant ALL cells is further altered by severe aberrant DNA methylation at numerous gene promoters (Stumpel et al., Blood 114(27):5490-5498, 2009). The majority of infants with MLL-rearranged ALL, especially those bearing translocation t(4;11), representing the most common type of MLL-rearrangement among infant ALL patients, suffer from severely hypermethylated leukemias.

The pattern of methylation has recently become an important topic for research. Studies have found that in normal tissue methylation of a gene is mainly localized in the coding region, which is cytosine-phosphate-guanine (CpG) poor. In contrast, the promoter region of the gene is unmethylated despite a high density of CpG islands in the region.

Neoplasia is characterized by "methylation imbalance" where genome-wide hypomethylation is accompanied by localized hypermethylation and an increase in expression of DNA methyltransferase (Chen et al., Nature 395 (6697):89-93, 1998). The overall methylation state in a cell might also be a precipitating factor in carcinogenesis as evidence suggests that genome-wide hypomethylation can lead to chromosome instability and increased mutation rates (Baylin et al., Adv. Cancer Res. 72:141-96, 1998). The methylation state of some genes can be used as a biomarker for tumorigenesis. For instance, hypermethylation of the pi-class glutathione S-transferase gene (GSTP1) appears to be a promising diagnostic indicator of prostate cancer (Nakayama et al., J. Cell. Biochem. 91(3):540-52, 2004).

As treatment of MLL-rearranged infant ALL remains a major challenge, there is a need for compounds and methods for the treatment of the disease.

SUMMARY

In one embodiment, provided herein are methods for screening for compounds capable of treating a disease based on gene expression data. In one embodiment, connectivity mapping on a gene expression signature of a disease is applied. In one embodiment, the disease is a hematological malignancy. In one embodiment, the hematological malignancy is MLL-rearranged ALL. In one embodiment, the hematological malignancy is MLL-rearranged infant ALL. In one embodiment, the gene expression signature corresponds to the genes most significantly hypomethylated in t(4:11)-positive infant ALL cells.

The hematological malignancies treated by the methods provided herein include, but are not limited to, lymphomas, leukemias, multiple myeloma, plasma cell-derived cancers, relapsed hematological malignancies, and refractory hematological malignancies. In one embodiment, lymphomas that can be treated by the methods provided herein include, but are not limited to, small lymphocytic lymphoma, follicular lymphoma, Mantle cell lymphoma, diffuse large B-cell lymphoma, Burkitt lymphoma, B-cell lymphoblastic lymphoma, small cleaved B-cell lymphoma, non-cleaved B-cell lymphoma, cutaneous T-cell lymphoma (CTCL), and peripheral T-cell lymphoma (PTCL). In one embodiment, leukemias that can be treated by the methods provided herein include, but are not limited to, acute lymphoid leukemia (ALL), chronic lymphocytic leukemia (CLL), acute myeloid leukemia (AML), MLL-rearranged ALL, and MLL-rearranged infant ALL. In one embodiment, the hematological malignancy is MLL-rearranged ALL. In one embodiment, the hematological malignancy is MLL-rearranged infant ALL.

In one embodiment, provided herein are methods for detecting hypomethylated proto-oncogenes in a patient's hematological malignancy, comprising: obtaining a biological sample from the patient's hematological malignancy;

measuring one or more levels of the hypomethylated proto-oncogenes' mRNA expression or otherwise identifying the presence of the hypomethylated proto-oncogenes (e.g., Northern blots, polymerase chain reaction (PCR), immunochemistry (IHC) or Western Blot); and comparing said measurement with a control measurement from a patient's hematological malignancy without the hypomethylated proto-oncogenes, wherein a change in the mRNA expression indicates the presence of the hypomethylated proto-oncogenes in said patient's hematological malignancy.

In one embodiment, provided herein are methods for predicting the likelihood of a patient having a hematological malignancy, for example MLL-rearranged ALL or MLL-rearranged infant ALL, being responsive to an HDAC inhibitor therapy, based on a gene expression signature of hypomethylated proto-oncogenes, comprising screening said patient's hematological malignancy for the presence of the hypomethylated proto-oncogenes, such as MYC, HOXA9, RUNX1, PARK7, RAN or SET, wherein the presence of the hypomethylated proto-oncogenes predicts a likelihood that the HDAC inhibitor will treat said hematological malignancy. In one embodiment, the HDAC inhibitor is romidepsin.

In one embodiment, provided herein are methods for predicting the likelihood of a patient having a hematological malignancy, for example MLL-rearranged ALL or MLL-rearranged infant ALL, being responsive to a combination therapy of an HDAC inhibitor and a DNA demethylating agent, based on a gene expression signature of hypomethylated proto-oncogenes, comprising screening said patient's hematological malignancy for the presence of the hypomethylated proto-oncogenes, such as MYC, HOXA9, RUNX1, PARK7, RAN or SET, wherein the presence of the hypomethylated proto-oncogenes predicts a likelihood that the combination of the HDAC inhibitor and the DNA demethylating agent will treat said hematological malignancy. In one embodiment, the HDAC inhibitor is romidepsin. In one embodiment, the DNA demethylating agent is 5-azacytidine.

In one embodiment, provided herein are methods for predicting therapeutic efficacy of treatment of a patient having a hematological malignancy, for example MLL-rearranged ALL or MLL-rearranged infant ALL, with an HDAC inhibitor, based on a gene expression signature of hypomethylated proto-oncogenes, comprising screening said patient's hematological malignancy for the presence of the hypomethylated proto-oncogenes, such as MYC, HOXA9, RUNX1, PARK7, RAN or SET, wherein the presence of the hypomethylated proto-oncogenes is predictive of therapeutic efficacy of treatment with the HDAC inhibitor therapy. In one embodiment, the HDAC inhibitor is romidepsin.

In one embodiment, provided herein are methods for predicting therapeutic efficacy of treatment of a patient having a hematological malignancy, for example MLL-rearranged ALL or MLL-rearranged infant ALL, with a combination of an HDAC inhibitor and a DNA demethylating agent, comprising screening said patient's hematological malignancy based on a gene expression signature of hypomethylated proto-oncogenes, such as MYC, HOXA9, RUNX1, PARK7, RAN or SET, wherein the presence of the hypomethylated proto-oncogenes is predictive of therapeutic efficacy of the combination of the HDAC inhibitor and the DNA demethylating agent. In one embodiment, the HDAC inhibitor is romidepsin. In one embodiment, the DNA demethylating agent is 5-azacytidine.

In one embodiment, provided herein is a method for treating MLL-rearranged ALL comprising administering to a patient in need of such treatment an effective amount of an HDAC inhibitor. In one embodiment, provided herein is a method for treating MLL-rearranged infant ALL comprising administering to a patient in need of such treatment an effective amount of an HDAC inhibitor. HDAC inhibitors for use in methods provided herein include, but are not limited to, trichostatin A (TSA), Vorinostat (SAHA), Valproic Acid (VPA), romidepsin and MS-275. In one embodiment, the HDAC inhibitor is romidepsin.

In one embodiment, provided herein is a method of treating MLL-rearranged ALL comprising administering to a patient in need of such treatment an effective amount of a combination of an HDAC inhibitor and a DNA demethylating agent. In one embodiment, provided herein is a method of treating MLL-rearranged infant ALL comprising administering to a patient in need of such treatment an effective amount of a combination of an HDAC inhibitor and a DNA demethylating agent. In one embodiment, a DNA demethylating agent acts additively with an HDAC inhibitor. In one embodiment, a DNA demethylating agent acts synergistically with an HDAC inhibitor. In one embodiment, the HDAC inhibitor is romidepsin. DNA demethylating agents for use in methods provided herein include, but are not limited to, 5-azacytidine (azacytidine), 5-azadeoxycytidine (decitabine), zebularine and procaine. In one embodiment, the DNA demethylating agent is 5-azacytidine, decitabine or zebularine. In one embodiment, the DNA demethylating agent is 5-azacytidine.

In one embodiment, provided herein is a pharmaceutical composition for treating MLL-rearranged ALL. In one embodiment, provided herein is a pharmaceutical composition for treating MLL-rearranged infant ALL. In one embodiment, the pharmaceutical composition comprises an HDAC inhibitor and a pharmaceutically acceptable carrier. In another embodiment, the pharmaceutical composition comprises an HDAC inhibitor and a DNA demethylating agent.

In one embodiment, provided herein are methods of treating cells ex vivo by contacting the cells with an HDAC inhibitor. The cells may be treated with a sufficient concentration of an HDAC inhibitor to kill the cells. In one embodiment, a sufficient concentration of an HDAC inhibitor is used to induce cell death. In one embodiment, the cells are neoplastic cells. In one embodiment, the cells are hematological cells. In one embodiment, the methods are useful for accessing the cytotoxicity of an HDAC inhibitor against a cancerous cell under certain conditions (e.g., concentration of an agent, etc.). In one embodiment, the methods may be used to ascertain the susceptibility of a subject's cancer or neoplasm to an HDAC inhibitor. In one embodiment, the cell is a t(4;11)-positive infant ALL cell. The HDAC inhibitors for use in the methods provided herein include, but are not limited to, trichostatin A (TSA), Vorinostat (SAHA), Valproic Acid (VPA), romidepsin and MS-275. In one embodiment, the HDAC inhibitor is romidepsin.

In one embodiment, provided herein are methods of treating cells ex vivo by contacting the cells with a combination of an HDAC inhibitor and a DNA demethylating agent. The cells may be treated with a sufficient concentration of the combination to kill the cells. In one embodiment, a sufficient concentration of the combination is used to induce cell death. In one embodiment, the cells are neoplastic cells. In one embodiment, the cells are hematological cells. In one embodiment, the methods are useful for accessing the cytotoxicity of the combination against a cancerous cell under certain conditions (e.g., concentration of an agent, etc.). In one embodiment, the methods may be used to ascertain the susceptibility of a subject's cancer or neoplasm to the combination. In one embodiment, the cell is a t(4;11)-positive infant ALL cell. The HDAC inhibitors for use in the methods provided herein include, but are not limited to, trichostatin A (TSA), Vorinostat (SAHA), Valproic Acid (VPA), romidepsin and MS-275. In one embodiment, the HDAC inhibitor is romidepsin. The DNA demethylating agents for use in the methods provided herein include, but are not limited to, 5-azacytidine (azacytidine), 5-azadeoxycytidine (decitabine), zebularine and procaine. In one embodiment, the DNA demethylating agent is 5-azacytidine, decitabine or zebularine. In one embodiment, the DNA demethylating agent is 5-azacytidine.

In one embodiment, provided herein are methods of treating cells in vitro by contacting the cells with an HDAC inhibitor. In one embodiment, the cells derived from neoplastic cell lines. In one embodiment, the neoplastic cell lines are hematological cell lines. The cell lines may be treated with a sufficient concentration of an HDAC inhibitor to kill the cells. In one embodiment, a sufficient concentration of an HDAC inhibitor is used to induce cell death. In one embodiment, the methods are useful for accessing the cytotoxicity of an HDAC inhibitor against a cancerous cell line under certain conditions (e.g., concentration of an agent, cell line, etc.). In one embodiment, the methods may be used to ascertain the susceptibility of a subject's cancer line or neoplasm to an HDAC inhibitor. In one embodiment, the cell line is a t(4;11)-positive infant ALL cell line. In a particular embodiment, the t(4;11)-positive infant ALL cell lines are SEM and RS4;11. The HDAC inhibitors for use in the methods provided herein include, but are not limited to, trichostatin A (TSA), Vorinostat (SAHA), Valproic Acid (VPA), romidepsin and MS-275. In one embodiment, the HDAC inhibitor is romidepsin.

In one embodiment, provided herein are methods of treating cells in vitro by contacting the cells with a combination of an HDAC inhibitor and a DNA demethylating agent. In one embodiment, the cells derived from neoplastic cell lines. In one embodiment, the neoplastic cell lines are hematological cell lines. The cell lines may be treated with a sufficient concentration of the combination to kill the cells. In one embodiment, a sufficient concentration of the combination is used to induce cell death. In one embodiment, the methods are useful for accessing the cytotoxicity of the combination against a cancerous cell line under certain conditions (e.g., concentration of an agent, cell line, etc.). In one embodiment, the methods may be used to ascertain the susceptibility of a subject's cancer line or neoplasm to the combination. In one embodiment, the cell line is a t(4;11)-positive infant ALL cell line. In a particular embodiment, the t(4;11)-positive infant ALL cell lines are SEM and RS4;11. The HDAC inhibitors for use in the methods provided herein include, but are not limited to, trichostatin A (TSA), Vorinostat (SAHA), Valproic Acid (VPA), romidepsin and MS-275. In one embodiment, the HDAC inhibitor is romidepsin. DNA demethylating agents for use in the methods provided herein include, but are not limited to, 5-azacytidine (azacytidine), 5-azadeoxycytidine (decitabine), zebularine and procaine. In one embodiment, the DNA demethylating agent is 5-azacytidine, decitabine or zebularine. In one embodiment, the DNA demethylating agent is 5-azacytidine.

In one embodiment, provided herein are kits comprising one or more containers filled with an HDAC inhibitor or a pharmaceutical composition thereof, reagents for detecting hypomethylated proto-oncogenes, such as MYC, HOXA9, RUNX1, PARK7, RAN or SET, in a patient having MLL-rearranged ALL or MLL-rearranged infant ALL, and instructions for detecting these hypomethylated proto-oncogenes in a patient having MLL-rearranged ALL or MLL-rearranged infant ALL.

In one embodiment, provided herein are kits comprising one or more containers filled with a combination of an HDAC inhibitor and a DNA demethylating agent, or a pharmaceutical composition thereof, reagents for detecting hypomethylated proto-oncogenes, such as MYC, HOXA9, RUNX1, PARK7, RAN or SET, in a patient having MLL-rearranged ALL or MLL-rearranged infant ALL, and instructions for detecting these hypomethylated proto-oncogenes in a patient having MLL-rearranged ALL or MLL-rearranged infant ALL.

The present embodiments can be understood more fully by reference to the detailed description and examples, which are intended to exemplify non-limiting embodiments.

BRIEF DESCRIPTION OF THE DRAWINGS

FIGS. 8AA, 8BB, 8CC, 8DD, 8EE, 8FF and 8GG show relative proto-oncogene mRNA expression after exposure to HDAC inhibitors in RS4;11 cell line. mRNA expression levels of the proto-oncogenes A. RAN, B. SET, C. MYC, D. RUNX1, E. HOXA9, F. PARK7 and G. DIAPH1 relative to the housekeeping gene B2M. mRNA expression levels were determined in the t(4;11)-positive cell lines SEM and RS4;11 exposed for 6 hours to different concentrations of the six HDAC inhibitors: TSA (1 mM), SAHA (10 µM), VPA (10 mM), romidepsin (10 ng/ml) and MS-275 (10 µM). For RUNX1, PARK7, DIAPH1 and HOXA9 data after 24 hours exposure are presented as well (hatch fill). Expression levels in SEM or RS4;11 were set to 100%.

DETAILED DESCRIPTION

Definitions

Figure 1A:
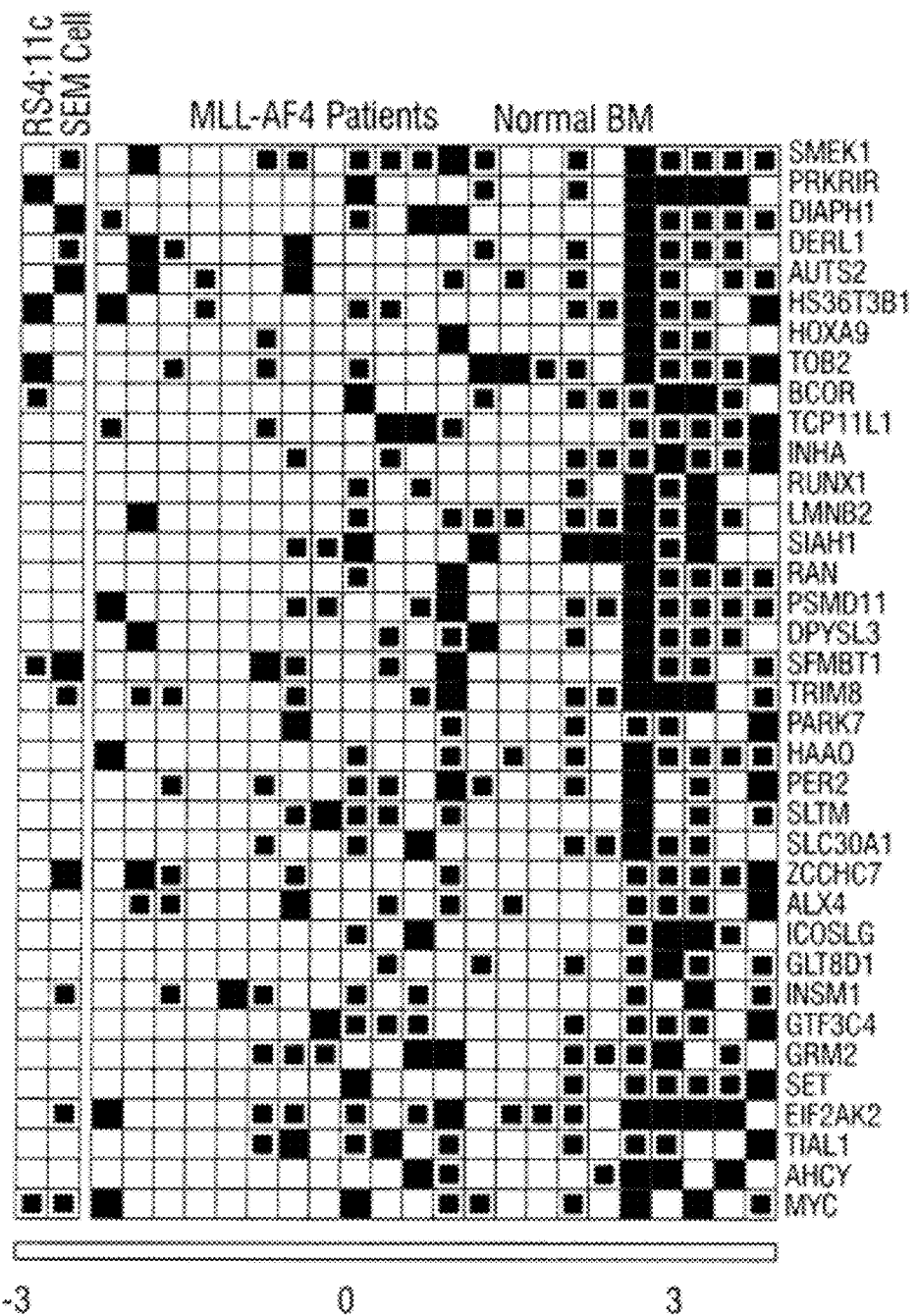
FIG. 1A displays the 36 genes most significantly hypomethylated in t(4;11)-positive infant ALL (n=15) as compared with normal bone marrows (n=7) that were consistently methylated in all normal bone marrow samples. Columns represent patient samples and rows represent genes. Relative DNA methylation levels are shown. Gene names are listed at the right.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. It should also be noted that use of "or" means "and/or" unless stated otherwise. Furthermore, use of the term "including" as well as other forms, such as "include," "includes," and "included" is not limiting.

The term "treating" as used herein, means an alleviation, in whole or in part, of symptoms associated with a disorder or disease (e.g., cancer or a tumor syndrome), or slowing, or halting of further progression or worsening of those symptoms.

The term "preventing" as used herein, means the prevention of the onset, recurrence or spread, in whole or in part, of the disease or disorder (e.g., cancer), or a symptom thereof.

The term "effective amount" in connection with the HDAC inhibitor means an amount capable of alleviating, in whole or in part, symptoms associated with a disorder, for example cancer, or slowing or halting further progression or worsening of those symptoms, or preventing or providing prophylaxis for cancer, in a subject at risk for cancer. The effective amount of the HDAC inhibitor, for example in a pharmaceutical composition, may be at a level that will exercise the desired effect; for example, about 0.005 mg/kg of a subject's body weight to about 100 mg/kg of a subject's body weight in unit dosage for both oral and parenteral administration. As will be apparent to those skilled in the art, it is to be expected that the effective amount of an HDAC inhibitor disclosed herein may vary depending on the severity of the indication being treated.

It is understood that the genes and/or proteins described herein are inclusive of allelic variant isoforms, synthetic nucleic acids and/or proteins, nucleic acid and/or proteins isolated from tissue and cells, and modified forms thereof. It is also understood that the genes and/or proteins described herein are also known to exist in various forms, including variants and mutants, and are contemplated herein. The genes and/or proteins described herein further include nucleic acid sequences and/or amino acid sequences having at least 65% identity with the gene or protein to be detected and are included within embodiments described herein.

The term "biological sample" is intended to include tissues (including, but are not limited to, tissue biopsies), cells, biological fluids and isolates thereof, isolated from a subject, as well as tissues, cells and fluids present within a subject.

The term "hematological malignancies" means types of cancer that affect blood, bone marrow and lymph nodes.

The term "leukemia" refers to malignant neoplasms of the blood-forming tissues. The leukemia includes, but is not limited to, chronic lymphocytic leukemia, (CLL), chronic myelocytic leukemia (CML), acute lymphoblastic leukemia (ALL), acute myelogenous leukemia (AML) and acute myeloblastic leukemia (AML). The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

The term "acute leukemia" means a disease that is characterized by a rapid increase in the numbers of immature blood cells that transform into malignant cells, rapid progression and accumulation of the malignant cells, which spill into the bloodstream and spread to other organs of the body.

The term "chronic leukemia" means a disease that is characterized by the excessive build up of relatively mature, but abnormal, white blood cells.

The term "lymphoma" means a type of cancer occurred in the lymphatic cells of the immune system and includes, but is not limited to, mature B-cell lymphomas, mature T-cell and natural killer cell lymphomas, Hodgkin's lymphomas and immunodeficiency-associated lymphoproliferative disorders.

The term "stereoisomer" refers to a isomeric molecule that has the same molecular formula and sequence of bonded atoms (constitution), but that differs only in the three-dimensional orientation of its atoms in space. Structural isomers share the same molecular formula, but the bond connections and/or their order differs between different atoms/groups. In stereoisomers, the order and bond connections of the constituent atoms remain the same, but their orientation in space differ The term "enantiomer" is one of two stereoisomers that are mirror images of each other that are "non-superposable" (not identical). Organic compounds that contain an asymmetric (chiral) carbon usually have two non-superimposable structures.

The term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

The term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center. In other words, the invention encompasses the use of the R or S enantiomer of immunomodulatory compound in the methods.

The term "animal" refers to any member of the animal kingdom. In some embodiment, "animal" refers to a human, at any stage of development. In some embodiment, "animal" refers to a non-human animal, at any stage of development.

As used herein, the terms "engineered" and "recombinant" cells or host cells are intended to refer to a cell into which an exogenous DNA segment or gene, such as a cDNA or gene encoding a protein has been introduced. Therefore, engineered cells are distinguishable from naturally occurring cells which do not contain a recombinantly introduced exogenous DNA segment or gene. Engineered cells are cells having a gene or genes introduced through the hand of man. Recombinant cells include those having an introduced cDNA or genomic gene, and also include genes positioned adjacent to a promoter not naturally associated with the particular introduced gene.

The term "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Each carrier must be "acceptable" in the sense of being compatible with the other ingredients of the formulation and not injurious to a subject to whom it is administered. Nor should an acceptable carrier alter the specific activity of the subject compounds.

The term "pharmaceutically acceptable" refers to molecular entities and compositions that are physiologically tolerable and do not typically produce an allergic or similar untoward reaction, such as gastric upset, dizziness and the like, when administered to a human.

The term "unit dose" when used in reference to a therapeutic composition refers to physically discrete units suitable as unitary dosage for humans, each unit containing a predetermined quantity of active material calculated to produce the desired therapeutic effect in association with the required diluent; i.e., carrier, or vehicle.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

Romidepsin

Romidepsin is a natural product which was isolated from *Chromobacterium violaceum* by Fujisawa Pharmaceuticals (Published Japanese Patent Application No. 64872, U.S. Pat. No. 4,977,138, issued Dec. 11, 1990, Ueda et al., *J. Antibiot* (Tokyo) 47:301-310, 1994; Nakajima et al., *Exp Cell Res* 241:126-133, 1998; and WO 02/20817; each of which is incorporated herein by reference. It is a bicyclic peptide consisting of four amino acid residues (D-valine, D-cysteine, dehydrobutyrine, and L-valine) and a novel acid (3-hydroxy-7-mercapto-4-heptenoic acid) containing both amide and ester bonds. In addition to the production from *C. violaceum* using fermentation, romidepsin can also be prepared by synthetic or semi-synthetic means. The total synthesis of romidepsin reported by Kahn et al. involves 14 steps and yields romidepsin in 18% overall yield (Kahn et al. *J. Am. Chem. Soc.* 118:7237-7238, 1996).

The chemical name of romidepsin is (1S,4S,7Z,10S,16E,21R)-7-ethylidene-4,21-bis(1-methylethyl)-2-oxa-12,13-dithia-5,8,20,23-tetrazabicyclo[8.7.6]tricos-16-ene-3,6,9,19,22-pentone. The empirical formula is $C_{24}H_{36}N_4O_6S_2$. The molecular weight is 540.71. At room temperature, romidepsin is a white powder.

It's structure is shown below (formula I):

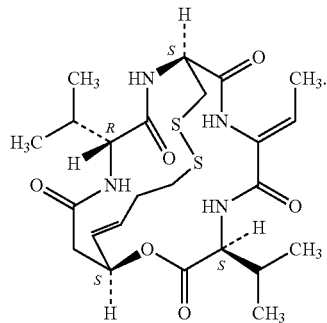

(I)

Romidepsin has been shown to have anti-microbial, immunosuppressive, and anti-tumor activities. It was tested, for example, for use in treating patients with hematological malignancies (e.g., cutaneous T-cell lymphoma (CTCL), peripheral T-cell lymphoma (PTCL), multiple myeloma, etc.) and solid tumors (e.g., prostate cancer, pancreatic cancer, etc.) and is thought to act by selectively inhibiting deacetylases (e.g., histone deacetylase, tubulin deacetylase), thus promising new targets for the development of a new class of anti-cancer therapies (Nakajima et al., *Exp Cell Res* 241:126-133, 1998). One mode of action of romidepsin involves the inhibition of one or more classes of histone deacetylases (HDAC). Preparations and purification of romidepsin is described, for example, in U.S. Pat. No. 4,977,138 and International PCT Application Publication WO 02/20817, each of which is incorporated herein by reference.

Exemplary forms of romidepsin include, but are not limited to, salts, esters, pro-drugs, isomers, stereoisomers (e.g., enantiomers, diastereomers), tautomers, protected forms, reduced forms, oxidized forms, derivatives, and combinations thereof, with the desired activity (e.g., deacetylase inhibitory activity, aggressive inhibition, cytotoxicity). In certain embodiments, romidepsin is a pharmaceutical grade material and meets the standards of the U.S. Pharmacopoeia, Japanese Pharmacopoeia, or European Pharmacopoeia. In certain embodiments, the romidepsin is at least 95%, at least 98%, at least 99%, at least 99.9%, or at least 99.95% pure. In certain embodiments, the romidepsin is at least 95%, at least 98%, at least 99%, at least 99.9%, or at least 99.95% monomeric. In certain embodiments, no impurities are detectable in the romidepsin materials (e.g., oxidized material, reduced material, dimerized or oligomerized material, side products, etc.). Romidepsin typically includes less than 1.0%, less than 0.5%, less than 0.2%, or less than 0.1% of total other unknowns. The purity of romidepsin may be assessed by appearance, HPLC, specific rotation, NMR spectroscopy, IR spectroscopy, UV/Visible spectroscopy, powder x-ray diffraction (XRPD) analysis, elemental analysis, LC-mass spectroscopy, or mass spectroscopy.

In one embodiment, romidepsin is a derivative of romidepsin of the formula (II):

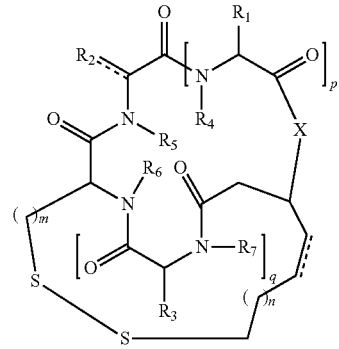

(II)

wherein
n is 1, 2, 3 or 4;
n is 0, 1, 2 or 3;
p and q are independently 1 or 2;
X is O, NH, or $NR_8$;
$R_1$, $R_2$, and $R_3$ are independently hydrogen, unsubstituted or substituted, branched or unbranched, cyclic or acyclic aliphatic; unsubstituted or substituted, branched or unbranched, cyclic or acyclic heteroaliphatic; unsubstituted or substituted aryl; or unsubstituted or substituted heteroaryl; and $R_4$, $R_5$, $R_6$, $R_7$ and $R_8$ are independently hydrogen, or substituted or unsubstituted, branched or unbranched, cyclic or acyclic aliphatic; and pharmaceutically acceptable forms thereof.

In one embodiment, m is 1, n is 1, p is 1, q is 1, X is O, $R_1$, $R_2$, and $R_3$ are unsubstituted or substituted, branched or unbranched acyclic aliphatic. In one embodiment, $R_4$, $R_5$, $R_6$ and $R_7$ are all hydrogen.

In one embodiment, the derivative of romidepsin is of the formula (III):

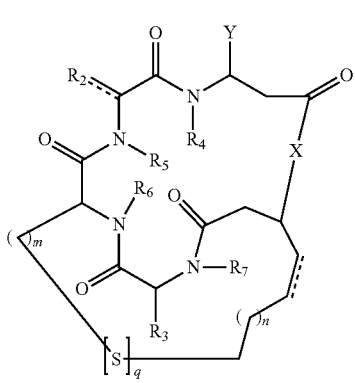

(III)

wherein:
m is 1, 2, 3 or 4;
n is 0, 1, 2 or 3;
q is 2 or 3;
X is O, NH, or $NR_B$;
Y is ORB, or $SR_8$;
$R_2$ and $R_3$ are independently hydrogen, unsubstituted or substituted, branched or unbranched, cyclic or acyclic aliphatic, unsubstituted or substituted, branched or unbranched, cyclic or acrylic heteroaliphatic, unsubstituted or substituted aryl or unsubstituted or substituted heteroaryl;
$R_4$, $R_5$, $R_6$, $R_7$ and $R_8$ are independently selected from hydrogen or substituted or unsubstituted, branched or unbranched, cyclic or acyclic aliphatic, and pharmaceutically acceptable forms thereof.

In one embodiment, m is 1, n is 1, q is 2, X is NH and $R_2$ and $R_3$ are unsubstituted or substituted, branched or unbranched, acyclic aliphatic. In one embodiment, $R_4$, $R_5$, $R_6$ and $R_7$ are all hydrogen.

In one embodiment, the derivative of romidepsin is of the formula (IV):

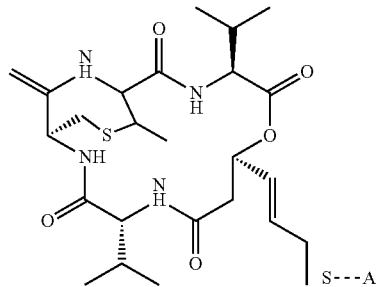

(IV)

wherein:

A is a moiety that is cleaved under physiological conditions to yield a thiol group and includes, for example, an aliphatic or aromatic acyl moiety (to form a thioester bond), an aliphatic or aromatic thioxy (to form a disulfide bond), or the like, and pharmaceutically acceptable forms thereof. Such aliphatic or aromatic groups can include a substituted or unsubstituted, branched or unbranched, cyclic or acyclic aliphatic group, a substituted or unsubstituted aromatic group, a substituted or unsubstituted heteroaromatic group, or a substituted or unsubstituted heterocyclic group. A can be, for example, —$COR_1$, —SC(=0)-0-$R_1$, or —$SR_2$;

$R_1$ is independently hydrogen, substituted or unsubstituted amino, substituted or unsubstituted, branched or unbranched, cyclic or acyclic aliphatic, substituted or unsubstituted aromatic group, substituted or unsubstituted heteroaromatic group, or a substituted or unsubstituted heterocyclic group. In one embodiment, $R_1$ is hydrogen, methyl, ethyl, n-propyl, isopropyl, n-butyl, isobutyl, benzyl, or bromobenzyl;

$R_2$ is a substituted or unsubstituted, branched or unbranched, cyclic or acyclic aliphatic group, a substituted or unsubstituted aromatic group, a substituted or unsubstituted heteroaromatic group, or a substituted or unsubstituted heterocyclic group.

In one embodiment, $R_2$ is methyl, ethyl, 2-hydroxyethyl, isobutyl, a fatty acid, a substituted or unsubstituted benzyl, a substituted or unsubstituted aryl, cysteine, homocysteine, or glutathione.

In one embodiment, the derivative of romidepsin is of formula (V) or (V'):

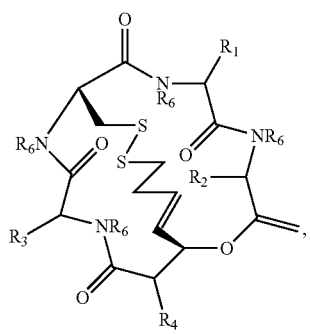

(V)

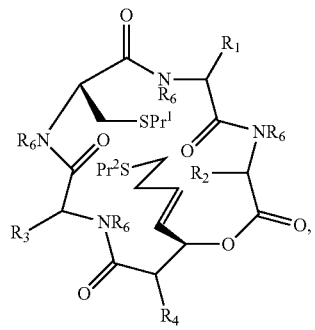

(V')

wherein:

each of $R_1$, $R_2$, $R_3$ and $R_4$ is the same or different and represent an amino acid side chain moiety;

each $R_6$ is the same or different and represents hydrogen or $(C_1-C_4)$alkyl; and $Pr^1$ and $Pr^2$ are the same or different and represent hydrogen or thiol-protecting group.

In one embodiment, the amino acid side chain moieties are those derived from natural amino acids. In one embodiment, the amino acid side chain moieties are those derived from unnatural amino acids.

In one embodiment, each amino acid side chain is a moiety selected from hydrogen, $(C_1-C_6)$alkyl, $(C_2-C_6)$alkenyl, -L-O—C(0)-R', -L-C(0)-0-R", -L-A, -L-NR"R", -L-Het-C(0)-Het-R", and -L-Het-R", wherein L is a $(C_1-C_6)$alkylene group, A is phenyl or a 5- or 6-membered heteroaryl group, each R' is the same or different and represents $(C_1-C_4)$alkyl, each R" is the same or different and represent H or $(C_1-C_6)$ alkyl, each -Het- is the same or different and is a heteroatom spacer selected from -0-, —N(R''')—, and —S—, and each R''' is the same of different and represents hydrogen or $(C_1-C_4)$alkyl.

In one embodiment, $R_6$ is hydrogen.

In one embodiment, $Pr^1$ and $Pr^2$ are the same or different and are selected from hydrogen and a protecting group selected from a benzyl group which is optionally substituted by $(C_1-C_6)$alkoxy, $(C_1-C_6)$acyloxy, hydroxy, nitro, picolyl, picolyl-N-oxide, anthrylmethyl, diphenylmethyl, phenyl, t-butyl, adamanthyl, $(C_1-C_6)$acyloxymethyl, $(C_1-C_6)$alkoxymethyl, tetrahydropyranyl, benzylthiomethyl, phenylthiomethyl, thiazolidine, acetamidemethyl, benzamidomethyl, tertiary butoxycarbonyl (BOC), acetyl and its derivatives, benzoyl and its derivatives, carbamoyl, phenylcarbamoyl, and $(C_1-C_6)$alkylcarbamoyl. In one embodiment, $Pr^1$ and $Pr^2$ are hydrogen.

Various romidepsin derivatives of formula (V) and (V') are disclosed in PCT application publication WO 2006/129105, published Dec. 7, 2006, which is incorporated herein by reference.

DNA Demethylating Agents

DNA demethylating agents are compounds that can inhibit DNA methylation, resulting in the expression of the previously hypermethylated silenced genes. DNA demethylating agents suitable for the methods provided herein include, but are not limited to, 5-azacytidine (azacytidine), 5-azadeoxycytidine (decitabine), zebularine and procaine. Azacytidine and decitabine have been approved in the treatment of Myelodysplastic syndrome (MDS) by Food and Drug Administration (FDA) in the United States and are marketed as Vidaza and Dacogen, respectively. Procaine is a DNA-demethylating agent with growth-inhibitory effects in human cancer cells (Villar-Garea et al., *Cancer Research* 63 (16): 4984-4989, 2003). In one embodiment, the DNA demethylating agent is 5-azacytidine, decitabine or zebularine. In one embodiment, the DNA demethylating agent is 5-azacytidine.

Methods for Screening for Compounds to Treat MLL-Rearranged ALL

The Connectivity Map (cmap) is a useful tool in a search for compounds capable of treating a disease based on gene expression data. In one embodiment, connectivity mapping on a gene expression signature of a disease is applied. In one embodiment, the disease is MLL-rearranged ALL. In one embodiment, the disease is MLL-rearranged infant ALL.

The cmap is a large collection of gene expression data from cultured human cell lines, including the leukemia cell line HL60, treated with a broad selection of FDA-approved compounds in varying concentrations (Lamb et al., *Science* 313 (5795):1929-1935, 2006). In one embodiment, the cmap is the connectivity map build02 (www.broadinstitute.org/cmap) consisting of 7056 gene expression profiles corresponding to 1309 bioactive compounds and generating 6100 treatment-vehicle pairs (or instances). Using pattern-matching algorithms, the cmap enables the discovery of therapeutic agents that are potentially able to reverse a presented expression signature through the feature of common gene-expression changes (Lamb et al, 2006, supra; Lamb, *Nat Rev Cancer* 7(1):54-60, 2007). In one embodiment, the cmap uses a gene set enrichment metric to rank order individual treatment instances by their similarity to the t(4;11)-positive infant ALL gene expression signature. The output consists of small-molecule compounds with an assigned gene enrichment metric: the connectivity score. The connectivity score represents the correlation between the query signature profile and the gene profile of treated cell lines compared with controls. The connectivity score comprises an up-score and a down-score. The down-score is a value between −1 and 1. The down-score represents the absolute enrichment of the interrogated gene signature with a given compound. In one embodiment, a compound with high negative down-score induces down-regulation of the query signature. In one embodiment, the compounds suitable for methods provided herein are selected based on the highest negative down-scores.

The examination of the obtained DNA methylation patterns of the MLL-rearranged ALL cells, in particular MLL-rearranged infant ALL cells, revealed that besides vast amounts of hypermethylated genes, numerous genes were hypomethylated in a leukemia-specific manner. In one embodiment, the hypomethylated genes are proto-oncogenes. In one embodiment, the proto-oncogenes include, but are not limited to, MYC, HOXA9, RUNX1, PARK7, RAN and SET. In one embodiment, the proto-oncogenes are highly expressed in primary t(4;11)-positive infant ALL cells. High expression of proto-oncogenes contributes to leukemia development and progression, and their deviant hypomethylated status in t(4;11)-positive infant ALL is pathologic.

Figure 1B:
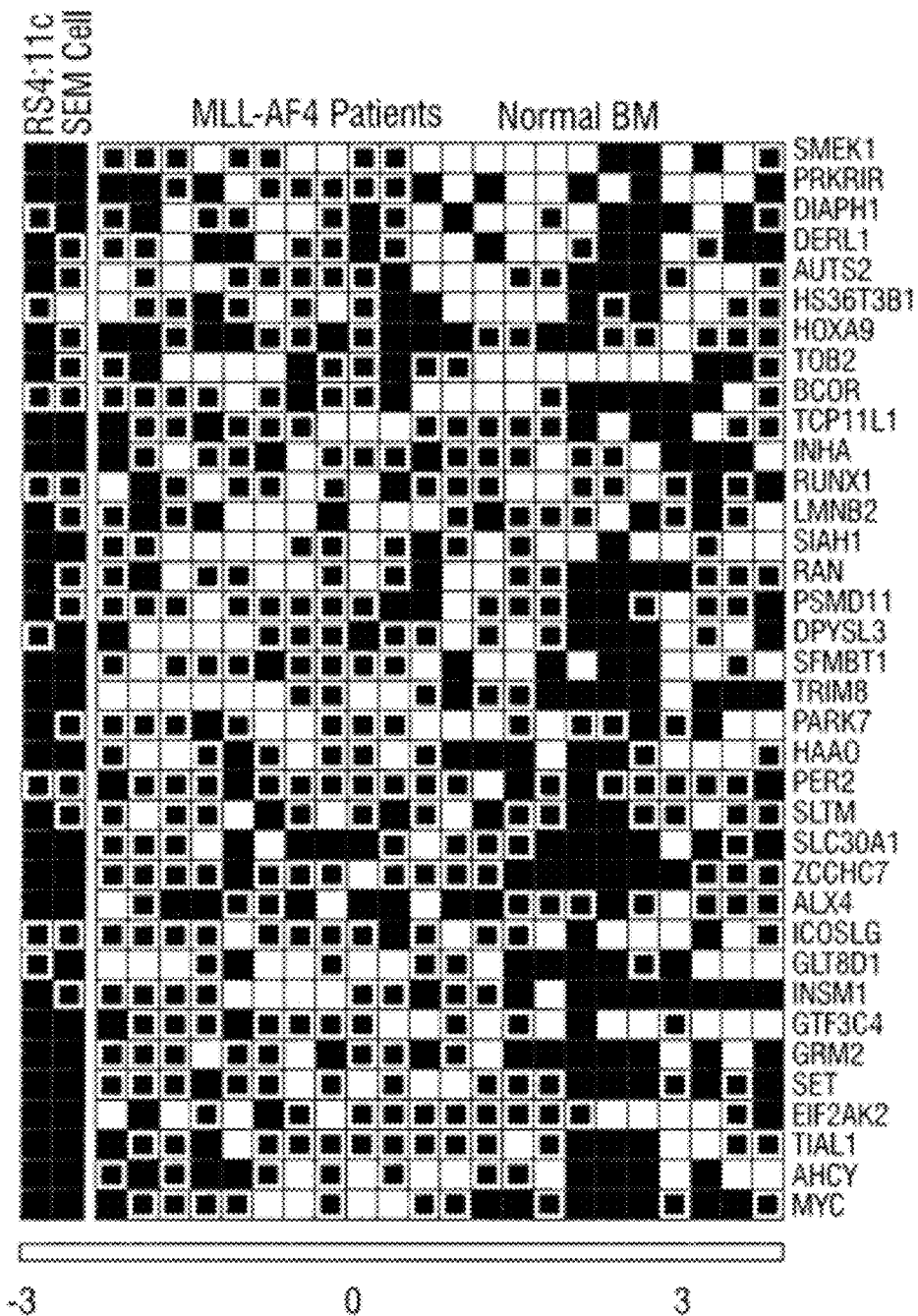
FIG. 1B displays heatmap showing the gene expression profiles for the same patients and the same genes for which DNA methylation profiles were presented in Figure A. Relative gene expression values are shown.
Figure 1C:
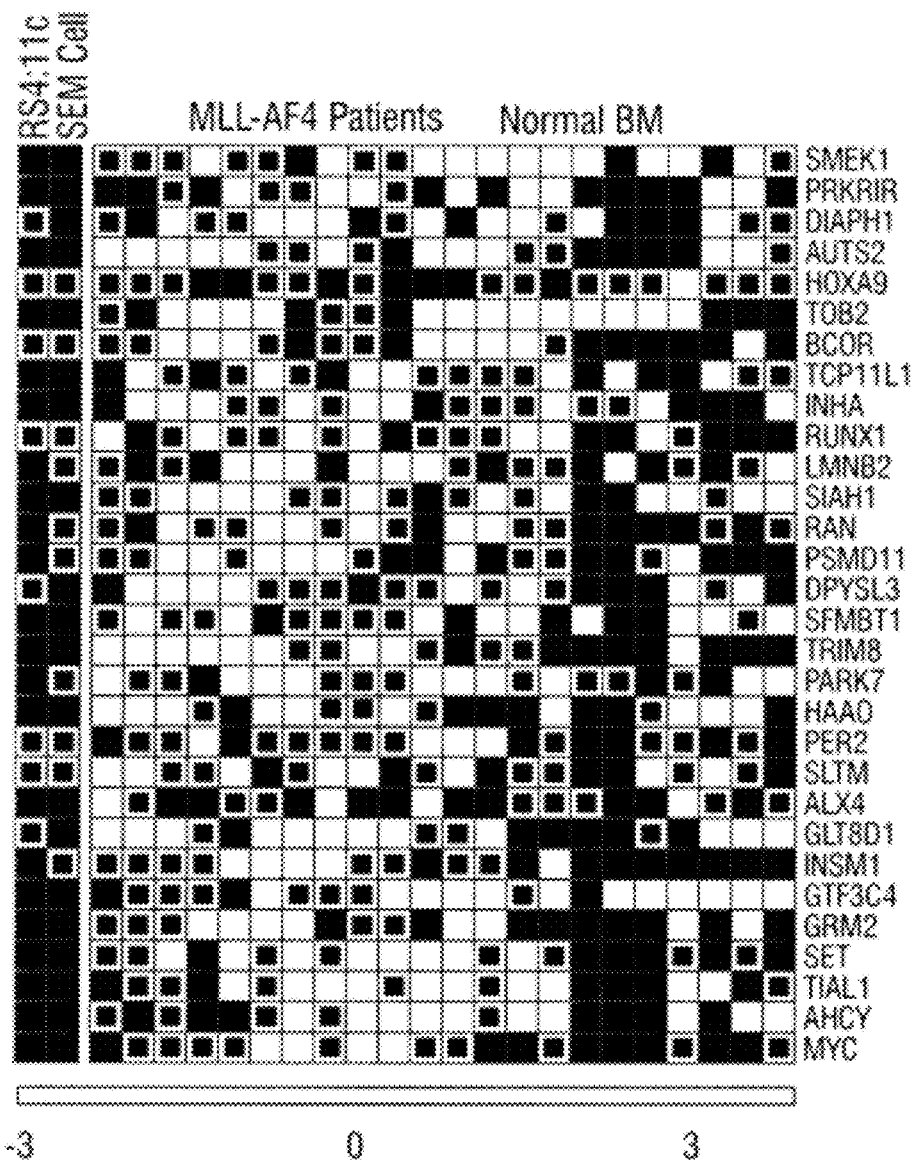
FIG. 1C shows gene expression profiles after elimination of 6 probes that were not present on the previous Affymetrix HU133A platform which was used for the generation of the connectivity map (cmap).

In one embodiment, the gene expression signature corresponds to the genes most significantly hypomethylated in t(4:11)-positive infant ALL cells. FIG. 1 shows the list of hypomethylated and highly expressed genes, including proto-oncogenes, as potential targets for therapeutic intervention. In one embodiment, the cmap is applied on a gene expression profile (FIG. 1B) matching to the obtained hypomethylation signature (FIG. 1A). In one embodiment, the gene expression signature consisting of 36 hypomethylated and highly expressed in t(4:11)-positive infant ALL cells genes (FIG. 1C) is used. The characteristics of these genes (Agilent and Affymetrix probe IDs, gene symbols and descriptions, log-fold changes and p-values adjusted for multiple testing (limma analyses in R)) are listed in Table 1 below.

TABLE 1

| Agilent Probe Name | AffymetrixProbe Name | Gene ID | Gene Name | Log fold change methylation | Adjusted p value methylation | Adjusted p value expression |
|---|---|---|---|---|---|---|
| A_17_P16727446 | 220368_s_at | SMEK1 | SMEK homolog 1, suppressor of mek1 | −2.00834 | 8.89E−11 | 0.002271 |
| A_17_P16475281 | 209323_at | PRKRIR | protein-kinase, interferon-inducible double stranded RNA dependent inhibitor, repressor of | −1.73279 | 1.05E−08 | 0.073336 |
| A_17_P15747745 | 209190_s_at | DIAPH1 | diaphanous homoloQ 1 | −1.65035 | 2.00E−08 | 0.02082 |
| A_17_P06441385 | 222543_at | DERL1 | Der1-like domain family, member 1 | −1.53553 | 2.42E−08 | 0.011972 |
| A_17_P05519645 | 212599_at | AUTS2 | Autism susceptibility candidate 2 | −1.73675 | 2.96E−08 | 1.37E−05 |
| A_17_P10244001 | 227361_at | HS3ST3B1 | Heparan sulfate (glucosamine) 3-0sulfotransferase 3B 1 | −1.73185 | 2.76E−09 | 0.00247 |
| A_17_P15920204 | 214651_s_at | HOXA9 | homeobox A9 | −1.7832 | 5.65E−08 | 0.021595 |
| A_17_P11512146 | 221496_s_at | TOB2 | transducer ofERBB2, 2 | −1.22345 | 8.92E−08 | 6.30E−05 |
| A_17_P11713320 | 219433_at | BCOR | BCL6 co-repressor | −2.04217 | 2.42E−08 | 8.03E−06 |
| A_17_P16433711 | 205797_s_at | TCP11L1 | t-complex 11 (mouse)-like 1 | −1.30468 | 1.26E−07 | 0.000729 |
| A_17_P15384777 | 210141_s_at | INHA | Inhibin, alpha | −1.85348 | 8.92E−08 | 0.005249 |
| A_17_P17233302 | 210365_at | RUNX1 | runt-related transcription factor 1 | −1.51025 | 1.30E−07 | 2.00E−05 |
| A_17_P10857565 | 218188_s_at | LMNB2 | lamin B2 | −1.64742 | 1.02E−07 | 2.82E−05 |
| A_17_P16893168 | 202980_s_at | SIAH1 | seven in absentia homolog 1 | −1.37243 | 1.58E−07 | 0.015415 |
| A_17_P16604897 | 200750_s_at | RAN | RAN, member RAS oncogene family | −1.70187 | 1.21E−07 | 3.54E−05 |
| A_17_P16970587 | 208777_s_at | PSMD11 | oroteasome 26S subunit, non-ATPase, 11 | −1.32754 | 1.90E−07 | 0.001813 |
| A_17_P15750644 | 201431_s_at | DPYSL3 | Dihydropyrimidinase-like 3 | −1.93691 | 1.58E−07 | 0.00028 |
| A_17_P15439580 | 213370_s_at | SFMBT1 | Scm-like with four mbt domains 1 | −1.08765 | 3.87E−07 | 0.008544 |
| A_17_P16379748 | 221012_s_at | TRIM8 | tripartite motif-containing 8 | −1.27598 | 2.47E−07 | 0.000123 |
| A_17_P15020491 | 200006_at | PARK7 | Parkinson disease 7 | −1.43134 | 2.47E−07 | 0.004873 |
| A_17_P01134075 | 205657_at | HAAO | 3-hydroxyanthranilate 3,4-dioxVQenase | −1.59896 | 2.47E−01 | 0.0009T4 |
| A_17_P15398519 | 205251_at | PER2 | period homoloQ 2 | −1.45926 | 3.22E−07 | 0.000299 |
| A_17_P16794555 | 217828_at | SLTM | SAFB-like, transcription modulator | −1.40512 | 3.53E−07 | 0.00521 |
| A_17_P0-0775037 | 228181_at | SLC30A1 | solute carrier family 30, member 10 | −1.75599 | 2.47E−07 | 0.00028 |

TABLE 1-continued

| Agilent Probe Name | AffymetrixProbe Name | Gene ID | Gene Name | Log fold change methylation | Adjusted p value methylation | Adjusted p value expression |
|---|---|---|---|---|---|---|
| A_17_P16175760 | 226496_at | ZCCHC7 | zinc finQer, CCHC domain containing 7 | −1.15624 | 5.02E−07 | 5.45E−12 |
| A_17_P16440138 | 208330_at | ALX4 | aristaless-like homeobox 4 | −1.2253 | 5.02E−07 | 0.01644 |
| A_17_P11411430 | 228976_at | ICOSLG | inducible T-cell co-stimulator liQand | −1.38402 | 3.93E−07 | 0.00028 |
| A_17_P02241304 | 218147_s_at | GLT8D1 | Qlvcosyltransferase 8 domain containina 1 | −1.19841 | 6.75E−07 | 0.000703 |
| A_17_P11104475 | 206502_s_at | INSM1 | Insulinoma-associated 1 | −1.26348 | 4.70E−07 | 0.000283 |
| A_17_P16270082 | 219198_at | GTF3C4 | General transcription factor IIIC, polypeptide 4 | −1.45363 | 4.70E−07 | 0.206367 |
| A_17_P15438081 | 208465_at | GRM2 | Qlutamate receptor, metabotropic 2 | −1.4313 | 4.70E−07 | 0.001243 |
| A_17_P16266012 | 200631_s_at | SET | SET translocation | −1.05908 | 1.69E−06 | 2.27E−05 |
| A_17_P15234061 | 242898_at | EIF2AK2 | eukaryotic translation initiation factor 2alpha kinase 2 | −0.94547 | 1.54E−06 | 0.009274 |
| A_17_P07522030 | 202405_at | TIAL1 | TIA1 cytotoxic granule-associated RNA bindina orotein-like 1 | −1.74357 | 3.87E−07 | 0.000219 |
| A_17_P11140901 | 200903_s_at | AHCY | S-adenosylhomocysteine hydrolase | −1.35635 | 1.09E−06 | 0.001154 |
| A_17_P06461251 | 202431_s_at | MYC | myc myelocytomatosis viral oncogene homolog (avian) | −1.65146 | 1.44E−06 | 2.23E−05 |

In one embodiment, the hypomethylated status of the selected genes allowed pronounced expression in t(4;11)-positive infant ALL cells.

Figure 2:
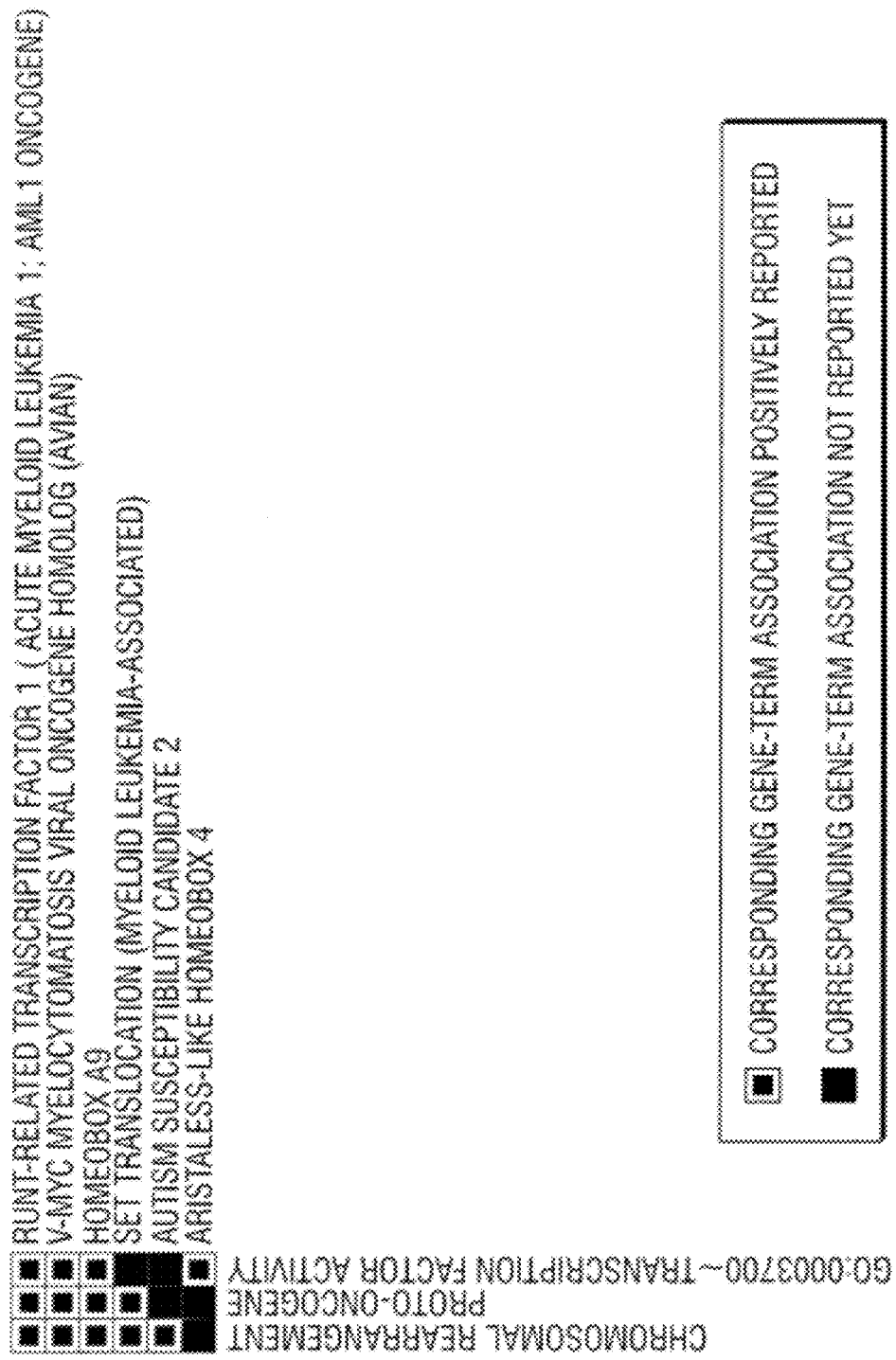
FIG. 2 shows the results obtained from the DAVID gene ontology database.
Figure 3A:
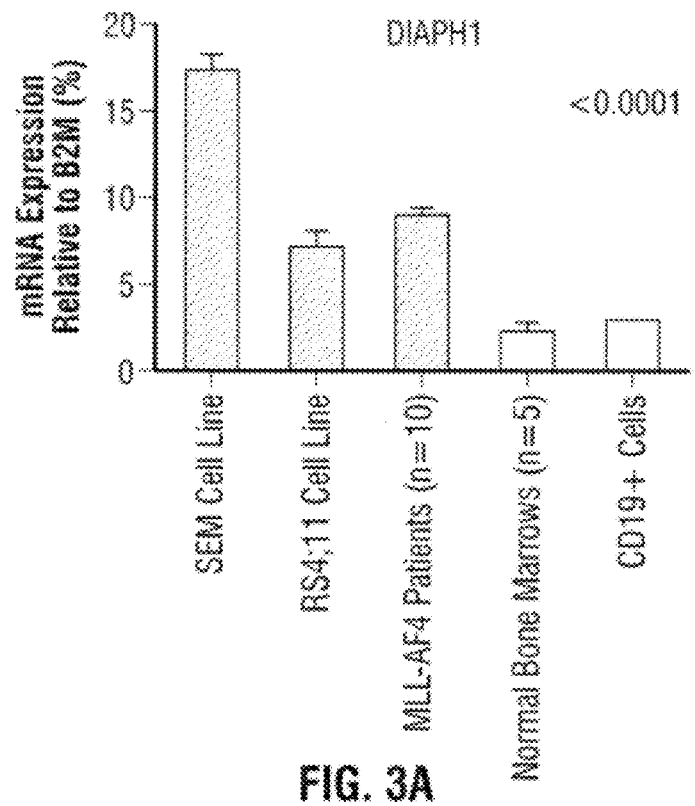
FIGS. 3A, 3B, 3C, 3D, 3E, 3F, 3G and 3H show mRNA expression levels of the proto-oncogenes: DIAPH1, HOXA9, RUNX1, RAN, SFMBT1, PARK7, SET and MYC, respectively, relative to the housekeeping gene B2M. mRNA expression levels were determined in the t(4;11)-positive cell lines SEM and RS4;11, MLL-AF4 patients (n=10), normal bone marrow samples (n=5) and $CD19^+$ B cells. P-values [t(4;11)-positive patients compared with normal bone marrows] obtained from a Mann-Whitney U test.
Figure 3B:
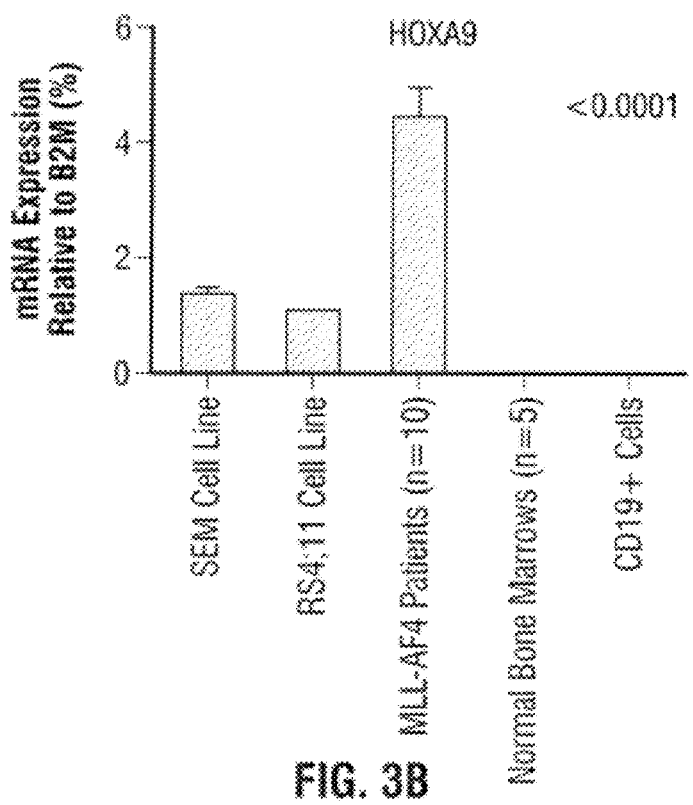
Figure 3C:
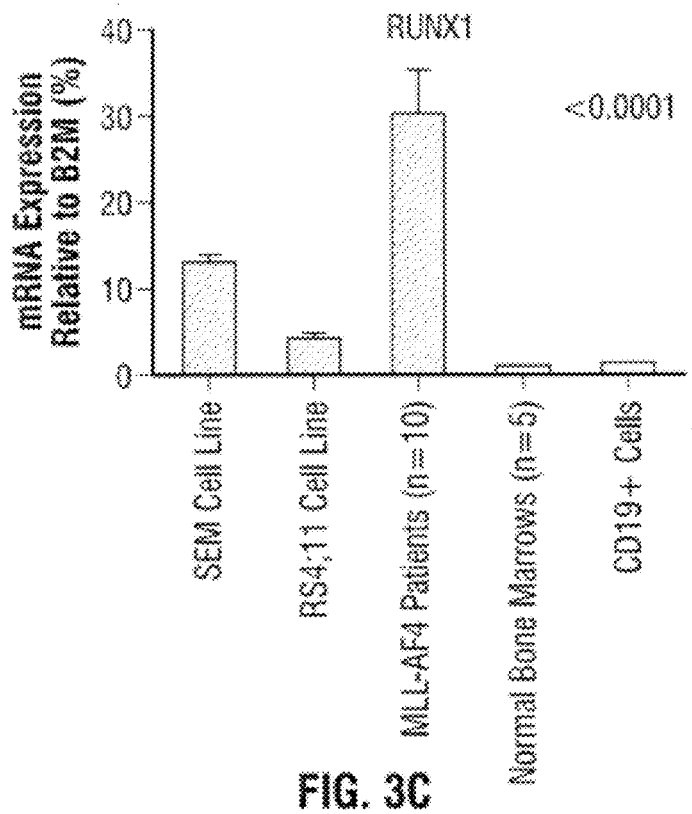
Figure 3D:
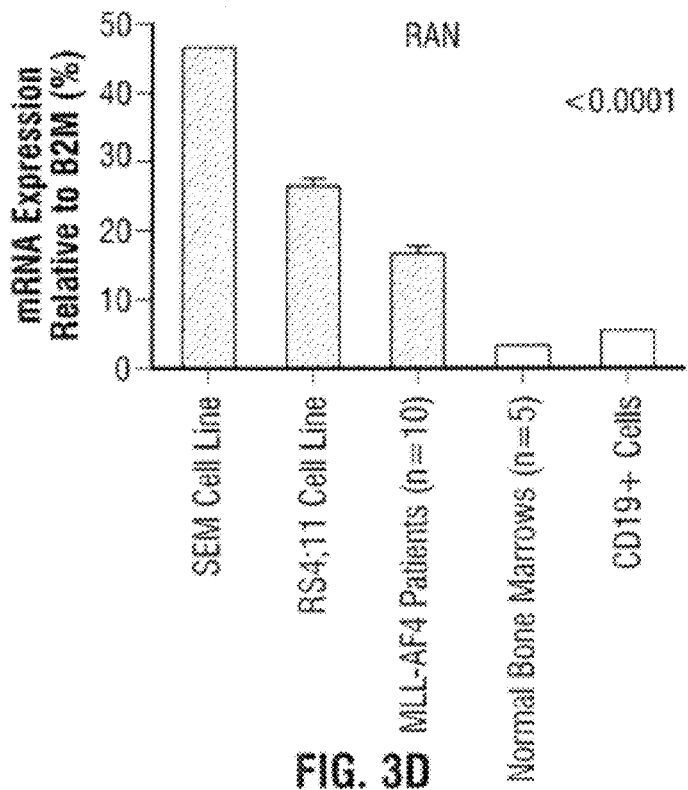
Figure 3E:
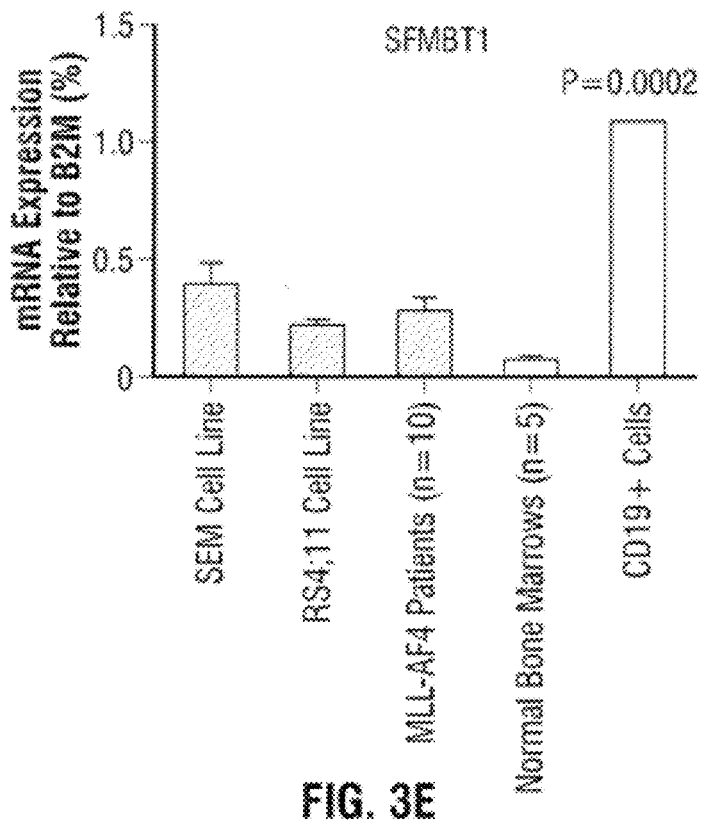
Figure 3F:
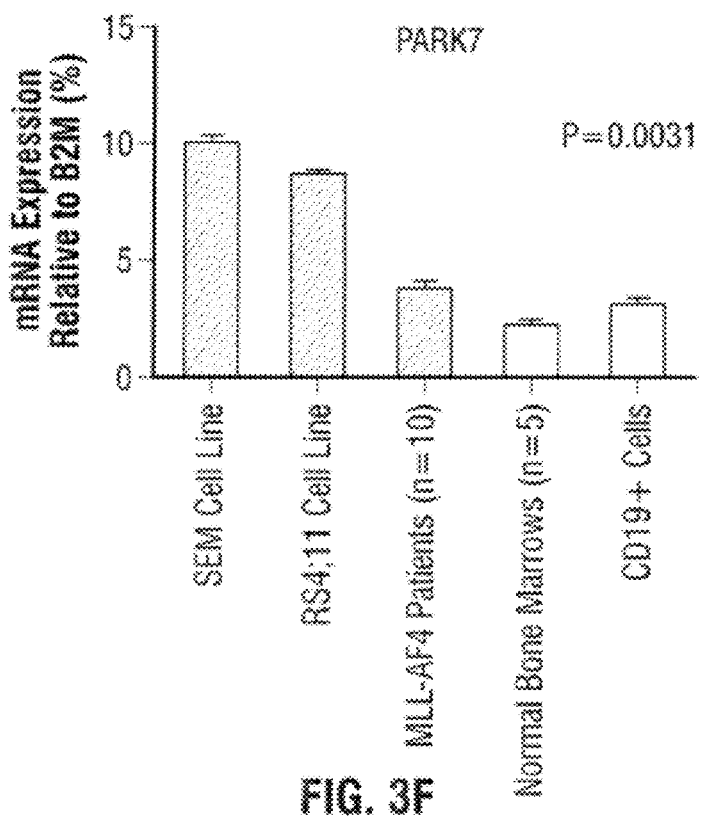
Figure 3G:
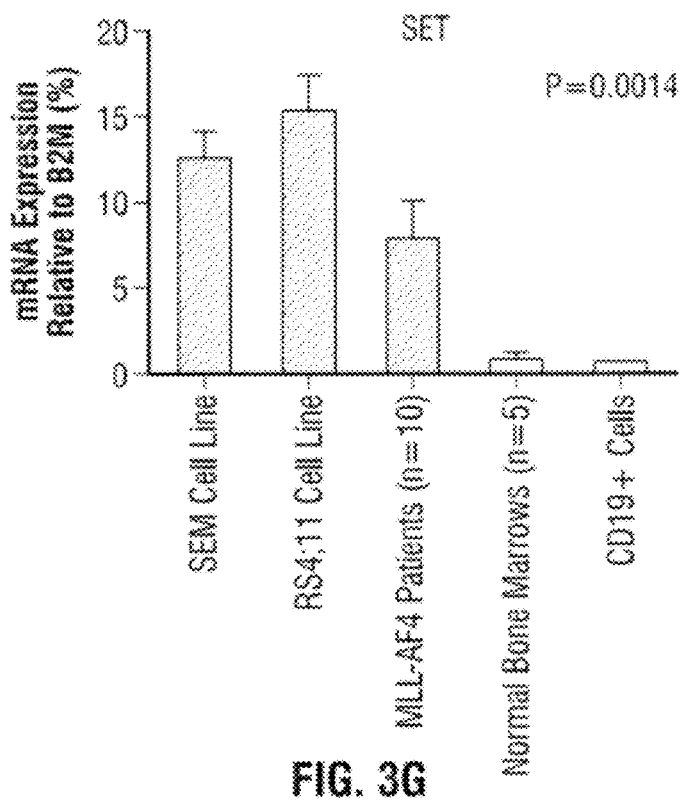
Figure 3H:
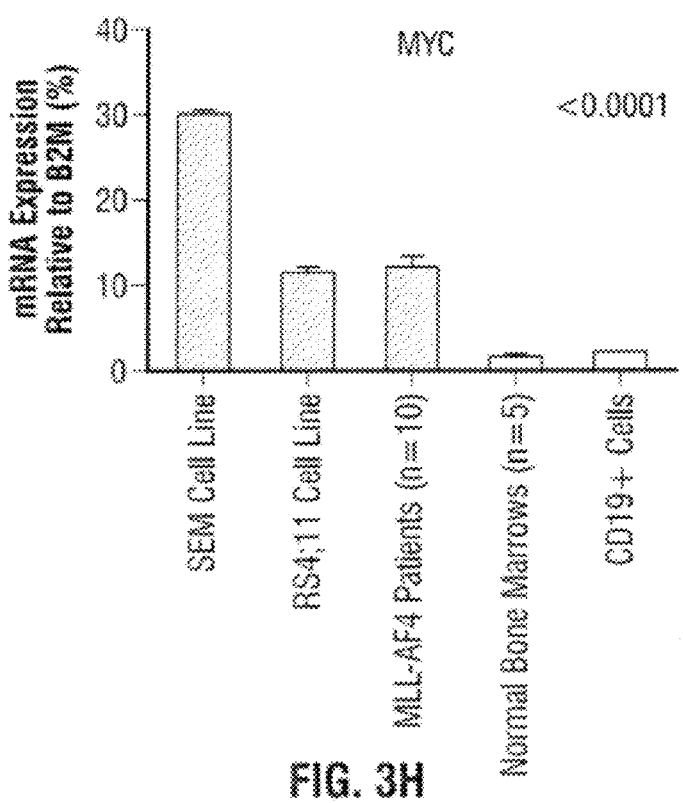
Figure 4A:
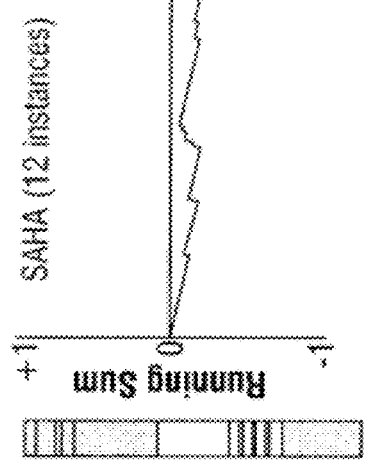
FIGS. 4A, 4B, 4C and 4D show the results obtained from the connectivity map. The bar-view is constructed from horizontal lines, each representing an individual treatment-control pair (instance). The instances are ordered by their corresponding enrichment in the t(4;11)-positive infant ALL query signature. For each HDAC inhibitor all instances are shown in solid line. Double line indicates a strong positive correlation with the queried signature and dotted line indicates a strong negative correlation. The HDAC inhibitors TSA (4A), SAHA (4B), VPA (4C) and MS-275 (4D) are shown.
Figure 4B:
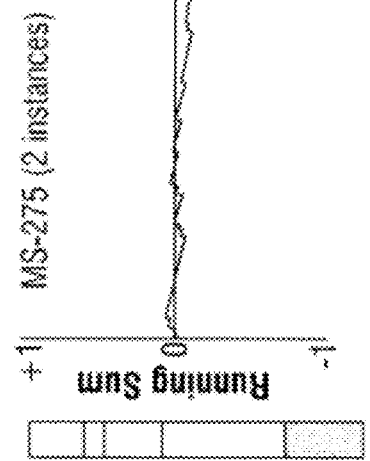
Figure 4C:
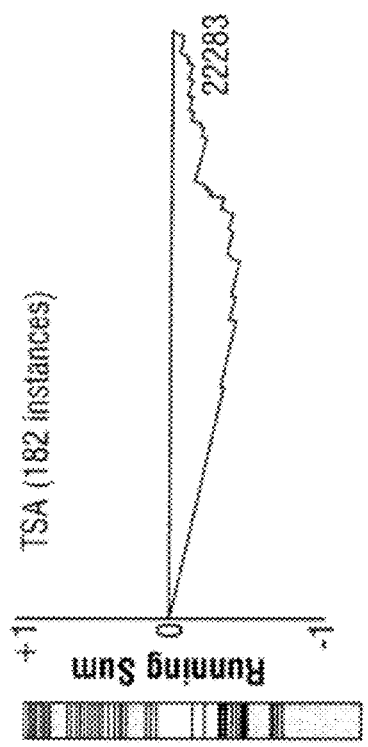
Figure 4D:
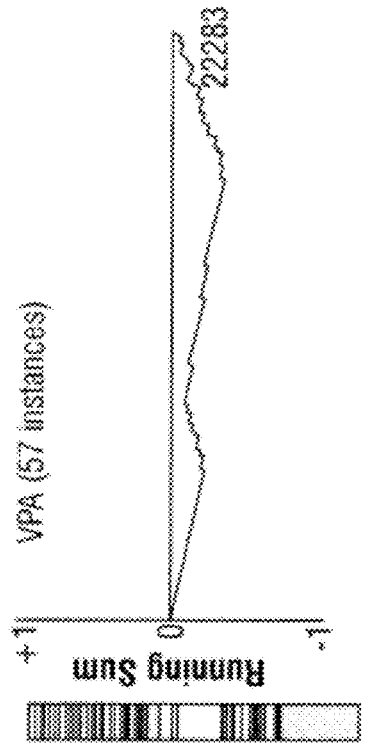
Figure 5A:
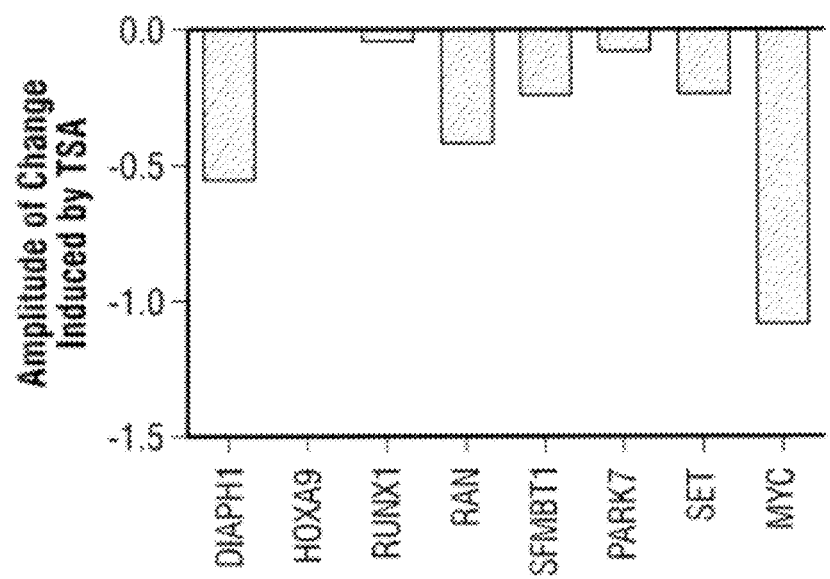
FIGS. 5A, 5B, 5C and 5D show connectivity map results. For each HDAC inhibitor the connectivity map estimated a measure of the extent of differential expression (the amplitude) between a treatment-control pair. In these graphs this amplitude is presented on the Y-axis and the selected proto-oncogenes are depicted on the X-axis. A. TSA, B. SAHA, C. VPA, D. MS-275.
Figure 5B:
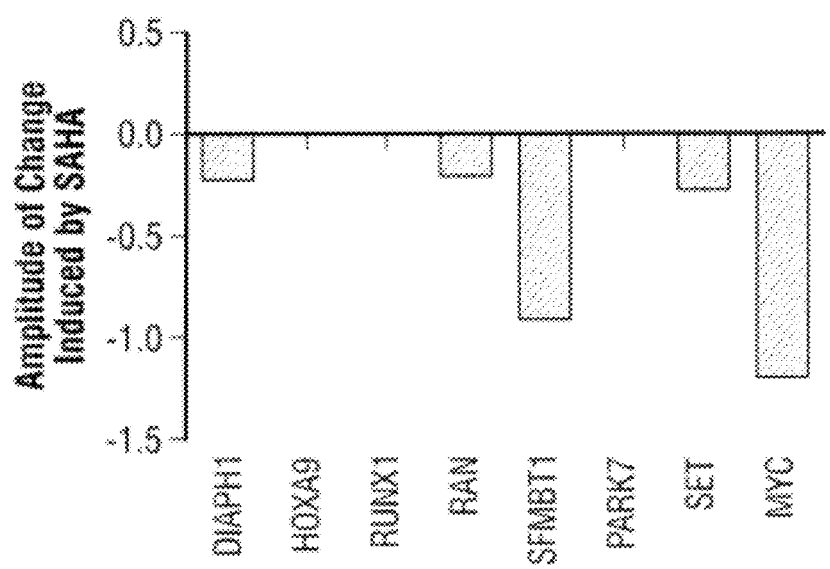
Figure 5C:
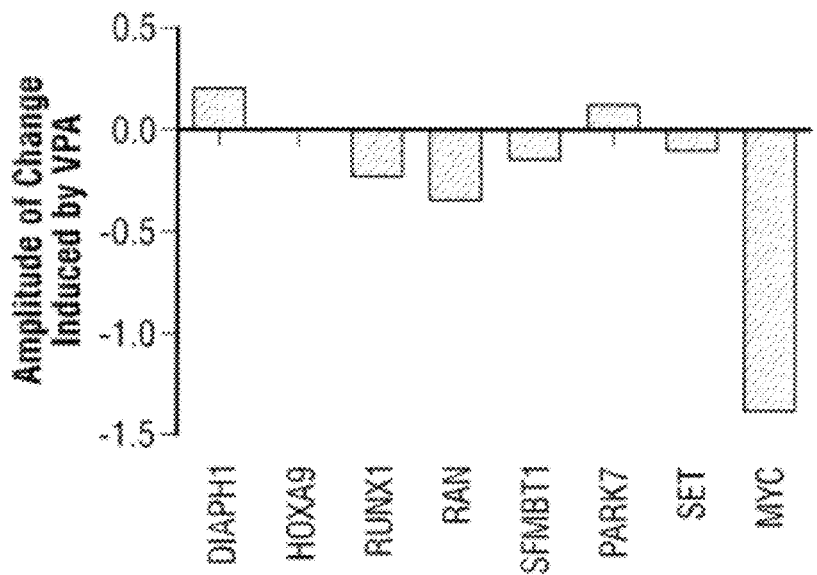
Figure 5D:
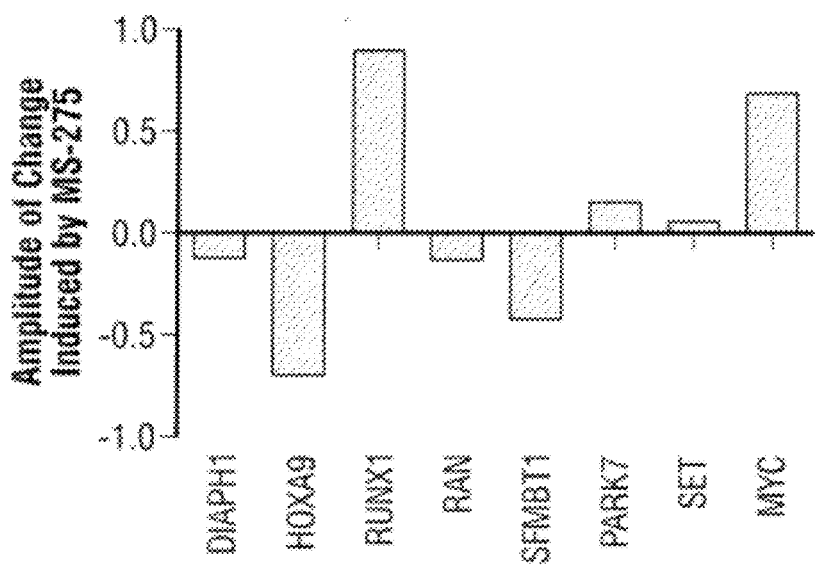
Figure 6A:
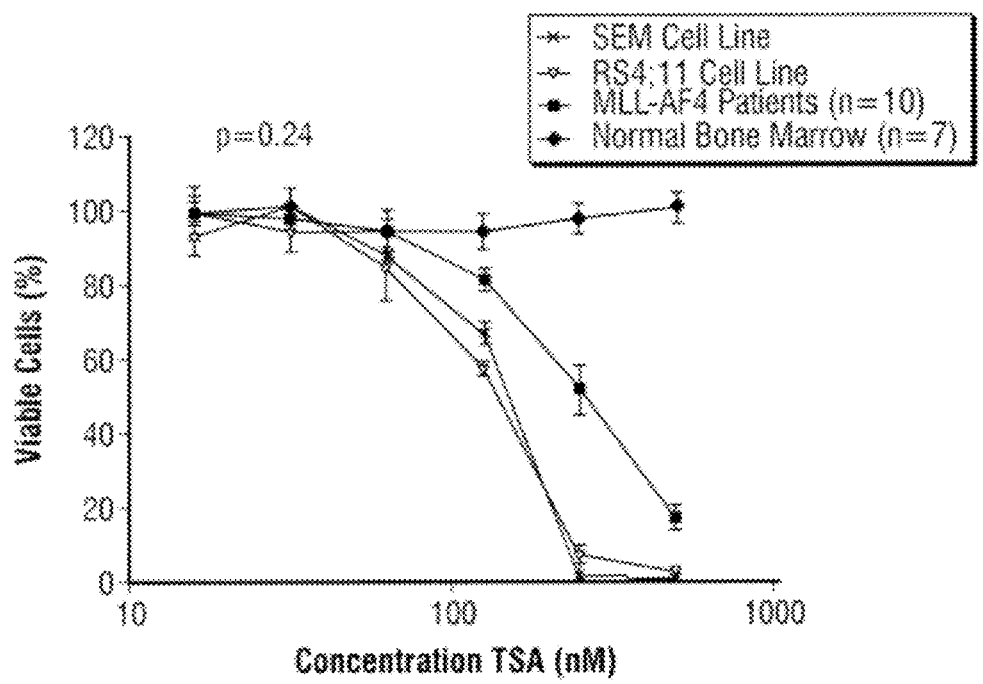
FIGS. 6A, 6B, 6C, 6D and 6E show in vitro cytotoxicity of t(4;11)-positive ALL cells effected by different HDAC inhibitors. Dose-response curves showing the mean in vitro cytotoxic response to HDAC inhibitors in the cell line SEM, the cell line RS4;11, MLL-AF4 patients (n=10) and normal bone marrows (n=7) A. TSA, B. SAHA, C. VPA, D. romidepsin, E. MS-275. Error bars represent standard errors of the mean (SEM). Differences in mean cytotoxicity between patient cells and normal bone marrow cells were statistically analyzed using the Mann-Whitney U test and differences were considered statistically significant at p<0.01.
Figure 6B:
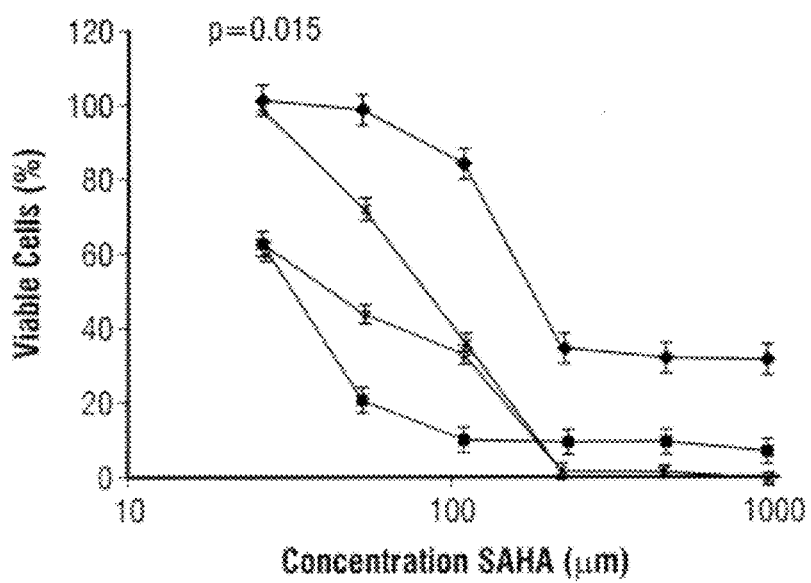
Figure 6C:
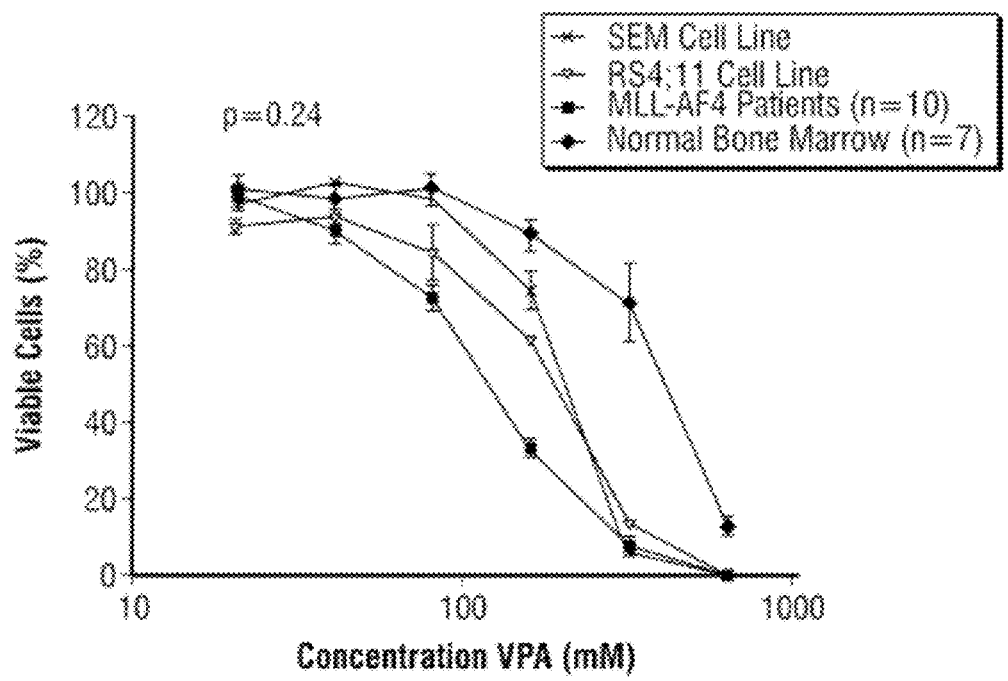
Figure 6D:
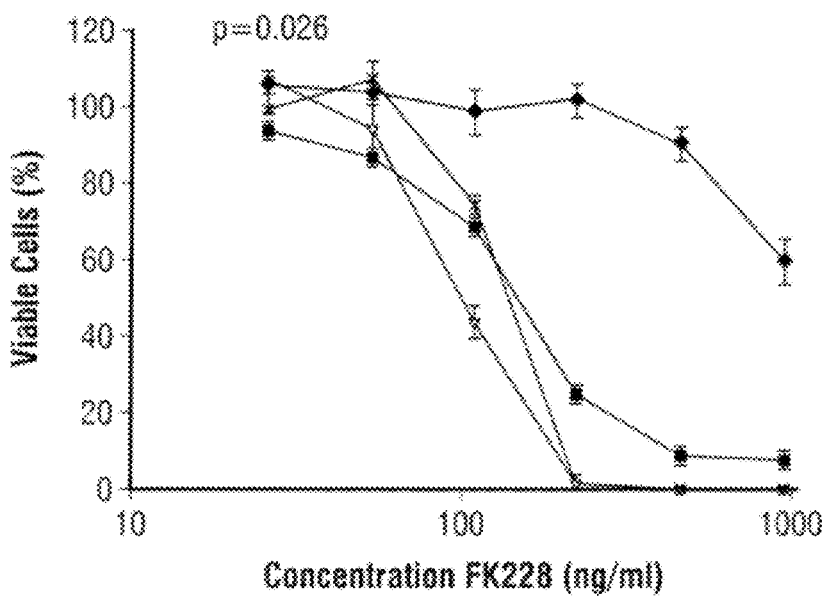
Figure 6E:
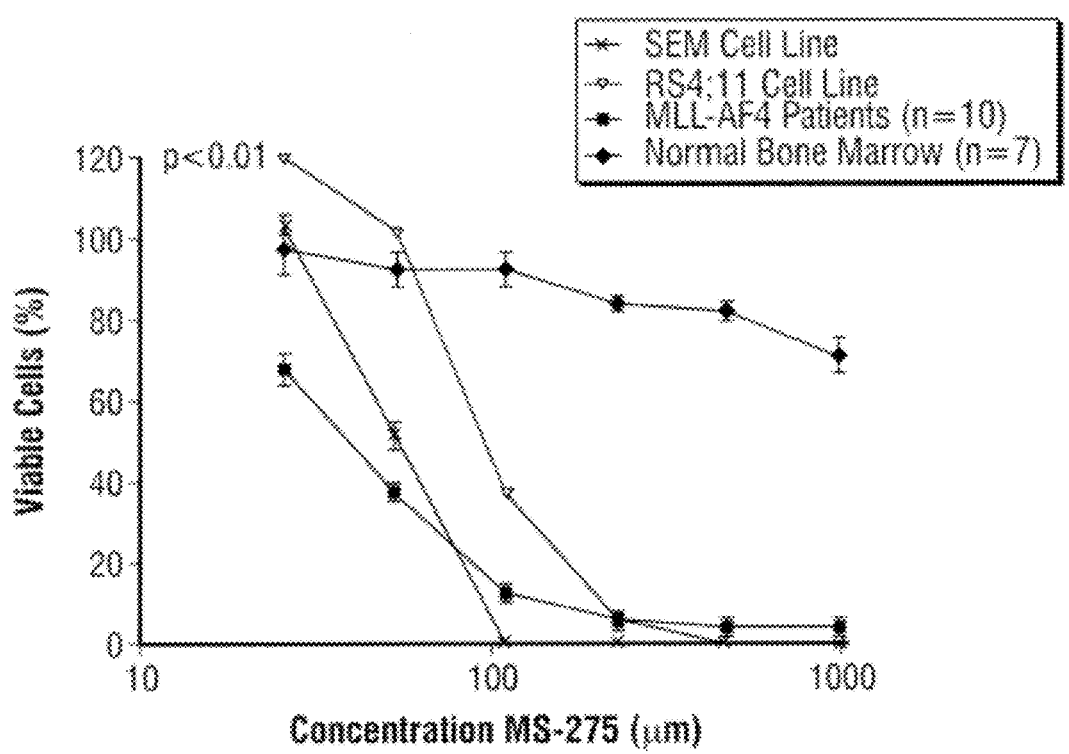

In one embodiment, the DAVID gene ontology database (Dennis et al., *Genome Biol* 4(5):P3, 2003; Huang et al., *Nat Protoc* 4(1):44-57, 2009) is employed. The data is shown in FIG. 2.

In one embodiment, provided herein are methods for detecting hypomethylated proto-oncogenes in a patient's hematological malignancy, comprising: obtaining a biological sample from the patient's hematological malignancy; measuring one or more levels of the hypomethylated proto-oncogenes' mRNA expression, or otherwise identifying the presence of the hypomethylated proto-oncogenes (e.g., Northern blots, polymerase chain reaction (PCR), immunochemistry (IHC) or Western Blot); and comparing said measurement with a control measurement from a patient's hematological malignancy without the hypomethylated proto-oncogenes, wherein a change in the mRNA expression indicates the presence of the hypomethylated proto-oncogenes in said patient's hematological malignancy.

In one embodiment, the expression levels of the selected proto-oncogenes were examined using quantitative real-time PCR analysis. In one embodiment, the tested proto-oncogenes include, but are not limited to, MYC, HOXA9, SET, RUNX1, RAN, PARK7, DIAPHI and SFMBTI.

Cmap analyses can only be performed when both an up-signature and a down-signature are provided. In one embodiment, a probe set for the putative tumor suppressor gene FHIT, that was previously validated to be characteristically down-regulated in MLL-rearranged infant ALL23, represents the "up-signature". The cmap analysis predicted that the compounds potentially suitable for the purpose of down-regulating the hypomethylated genes comprise various HDAC inhibitors. In one embodiment, the test comprised repetitive entries of TSA, SAHA, VPA, and MS-275 (Table 2, FIG. 4). The effects of the tested HDAC inhibitors on the selected proto-oncogenes showed substantial negative amplitudes of gene expression change, reflecting the predicted ability of the tested HDAC inhibitors to down-regulate these genes (FIG. 5).

TABLE 2

| Compound name | Dose | Cell line | Ranking | Down Score |
|---|---|---|---|---|
| trichostatin A | 100 nM | MCF7 | 1 | −0.508 |
| trichostatin A | 100 nM | MCF7 | 2 | −0.438 |
| trichostatin A | 1 μM | PC3 | 3 | −0.434 |
| trichostatin A | 1 μM | MCF7 | 4 | −0.419 |
| trichostatin A | 100 nM | MCF7 | 5 | −0.419 |
| trichostatin A | 100 nM | MCF7 | 7 | −0.414 |
| trichostatin A | 100 nM | MCF7 | 8 | −0.414 |
| trichostatin A | 100 nM | MCF7 | 9 | −0.413 |
| trichostatin A | 100 nM | MCF7 | 10 | −0.408 |
| trichostatin A | 100 nM | MCF7 | 11 | −0.407 |
| trichostatin A | 100 nM | MCF7 | 12 | −0.406 |
| vorinstat | 10 μM | MCF7 | 13 | −0.405 |
| trichostatin A | 100 nM | PC3 | 14 | −0.405 |
| trichostatin A | 1 μM | MCF7 | 16 | −0.399 |
| trichostatin A | 100 nM | MCF7 | 17 | −0.399 |
| trichostatin A | 1 μM | MCF7 | 18 | −0.397 |
| trichostatin A | 100 nM | MCF7 | 20 | −0.392 |
| trichostatin A | 100 nM | HL60 | 21 | −0.39 |
| trichostatin A | 1 μM | MCF7 | 22 | −0.39 |
| trichostatin A | 1 μM | PC3 | 23 | −0.389 |
| trichostatin A | 1 μM | MCF7 | 24 | −0.388 |
| trichostatin A | 1 μM | MCF7 | 25 | −0.386 |
| trichostatin A | 100 nM | PC3 | 26 | −0.386 |
| valproic acid | 10 mM | HL60 | 27 | −0.383 |
| trichostatin A | 1 μM | MCF7 | 29 | −0.381 |
| trichostatin A | 100 nM | MCF7 | 30 | −0.381 |
| trichostatin A | 1 μM | MCF7 | 31 | −0.38 |
| trichostatin A | 1 μM | MCF7 | 32 | −0.378 |
| trichostatin A | 100 nM | HL60 | 33 | −0.377 |
| trichostatin A | 1 μM | MCF7 | 34 | −0.376 |
| valproic acid | 10 mM | MCF7 | 35 | −0.375 |
| trichostatin A | 100 nM | MCF7 | 36 | −0.374 |
| vorinstate | 10 μM | MCF7 | 37 | −0.373 |
| trichostatin A | 100 nM | MCF7 | 38 | −0.372 |
| trichostatin A | 100 nM | MCF7 | 39 | −0.371 |
| trichostatin A | 1 μM | PC3 | 41 | −0.37 |
| trichostatin A | 1 μM | MCF7 | 42 | −0.369 |
| trichostatin A | 100 nM | MCF7 | 43 | −0.368 |
| trichostatin A | 1 μM | PC3 | 44 | −0.367 |
| trichostatin A | 100 nM | MCF7 | 48 | −0.366 |
| trichostatin A | 100 nM | MCF7 | 49 | −0.365 |
| Vorinostat | 10 μM | MCF7 | 51 | −0.364 |
| trichostatin A | 100 nM | MCF7 | 52 | −0.364 |
| trichostatin A | 100 nM | MCF7 | 53 | −0.363 |
| trichostatin A | 100 nM | MCF7 | 54 | −0.363 |
| trichostatin A | 100 nM | MCF7 | 55 | −0.363 |
| trichostatin A | 100 nM | MCF7 | 56 | −0.363 |

TABLE 2-continued

| Compound name | Dose | Cell line | Ranking | Down Score |
|---|---|---|---|---|
| HC toxin | 100 nM | MCF7 | 182 | −0.314 |
| MS-275 | 10 µM | PC3 | 376 | −0.277 |
| MS-275 | 10 µM | PC3 | 474 | −0.267 |

In one embodiment, the hypomethylated genes are down-regulated by the tested HDAC inhibitors. In one embodiment, the expression levels of these genes under the influence of the tested HDAC inhibitors were higher in t(4;11)-positive infant ALL samples (n=10) than in whole pediatric normal bone marrows (n=5) (p<0.01). In one embodiment, these genes were down-regulated in healthy CD19$^+$ B cells. The results are shown in FIG. 8.

In one embodiment, the down-regulation of the tested proto-oncogenes is validated at the mRNA level. In one embodiment, the hypomethylated genes that are validated at the mRNA level are RUNX1, MYC, SET and RAN. In one embodiment, the down-regulation is validated at a protein level. In one embodiment, the hypomethylated genes that are validated at a protein level are RUNX1 and MYC. In one embodiment, the down-regulation is validated at the mRNA and a protein level. In one embodiment, the down-regulated protein is MLL-AF4 fusion protein.

In one embodiment, the repression of aberrantly activated proto-oncogenes by HDAC inhibitors is accompanied by severe and specific induction of cell death (FIG. 6). In one embodiment, the cell is leukemic t(4;11)-positive infant ALL cell. In one embodiment, the activated proto-oncogenes include, but are not limited to MYC, SET, RUNX1 and RAN.

Myelocytomatosis viral oncogene homolog (MYC) has been commonly associated with cell growth and rapid cell proliferation, and is described as a positive regulator of transcription (Meyer et al., *Nat Rev Cancer* 8(12):976-990, 2008).

The RAN gene represents a member of the RAS family of oncogenes. Deregulation of RAN expression facilitates cell transformation and tumor progression (Rensen et al., *Front Biosci* 13:4097-4121, 2008).

SET nuclear oncogene represents a proto-oncogene that functions as a chromatin remodeler and is over-expressed in many tumors (Cervoni et al., *J Biol Chem* 277(28):25026-25031, 2002). Synergistic actions have been described between SET and the N-terminus of MLL (Shimoyama et al., *FEBS LETT* 579(3):757-752, 2005). As the N-terminus of MLL is retained in MLL-AF4 fusion proteins that arise from t(4;11) translocations, SET may be involved in or required for MLL fusion-mediated transcription. C-terminus of wild-type MLL harbors a SET domain, which is lost in MLL fusion proteins. The MLL-AF4 fusion protein requires or recruits SET, and high-level expression of SET is needed for leukemic transformation. SET is also shown as an inhibitor of DNA demethylation (Cervoni, supra). Severely hypermethylated phenotype of t(4;11)-positive infant ALL could in part be due to over-expression of the SET proto-oncogene.

Figure 9:
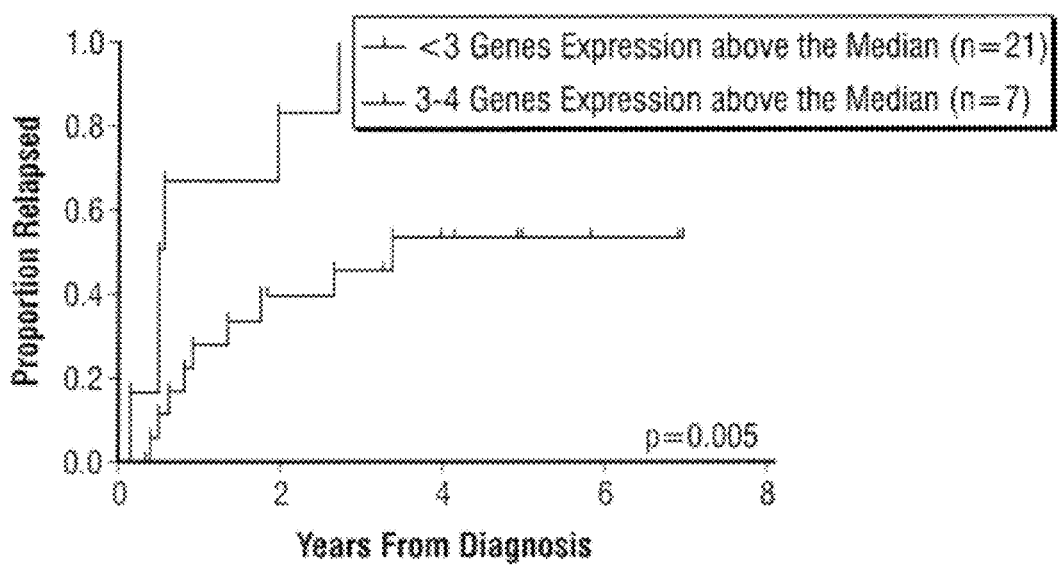
FIG. 9 demonstrates an increased risk of relapse when more proto-oncogenes are highly expressed. Risk of relapse in t(4;11)-positive infant ALL patients (n=28). For each of the proto-oncogenes RAN, RUNXI, MYC and SET the patients were divided into two groups based on the median value of RT-PCR. The risk of relapse was computed for the patients with high expression of 3 or 4 proto-oncogenes (n=7) and patients with high expression of less than 3 proto-oncogenes (n=21) separately. The proportion relapsed, as computed with the Kaplan Meier estimator, is presented on the Y-axis and the time of follow-up (in years) is presented on the X-axis. The log-rank test was used to compare outcomes between different patient groups. SPSS 16.0 statistical software (SPSS Inc., Chicago, Ill., USA) was used for computation of survival statistics.
Figure 10A:
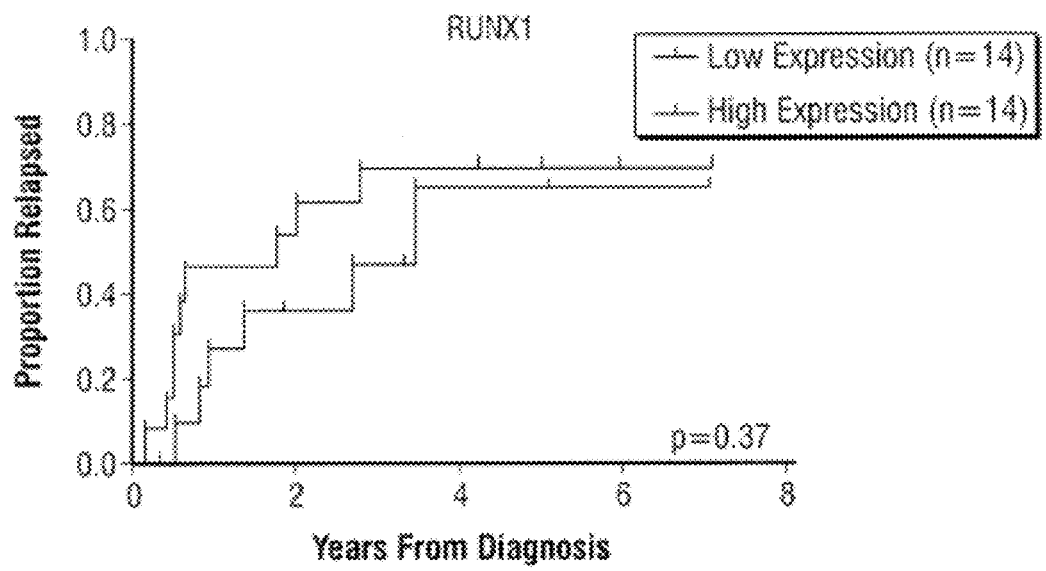
FIGS. 10A, 10B, 10C and 10D show risk of relapse in t(4;11)-positive infant ALL patients (n=28), when patients are divided into 2 groups according to their proto-oncogene mRNA expression levels. For each of the proto-oncogene RAN, RUNX1, MYC, and SET, the patients were divided into two groups based on the median value of RT-PCR. The proportion relapsed is presented on the Y-axis and the time of follow-up (in years) is presented on the X-axis. The risk of relapse was computed with the Kaplan Meier estimator. The log-rank test was used to compare outcomes between different patient groups. SPSS 16.0 statistical software (SPSS Inc., Chicago, Ill., USA) was used for computation of survival statistics. A. RUNX1, B. RAN, C. MYC and D. SET.
Figure 10B:
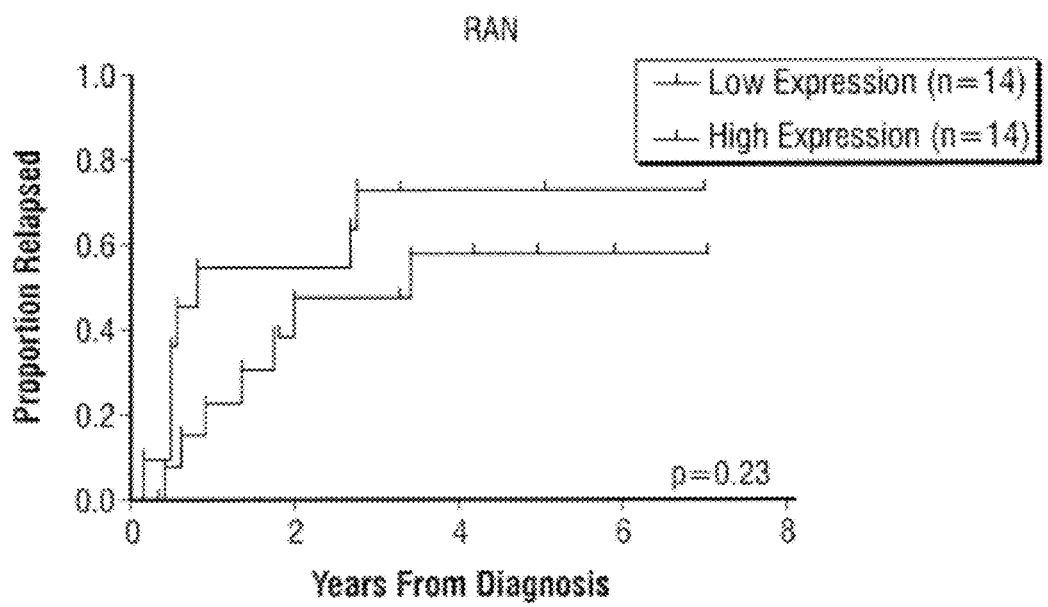
Figure 10C:
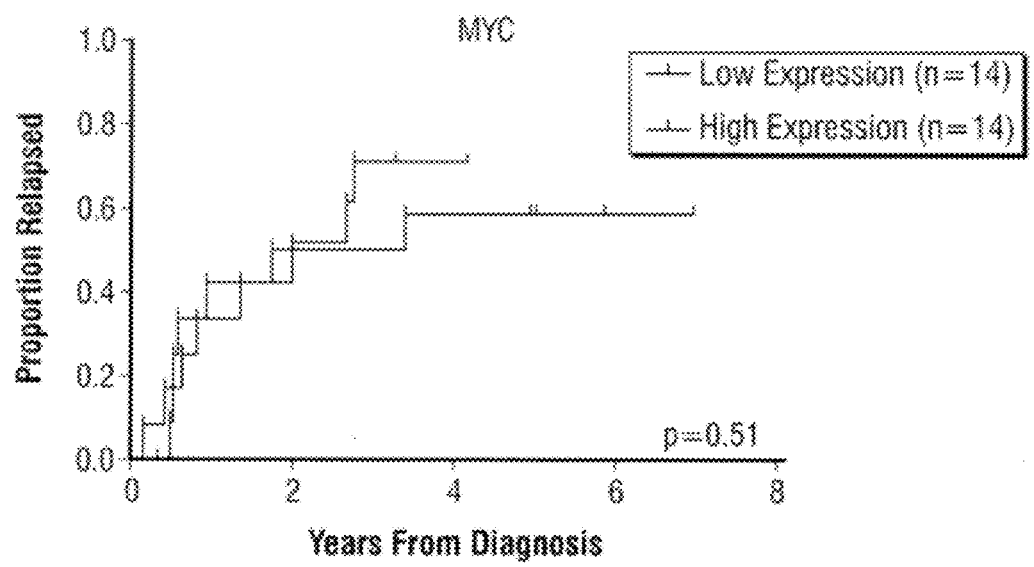
Figure 10D:
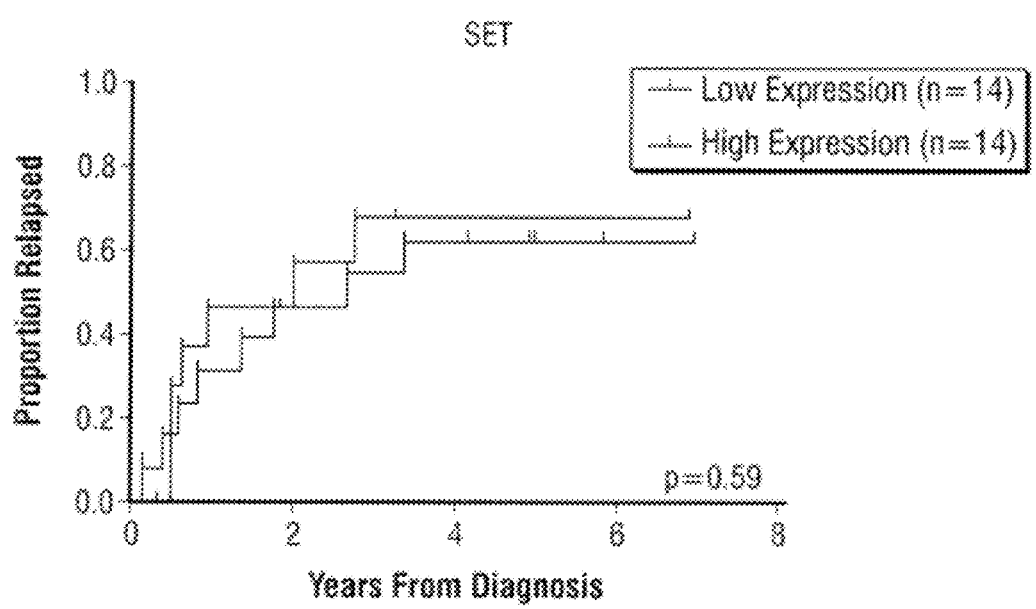

Amplification of Runt-related transcription factor 1 (RUNX1) leads to a poor prognosis in childhood precursor B-cell ALL (Robinson et al., *Leukemia* 17(10:2249-2250, 2003). RUNX1 is required in development during the endothelial to hematopoietic cell transition only and not thereafter (Chen et al., *Nature* 457(7231):887-891, 2009). Accordingly, RUNX1 expression could not be repressed during lymphoid differentiation in t(4;11)-positive infant ALL cells. Full oncogenic transformation by RUNX genes can only be accomplished in close collaboration with genes that rescue cell proliferation, such as MYC (Blyth et al., *Nat Rev Cancer* 5(5):376-387, 2005). The concerted up-regulation of both MYC and RUNX1 proto-oncogenes in t(4;11)-positive infant ALL suggests the phenomenon of "oncogene cooperation" described by Weinberg (Weinberg et al., *Prog Med Virol* 32:115-128, 1985). Activation of the potentially cooperating proto-oncogenes may play an important role in the aggressiveness of t(4;11)-positive leukemia in infants, which is reflected by the increased risk of relapse when more of these hypomethylated proto-oncogenes are highly expressed (FIG. 9).

Methods of Use

In one embodiment, provided herein are methods for predicting the likelihood of a patient having a hematological malignancy, for example MLL-rearranged ALL or MLL-rearranged infant ALL, being responsive to an HDAC inhibitor therapy, based on a gene expression signature of hypomethylated proto-oncogenes, comprising screening said patients hematological malignancy for the presence of the hypomethylated proto-oncogenes, such as MYC, HOXA9, RUNX1, PARK7, RAN or SET, wherein the presence of the hypomethylated proto-oncogenes predicts a likelihood that the HDAC inhibitor will treat said hematological malignancy. In one embodiment, the HDAC inhibitor is romidepsin.

In one embodiment, provided herein are methods for predicting therapeutic efficacy of treatment of a patient having a hematological malignancy, for example MLL-rearranged ALL or MLL-rearranged infant ALL, with an HDAC inhibitor, based on a gene expression signature of hypomethylated proto-oncogenes, comprising screening said patient's hematological malignancy for the presence of the hypomethylated proto-oncogenes, such as MYC, HOXA9, RUNX1, PARK7, RAN or SET, wherein the presence of the hypomethylated proto-oncogenes is predictive of therapeutic efficacy of treatment with the HDAC inhibitor therapy. In one embodiment, the HDAC inhibitor is romidepsin.

In one embodiment, provided is a method for treating a patient suffering from a hematological malignancy by administering an effective amount of HDAC inhibitor.

The hematological malignancies treated by the methods provided herein include, but are not limited to, lymphomas, leukemias, multiple myeloma, plasma cell-derived cancers, relapsed hematological malignancies, and refractory hematological malignancies. In one embodiment, lymphomas that can be treated by the methods provided herein include, but are not limited to, small lymphocytic lymphoma, follicular lymphoma, Mantle cell lymphoma, diffuse large B-cell lymphoma, Burkitt lymphoma, B-cell lymphoblastic lymphoma, small cleaved B-cell lymphoma, non-cleaved B-cell lymphoma, cutaneous T-cell lymphoma (CTCL), and peripheral T-cell lymphoma (PTCL). In one embodiment, leukemias that can be treated by the methods provided herein include, but are not limited to, acute lymphoid leukemia (ALL), chronic lymphocytic leukemia (CLL), acute myeloid leukemia (AML), MLL-rearranged ALL, and MLL-rearranged infant ALL. In one embodiment, the hematological malignancy is MLL-rearranged ALL. In one embodiment, the hematological malignancy is MLL-rearranged infant ALL.

HDAC inhibitors for use in the methods provided herein include, but are not limited to, trichostatin A (TSA). Vorinostat (SAHA), Valproic Acid (VPA), romidepsin and MS-275. In one embodiment, the HDAC inhibitor is romidepsin.

In one embodiment, an HDAC inhibitor is administered intravenously. In one embodiment, an HDAC inhibitor is administered intravenously over a 1-6 hour period. In one embodiment, an HDAC inhibitor is administered intravenously over a 3-4 hour period. In one embodiment, an HDAC inhibitor is administered intravenously over a 5-6 hour period. In one embodiment, an HDAC inhibitor is administered intravenously over a 4 hour period.

In one embodiment, an HDAC inhibitor is administered in a dose ranging from 0.5 mg/m$^2$ to 28 mg/m$^2$. In one embodiment, an HDAC inhibitor is administered in a dose ranging from 0.5 mg/m$^2$ to 5 mg/m$^2$. In one embodiment, an HDAC inhibitor is administered in a dose ranging from 1 mg/m$^2$ to 25 mg/m$^2$. In one embodiment, an HDAC inhibitor is administered in a dose ranging from 1 mg/m$^2$ to 20 mg/m$^2$. In one embodiment, an HDAC inhibitor is administered in a dose ranging from 1 mg/m$^2$ to 15 mg/m$^2$. In one embodiment, an HDAC inhibitor is administered in a dose ranging from 2 mg/m$^2$ to 15 mg/m$^2$. In one embodiment, an HDAC inhibitor is administered in a dose ranging from 2 mg/m$^2$ to 12 mg/m$^2$. In one embodiment, an HDAC inhibitor is administered in a dose ranging from 4 mg/m$^2$ to 12 mg/m$^2$. In one embodiment, an HDAC inhibitor is administered in a dose ranging from 6 mg/m$^2$ to 12 mg/m$^2$. In one embodiment, an HDAC inhibitor is administered in a dose ranging from 8 mg/m$^2$ to 12 mg/m$^2$. In one embodiment, an HDAC inhibitor is administered in a dose ranging from 8 mg/m$^2$ to 10 mg/m$^2$. In one embodiment, an HDAC inhibitor is administered in a dose of about 8 mg/m$^2$. In one embodiment, an HDAC inhibitor is administered in a dose of about 9 mg/m$^2$. In one embodiment, an HDAC inhibitor is administered in a dose of about 10 mg/m$^2$. In one embodiment, an HDAC inhibitor is administered in a dose of about 11 mg/m$^2$. In one embodiment, an HDAC inhibitor is administered in a dose of about 12 mg/m$^2$. In one embodiment, an HDAC inhibitor is administered in a dose of about 13 mg/m$^2$. In one embodiment, an HDAC inhibitor is administered in a dose of about 14 mg/m$^2$. In one embodiment, an HDAC inhibitor is administered in a dose of about 15 mg/m$^2$.

In one embodiment, the HDAC inhibitor is romidepsin. In one embodiment, romidepsin is administered in a dose of 14 mg/m$^2$ over a 4 hour iv infusion on days 1, 8 and 15 of the 28 day cycle. In one embodiment, the cycle is repeated every 28 days.

In one embodiment, increasing doses of an HDAC inhibitor are administered over the course of a cycle. In one embodiment, the dose of about 8 mg/m$^2$ followed by a dose of about 10 mg/m$^2$, followed by a dose of about 12 mg/m$^2$ is administered over a cycle.

In one embodiment, an HDAC inhibitor is administered orally. In one embodiment, an HDAC inhibitor is administered in a dose ranging from 10 mg/m$^2$ to 300 mg/m$^2$. In one embodiment, an HDAC inhibitor is administered in a dose ranging from 15 mg/m$^2$ to 250 mg/m$^2$. In one embodiment, an HDAC inhibitor is administered in a dose ranging from 20 m g/m$^2$ to 200 mg/m$^2$. In one embodiment, an HDAC inhibitor is administered in a dose ranging from 25 mg/m$^2$ to 150 mg/m$^2$. In one embodiment, an HDAC inhibitor is administered in a dose ranging from 25 mg/m$^2$ to 100 mg/m$^2$. In one embodiment, an HDAC inhibitor is administered in a dose ranging from 25 mg/m$^2$ to 75 mg/m$^2$.

In one embodiment, an HDAC inhibitor is administered orally on a daily basis. In one embodiment, an HDAC inhibitor is administered orally every other day. In one embodiment, an HDAC inhibitor is administered orally every third, fourth, fifth, or sixth day. In one embodiment, an HDAC inhibitor is administered orally every week. In one embodiment, an HDAC inhibitor is administered orally every other week.

In one embodiment, provided herein are methods of treating cells ex vivo by contacting the cells with an HDAC inhibitor. In one embodiment, the cell are neoplastic cells. In one embodiment, the neoplastic cells are hematological cells. In one embodiment, provided herein are methods for degrading or inhibiting the growth of or killing cells comprising contacting the cells with an amount of an HDAC inhibitor effective to degrade, inhibit the growth of or kill the cells. In one embodiment, a cytotoxic concentration of an HDAC inhibitor is contacted with the cells in order to kill the cells. In one embodiment, a cytotoxic concentration of an HDAC inhibitor is used to treat the cells.

In one embodiment, provided herein are methods of treating cells in vitro by contacting the cells with an HDAC inhibitor. In one embodiment, the cell are neoplastic cell lines. In one embodiment, the neoplastic cell lines are hematological cell lines. In one embodiment, provided herein are methods for degrading or inhibiting the growth of or killing cells comprising contacting the cell lines with an amount of an HDAC inhibitor effective to degrade, inhibit the growth of or kill the cells. In one embodiment, a cytotoxic concentration of an HDAC inhibitor is contacted with the cell lines in order to kill the cells. In one embodiment, a cytotoxic concentration of an HDAC inhibitor is used to treat the cells.

In one embodiment, the concentration of an HDAC inhibitor ranges from 0.01 nM to 500 nM. In one embodiment, the concentration of an HDAC inhibitor ranges from 0.1 nM to 200 nM. In one embodiment, the concentration of an HDAC inhibitor ranges from 1 nM to 100 nM. In one embodiment, the concentration of an HDAC inhibitor ranges from 1 nM to 50 nM. In one embodiment, the concentration of an HDAC inhibitor ranges from 1 nM to 5 nM.

Any type of cell may be treated or killed with an HDAC therapy. The cells may be derived from any animal, plant, bacterial or fungal source. The cells may be at any stage of development or differentiation. In one embodiment, the cells are animal cells. In one embodiment, the cells are vertebrate cells. In one embodiment, the cells are mammalian cells. In one embodiment, the cells are human cells. The cells may derived from a male or female human at any stage of development.

The cells may be wild type or mutant cells. The cells may be genetically engineered. In one embodiment, the cells are normal cells. In one embodiment, the cells are hematological cells. In one embodiment, the cells are white blood cells. In one embodiment, the cells are precursors of white blood cells (e.g., stem cells, progenitor cells, blast cells). In one embodiment, the cells are neoplastic cells. In one embodiment, the cells are cancer cells. In one embodiment, the cells are derived from hematological malignancy. In one embodiment, the cells are derived from a blood sample from the subject or from a bone marrow biopsy. In one embodiment, the cells are derived from a lymph node biopsy. In one embodiment, such testing is useful in determining whether a patient's response will be positive to a particular therapy. In one embodiment, such testing is useful in determining the dosage needed to treat the malignancy. In one embodiment, the testing of susceptibility of a patient's cancer cells to an HDAC inhibitor prevents the unnecessary administration of drugs with no effect to the patient.

In one embodiment, the cells are derived from cancerous cell lines. In one embodiment, the cells derived from hematological malignancies. In one embodiment, the hematological malignancy is human MLL-rearranged ALL. In one embodiment, the hematological malignancy is human MLL-rearranged infant ALL. In one embodiment, human MLL-rearranged infant ALL cell lines include, but are not limited to, SEM and RS4:11.

Various markers may be assayed for in the cells treated with an HDAC inhibitor. In one embodiment, the marker Annexin Y is used to identify cells undergoing apoptosis. In one embodiment, an HDAC inhibitor is used to induce cell death as evidenced by percentage of cell viability.

Proto-oncogenes have been shown to be repressed by HDAC inhibitors. Proto-oncogenes may be assayed to include MYC, SET, RUNX1 and RAN proto-oncogenes. In one embodiment, cells are treated with an amount of an HDAC inhibitor effective to repress the activated proto-oncogenes. In one embodiment, an HDAC inhibitor is used to repress the activated proto-oncogene expression in cells.

Combination Therapy

In one embodiment, provided herein are methods for predicting the likelihood of a patient having a hematological malignancy, for example MLL-rearranged ALL or MLL-rearranged infant ALL, being responsive to a combination therapy of an HDAC inhibitor and a DNA demethylating agent, based on a gene expression signature of hypomethylated proto-oncogenes, comprising screening said patient's hematological malignancy for the presence of the hypomethylated proto-oncogenes, such as MYC, HOXA9, RUNX1, PARK7, RAN or SET, wherein the presence of the hypomethylated proto-oncogenes predicts a likelihood that the combination of the HDAC inhibitor and the DNA demethylating agent will treat said hematological malignancy. In one embodiment, the HDAC inhibitor is romidepsin. In one embodiment, the DNA demethylating agent is 5-azacytidine.

In one embodiment, provided herein are methods for predicting therapeutic efficacy of treatment of a patient having a hematological malignancy, for example MLL-rearranged ALL or MLL-rearranged infant ALL, with a combination of an HDAC inhibitor and a DNA demethylating agent, comprising screening said patient's hematological malignancy based on a gene expression signature of hypomethylated proto-oncogenes, such as MYC, HOXA9, RUNX1, PARK7, RAN or SET, wherein the presence of the hypomethylated proto-oncogenes is predictive of therapeutic efficacy of the combination of the HDAC inhibitor and the DNA demethylating agent. In one embodiment, the HDAC inhibitor is romidepsin. In one embodiment, the DNA demethylating agent is 5-azacytidine.

In one embodiment, provided is a method for treating a patient suffering from a hematological malignancy by administering an effective amount of HDAC inhibitor and an additional therapeutic agent. In one embodiment, the HDAC inhibitor is romidepsin. In one embodiment, the additional therapeutic agent is a DNA demethylating agent.

The hematological malignancies treated by the methods provided herein include, but are not limited to, lymphomas, leukemias, multiple myeloma, plasma cell-derived cancers, relapsed hematological malignancies, and refractory hematological malignancies. In one embodiment, lymphomas that can be treated by the methods provided herein include, but are not limited to, small lymphocytic lymphoma, follicular lymphoma, Mantle cell lymphoma, diffuse large B-cell lymphoma, Burkitt lymphoma, B-cell lymphoblastic lymphoma, small cleaved B-cell lymphoma, non-cleaved B-cell lymphoma, cutaneous T-cell lymphoma (CTCL), and peripheral T-cell lymphoma (PTCL). In one embodiment, leukemias that can be treated by the methods provided herein include, but are not limited to, acute lymphoid leukemia (ALL), chronic lymphocytic leukemia (CLL), acute myeloid leukemia (AML), MLL-rearranged ALL, and MLL-rearranged infant ALL. In one embodiment, the hematological malignancy is MLL-rearranged ALL. In one embodiment, the hematological malignancy is MLL-rearranged infant ALL.

HDAC inhibitors for use in the methods provided herein include, but are not limited to, trichostatin A (TSA), Vorinostat (SAHA), Valproic Acid (VPA), romidepsin and MS-275. In one embodiment, the HDAC inhibitor is romidepsin.

DNA demethylating agents for use in the methods provided herein include, but are not limited to, 5-azacytidine (azacytidine), 5-azadeoxycytidine (decitabine), zebularine and procaine. In one embodiment, the DNA demethylating agent is 5-azacytidine, decitabine or zebularine. In one embodiment, the DNA demethylating agent is 5-azacytidine. A DNA demethylating agent may be administered concurrently with, subsequent to or prior to an HDAC inhibitor.

In one embodiment, a combination of an HDAC inhibitor and a DNA demethylating agent is administered intravenously. In one embodiment, the combination administered intravenously over a 1-6 hour period. In one embodiment, the combination is administered intravenously over a 3-4 hour period. In one embodiment, the combination is administered intravenously over a 5-6 hour period. In one embodiment, the combination is administered intravenously over a 4 hour period.

In one embodiment, the combination is administered in a dose ranging from 0.5 mg/m$^2$ to 28 mg/m$^2$. In one embodiment, the combination is administered in a dose ranging from 0.5 mg/m$^2$ to 5 mg/m$^2$. In one embodiment, the combination is administered in a dose ranging from 1 mg/m$^2$ to 25 mg/m$^2$. In one embodiment, the combination is administered in a dose ranging from 1 mg/m$^2$ to 20 mg/m$^2$. In one embodiment, the combination is administered in a dose ranging from 1 mg/m$^2$ to 15 mg/m$^2$. In one embodiment, the combination is administered in a dose ranging from 2 mg/m$^2$ to 15 mg/m$^2$. In one embodiment the combination is administered in a dose ranging from 2 mg/m$^2$ to 12 mg/m$^2$. In one embodiment, the combination is administered in a dose ranging from 4 mg/m$^2$ to 12 mg/m$^2$. In one embodiment, the combination is administered in a dose ranging from 6 mg/m$^2$ to 12 mg/m$^2$. In one embodiment, the combination is administered in a dose ranging from 8 mg/m$^2$ to 12 mg/m$^2$. In one embodiment, the combination is administered in a dose ranging from 8 mg/m$^2$ to 10 mg/m$^2$.

In one embodiment, the combination with increasing doses of an HDAC inhibitor is administered over the course of a cycle. In one embodiment, the dose of about 8 mg/m$^2$ followed by a dose of about 10 mg/m$^2$, followed by a dose of about 12 mg/m$^2$ of an HDAC inhibitor is administered over a cycle.

In one embodiment, the combination is administered orally. In one embodiment, the combination is administered in a dose ranging from 10 mg/m$^2$ to 300 mg/m$^2$. In one embodiment, the combination is administered in a dose ranging from 15 mg/m$^2$ to 250 mg/m$^2$. In one embodiment, the combination is administered in a dose ranging from 20 mg/m$^2$ to 200 mg/m$^2$. In one embodiment, the combination is administered in a dose ranging from 25 mg/m$^2$ to 150 mg/m$^2$. In one embodiment, the combination is administered in a dose ranging from 25 mg/m$^2$ to 100 mg/m$^2$. In one embodiment, the combination is administered in a dose ranging from 25 mg/m$^2$ to 75 mg/m$^2$.

In one embodiment, the combination is administered orally on a daily basis. In one embodiment, the combination is administered orally every other day. In one embodiment, the combination is administered orally every third, fourth, fifth, or sixth day. In one embodiment, the combination is administered orally every week. In one embodiment, the combination is administered orally every other week.

In one embodiment, provided herein are methods of treating cells ex vivo by contacting the cells with a combination of an HDAC inhibitor and a DNA demethylating agent. In one embodiment, the cell are neoplastic cells. In one embodiment, the neoplastic cells are hematological cells. In one embodiment, provided herein are methods for degrading or inhibiting the growth of or killing cells comprising contacting the cells with an amount of the combination effective to degrade, inhibit the growth of or kill the cells. In one embodiment, a cytotoxic concentration of the combination is contacted with the cells in order to kill the cells. In one embodiment, a cytotoxic concentration of the combination is used to treat the cells.

In one embodiment, provided herein are methods of treating cells in vitro by contacting the cells with a combination of an HDAC inhibitor and a DNA demethylating agent. In one embodiment, the cell are neoplastic cell lines. In one embodiment, the neoplastic cell lines are hematological cell lines. In one embodiment, provided herein are methods for degrading or inhibiting the growth of or killing cells comprising contacting the cell lines with an amount of the combination effective to degrade, inhibit the growth of or kill the cells. In one embodiment, a cytotoxic concentration of the combination is contacted with the cell lines in order to kill the cells. In one embodiment, a cytotoxic concentration of the combination is used to treat the cells.

In one embodiment, the combination of agents acts additively to kill the cells. In one embodiment, the combination of agents acts synergistically to kill the cells. In one embodiment, a lower concentration of one or both agents is needed to kill the cells than would be needed if either agent were used alone.

In one embodiment, the concentration an HDAC inhibitor in the combination ranges from 0.01 nM to 500 nM. In one embodiment, the concentration of an HDAC inhibitor in the combination ranges from 0.1 nM to 200 nM. In one embodiment, the concentration of an HDAC inhibitor in the combination ranges from 1 nM to 100 nM. In one embodiment, the concentration of an HDAC inhibitor in the combination ranges from 1 nM to 50 nM. In one embodiment, the concentration of an HDAC inhibitor in the combination ranges from 1 nM to 5 nM.

In one embodiment, the concentration of a DNA demethylating agent in the combination ranges from 1 µM to 500 µM. In one embodiment, the concentration of a DNA demethylating agent in the combination ranges from 10 µM to 400 µM. In one embodiment, the concentration of a DNA demethylating agent in the combination ranges from 50 µM to 300 µM. In one embodiment, the concentration of a DNA demethylating agent in the combination ranges from 100 µM to 250 µM. In one embodiment, the concentration of a DNA demethylating agent in the combination ranges from 150 µM to 200 µM.

In one embodiment, the cells are derived from cancerous cell lines. In one embodiment, the cells derived from hematological malignancies. In one embodiment, the hematological malignancy is human MLL-rearranged ALL. In one embodiment, the hematological malignancy is human MLL-rearranged infant ALL. In one embodiment, human MLL-rearranged infant ALL cell lines include, but are not limited to, SEM and RS4:11.

In one embodiment, the combination of an HDAC inhibitor and a DNA demethylating agent is used to induce cell death as evidenced by percentage of cell viability. In one embodiment, the combination is used to repress expression of proto-oncogenes in cells. In one embodiment, the combination is used to degrade the MLL-AF4 fusion protein. The modulation of cellular activity by the combination may be used for research or clinical purposes.

Compositions

Each of the compounds described herein is used as a composition when combined with an acceptable carrier or excipient. Such compositions are useful in the in vitro methods provided herein, or for administration to a subject in vivo, or in the ex vivo methods provided herein.

Provided herein are pharmaceutical compositions comprising a compound provided herein, e.g., a compound of Formulas I-V', as an active ingredient, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug; in combination with a pharmaceutically acceptable vehicle, carrier, diluent, or excipient, or a mixture thereof.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient. In one embodiment, lactose-free compositions comprise an active ingredient provided herein, a binder/filler, and a lubricant. In another embodiment, lactose-free dosage forms comprise an active ingredient, microcrystalline cellulose, pre-gelatinized starch, and magnesium stearate.

The compound provided herein may be administered alone, or in combination with one or more other compounds provided herein. The pharmaceutical compositions that comprise a compound provided herein, e.g., a compound of Formulas I-V', can be formulated in various dosage forms for oral and parenteral administration.

In one embodiment, the pharmaceutical compositions are provided in a dosage form for oral administration, which comprise a compound provided herein, e.g., a compound of Formulas I-V', including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and one or more pharmaceutically acceptable excipients or carriers.

In another embodiment, the pharmaceutical compositions are provided in a dosage form for parenteral administration, which comprise a compound provided herein, e.g., a compound of Formula I-V', including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone.

Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfate, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Romidepsin Formulation

In one embodiment, romidepsin is formulated for injection as a sterile lyophilized white powder and is supplied in a single-use vial containing 10 mg romidepsin and 20 mg povidone, USP. The diluent is a sterile clear solution and is supplied in a single-use vial containing a 2 ml deliverable volume. The diluent for romidepsin contains 80% (v/v) propylene glycol, USP and 20% (v/v) dehydrated alcohol, USP. Romidepsin is supplied as a kit containing two vials.

Romidepsin for injection is intended for intravenous infusion after reconstitution with the supplied Diluent and after further dilution with 0.9% Sodium Chloride, USP.

Kits

In one embodiment, provided herein are kits comprising one or more containers filled with an HDAC inhibitor or a pharmaceutical composition thereof, reagents for detecting hypomethylated proto-oncogenes, such as MYC, HOXA9, RUNX1, PARK7, RAN or SET, in a patient having MLL-rearranged ALL or MLL-rearranged infant ALL or in cancer cells, wherein cancer cells are MLL-rearranged ALL or MLL-rearranged infant ALL cancer cells, and instructions for detecting these hypomethylated proto-oncogenes in a patient having MLL-rearranged ALL or MLL-rearranged infant ALL, or in cancer cells, wherein cancer cells are MLL-rearranged ALL or MLL-rearranged infant ALL cancer cells. In one embodiment, the HDAC inhibitor is romidepsin.

In one embodiment, provided herein are kits comprising one or more containers filled with a combination of an HDAC inhibitor and a DNA demethylating agent or a pharmaceutical composition thereof, reagents for detecting hypomethylated proto-oncogenes, such as MYC, HOXA9, RUNX1, PARK7, RAN or SET, in a patient having MLL-rearranged ALL or MLL-rearranged infant ALL or in cancer cells, wherein cancer cells are MLL-rearranged ALL or MLL-rearranged infant ALL cancer cells, and instructions for detecting these hypomethylated proto-oncogenes in a patient having MLL-rearranged ALL or MLL-rearranged infant ALL, or in cancer cells, wherein cancer cells are MLL-rearranged ALL or MLL-rearranged infant ALL cancer cells. In one embodiment, the HDAC inhibitor is romidepsin. In one embodiment, the DNA demethylating agent is 5-azacytidine, decitabine or zebularine. In one embodiment, the DNA demethylating agent is 5-azacytidine.

EXAMPLES

Example 1

Patient Samples 15 newly diagnosed t(4;11)-positive infant ALL patients enrolled in the international collaborative INTERFANT-99 treatment protocol were studied. Patient characteristics are listed in Table 3. Whole normal bone marrow samples obtained from seven non-leukemic children (including one infant) were used as controls. Approval for these studies was obtained from the Erasmus MC Institutional Review Board, and informed consent was obtained from parents or legal guardians according to the Declaration of Helsinki. Leukemic cell isolation and enrichment to achieve more than 90% leukemic blasts in each sample, as well as DNA and RNA extractions were performed as described in Stam (Stam et al. *Blood* 106(7):2484-2490, 2005).

TABLE 3

| Patient number | Age (months) | Sex | Type of MLL translocation | Immunophenotype |
|---|---|---|---|---|
| 1 | 9.4 | Female | t(4; 11) | pro-B |
| 2 | 2.8 | Male | t(4; 11) | pro-B |
| 3 | 9.4 | Female | t(4; 11) | pro-B |
| 4 | 11.0 | Female | t(4; 11) | pre-B |
| 5 | 3.6 | Male | t(4; 11) | pro-B |
| 6 | 6.6 | Female | t(4; 11) | pro-B |
| 7 | 1.9 | Male | t(4; 11) | pro-B |
| 8 | 4.2 | Female | t(4; 11) | pro-B |
| 9 | 0.6 | Female | t(4; 11) | pro-B |
| 10 | 0.7 | Female | t(4; 11) | pro-B |
| 11 | 1.9 | Female | t(4; 11) | pro-B |
| 12 | 6.4 | Female | t(4; 11) | Pre-B |
| 13 | 6.4 | Male | t(4; 11) | Pro-B |
| 14 | 1.6 | Female | t(4; 11) | Pro-B |
| 15 | 8.0 | Male | t(4; 11) | Pro-B |

Example 2 t(4;11)-Positive ALL Cell Line Models

The cell lines SEM and RS4;11 representing t(4;11)-positive precursor B-cell ALL cell lines were purchased from DSMZ (Braunschweig, Germany). SEM cell line was originally derived from a 5-year-old girl during relapse (Pocock et al., *Br J Haematol* 90(4):855-867, 1995) and RS4;11 cell line was established from the bone marrow of a 32 year-old woman (Strong et al., *Blood* 65(1):21-31, 1985). The cell lines were maintained as suspension cultures in RPMI 1640 with L-Alanyl-L-Glutamine (Invitrogen) supplemented with 10% FCS (Integra), 100 IU/ml penicillin, 100 pg/ml streptomycin, and 0.125 pg/ml fungizone (Invitrogen) at 37° C. in humidified air containing 5% CO2.

Example 3

Differential Methylation Hybridization Using CpG Island Microarrays

Methylation-sensitive restriction enzyme-based Differential Methylation Hybridization (DMH) was performed using 500 ng of input DNA as described in Stumpel et al, supra). The common reference for all samples was a commercially available genomic DNA pool derived from five healthy males and five healthy females (Promega Benelux BV, Leiden, the Netherlands). DMH was applied on the first commercially available genome-wide CpG island microarrays (Agilent Technologies, Santa Clara, USA). These high-resolution microarrays contain 243.497 60-mer oligonucleotide probes, including 67.487 CpG island probes located in or near gene promoters. The analyses were limited to these promoter-specific probes. Raw genome-wide DNA methylation data has been deposited in the NCBI Gene Expression Omnibus (Edgar et al., *Nucleic Acids Res* 30(1):207-210, 2002) under the GEO Series accession number GSE 18400. Normalization of the CpG island microarray data and identification of differentially methylated CpG islands were performed as described in Stupmel et al, supra. A p-value<0.01 corrected for multiple testing by the false discovery rate (FDR) step-up procedure of Benjamini & Hochberg (Bennjamini, *J Roy Stat Soc B* 57(1):289-300, 1995) was regarded significant. The analyses were carried out in the statistical environment R using Bioconductor packages (R Development Core Team, 2007). Heatmaps were generated in GenePattern version 3.1.2 (Reich et al. *Nat Genet* 38(5):500-501, 2006). For genes most significantly hypomethylated in t(4;11)-positive infant ALL corresponding probe sets in Affymetrix gene expression data were gathered.

Example 4

Gene Expression Profiling Using Affymetrix GeneChips

Gene expression profiles were generated for t(4;11)-positive infant ALL cases (n=15) and healthy pediatric bone marrow samples (n=7), using the same samples for which DNA methylation profiles were produced. For examination of gene expression, high-quality RNA was reverse transcribed using T7-linked oligo-dT primers, and the obtained cDNA was used as a template to synthesize biotinylated cRNA. Labeled cRNA was then fragmented and hybridized to HU133plus2.0 GeneChips (Affymetrix, Santa Clara, Calif., USA) according to the manufacturer's guidelines. The infant ALL gene expression data was deposited in the NCBI Gene Expression Omnibus under the GEO Series accession number GSE 19475. Array processing and statistical analyses were conducted as described in Stam et al., *Blood* 115(4):2835-2844, 2010 and Stumple et al., supra.

Example 5

Quantitative Real-Time PCR Analysis

Total RNA was reverse transcribed and the obtained cDNA was used to quantify mRNA expression by using quantitative real-time PCR analysis as described in Stam et al., *Haematologica* 92(11):1565-1568, 2007). All oligonucleotides were designed using the OLIGO 6.22 software (Molecular Biology Insights, Cascade, Calif.). Primer combinations used for transcript amplification of selected target genes, as well as the housekeeping reference gene B2M (encoding human beta-2-Microglobulin), are listed in Table 4. PCR products were amplified using the DyNAmo SYBR Green qPCR kit (Finnzymes, Espoo, Finland) according to the manufacturer's recommendations, using SYBR Green as a fluorophore to detect amplified transcripts. Per experiment, samples were analyzed in duplicate and all experiments were conducted twice. Apart from RNA extracted from healthy pediatric bone marrows, commercially available RNA from normal $CD19^+$ B-cells (Miltenyi Biotec GmbH, Bergisch Gladbach, Germany) was used as an additional control sample for $CD19^+$ B-ALL cells.

Quantitative real-time PCR analysis was used to determine the expression levels of the selected proto-oncogenes including MYC, HOXA9, SET, RUNX1, RAN, PARK7, DIAPHI and SFMBTI relative to the reference gene B2M. The expression of all of these genes was significantly higher in t(4;11)-positive infant ALL samples (n=10) than in whole pediatric normal bone marrows (n=5) (p<0.01) (FIG. 8). These genes were also down-regulated in healthy CD $19^+$ B cells. The SFMBTI gene appeared to be highly expressed in normal CD $19^+$ B cells despite downregulation in whole bone marrow samples (FIG. 8). The SFMBTI was excluded from further analyses.

TABLE 4

| Target gene | Sequence |
|---|---|
| DIAPH1 | |
| Forward | 5'-ATCCCACAGCACAGTCAT-3' |
| Reverse | 5'-GGGTTGTTGTTGAGAGACA-3' |
| SFM8T1 | |
| Forward | 5'-GAGCTGCCTCAATGTGTAG-3' |
| Reverse | 5'-GACAGCATTCCAGTTTGATAC-5' |
| RAN | |
| Forward | 5'-TGGCAACAAAGTGGATATTA-3' |
| Reverse | 5'-CGGGAGAGCAGTTGTCT-3' |
| PARK7 | |
| Forward | 5'-GTTCGCTCTAAACAAAACAGT-3' |
| Reverse | 5'-TAGGCTGAGAAATCTCTGTGT-3' |
| HOXA9'9 | |
| Forward | 5'-CACGCTTGACACTCACACT-3' |
| Reverse | 5'-CAGGGTCTGGTGTTTTGTA-3' |

TABLE 4-continued

| Target gene | Sequence |
|---|---|
| MYC | |
| Forward | 5'-CGTCCTCGGATTCTC-3' |
| Reverse | 5'-GCTGCGTAGTTGTGCTG-3' |
| SEro | |
| Forward | 5'-TTCCCGATATGGATGATG-3' |
| Reverse | 5'-CCCCCCAAATAAATTGAG-3' |
| RUNX1 | |
| Forward | 5'-GACAGCCCCACCTTCC-3' |
| Reverse | 5'-CCACTTCGACCGACAA-3' |
| MLL-AF4 | |
| Forward | 5'-GGACCGCCAAGAAAAG-3' |
| Reverse | 3'-CTGGGGTTTGTTCACTGT-3' |
| 82M" | |
| Forward | 5'-GGAGCATTCAGACTTGTTT-3' |
| Reverse | 5'-ATGCGGCATCTTCAAA-3' |

Example 6

Western Blotting

Western blotting was performed as described in Stam et al, supra. Antibodies used were mouse monoclonal anti-c-MYC (Merck, Darmstadt, Germany, #0P30), rabbit polyclonal anti-RUNX1 (Cell Signaling Technology Inc., Danvers, Mass., #4334) and rabbit polyclonal anti-RAN (Cell Signaling Technology Inc., Danvers, Mass., #4462). Mouse monoclonal anti-SET was provided by Professor Nagata (Tsukuba, Japan). An anti-ACTIN mouse monoclonal antibody (Sigma-Aldrich, St. Louis, Mo., #A2547) was used as a loading control. Whole cell protein lysates containing 25 µg of protein were resolved on 10% polyacrylamide gels topped with 4% stacking gels, and subsequently transferred to nitrocellulose membranes (Schleichler & Schuell, Dassel, Germany). The membranes were probed with primary monoclonal and polyclonal antibodies. After incubation with respective secondary antibodies conjugated with horseradish peroxidase (DAKO, Glostrup, Denmark), the proteins were visualized using SuperSignal® West Femto chemiluminescent substrate (Thermo Fisher Scientific, Rockford, Ill.).

Example 7

In Vitro Drug Cytotoxicity Assay with HDAC Inhibitors

To determine in vitro cytotoxicity of various HDAC inhibitors, SEM and RS4;11 cell lines were cultured in the presence of different concentrations of HDAC inhibitors using 4-day MTT assay. The concentrations used corresponded to those initially applied to establish the Connectivity Map: Trichostatin A (TSA) (1 µM), Vorinostat (SAHA) (10 µM), Valproic Acid (VPA) (10 mM), Romidepsin (10 ng/ml) and MS-275 (10 µM). Cells were sampled after 6, 24 and 48 hours of exposure and cell viability was assessed using the trypan blue dye exclusion method.

The results (FIG. 6) demonstrated that the HDAC inhibitors in the tested concentrations showed a high therapeutic index and a preferred specificity towards targeting t(4;11)- positive ALL cells, especially in case of TSA, romidepsin and MS-275. TSA demonstrated consistent eradication of the entire leukemic cell population at concentrations that were harmless for healthy hematopoietic bone marrow cells.

Example 8

Figure 7A:
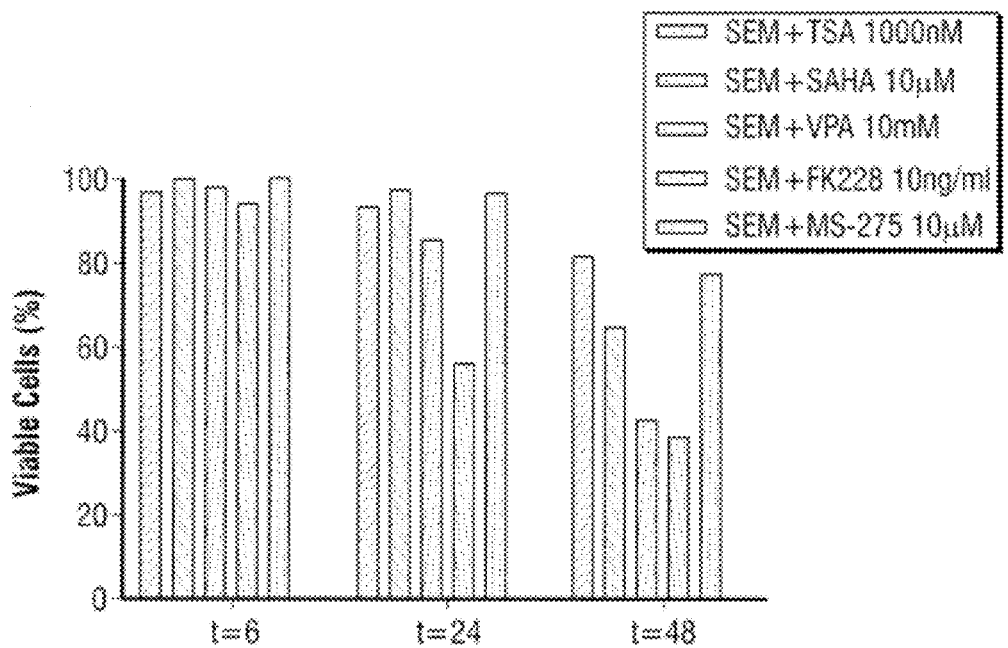
FIGS. 7A and 7B show cell viability counts. The percentage of cell viability as measured by trypan blue exclusion is presented at three time points (after 6 hours, 24 hours and 48 hours) for the different exposures to the HDAC inhibitors: TSA (1 mM), SAHA (10 µM), VPA (10 mM), romidepsin (10 ng/ml) and MS-275 (10 µM). A. SEM cell line, B. RS4;11 cell line.
Figure 7B:
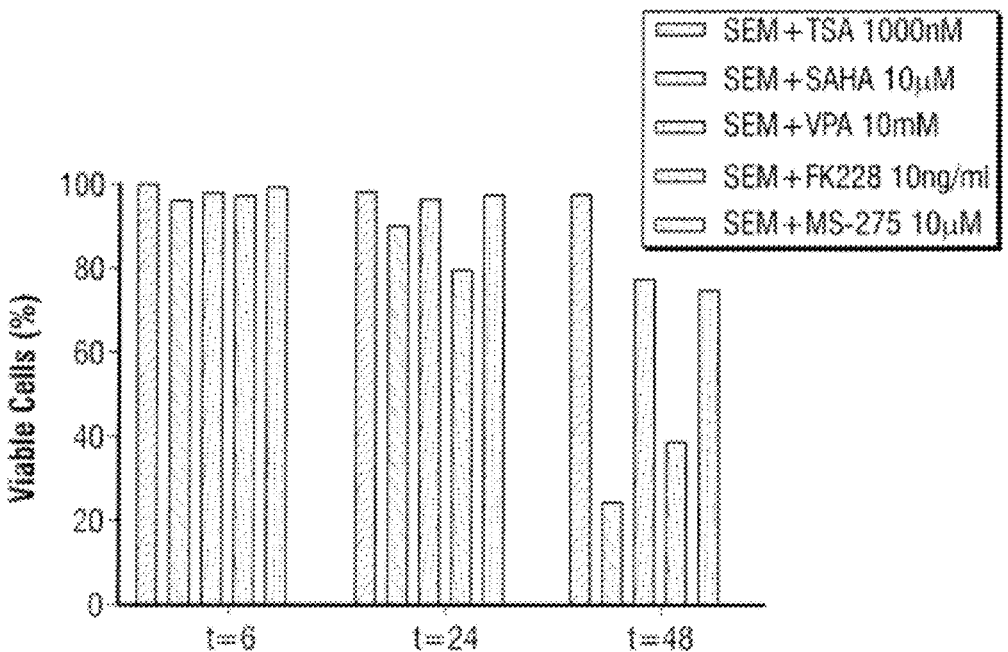
Figure 8A:
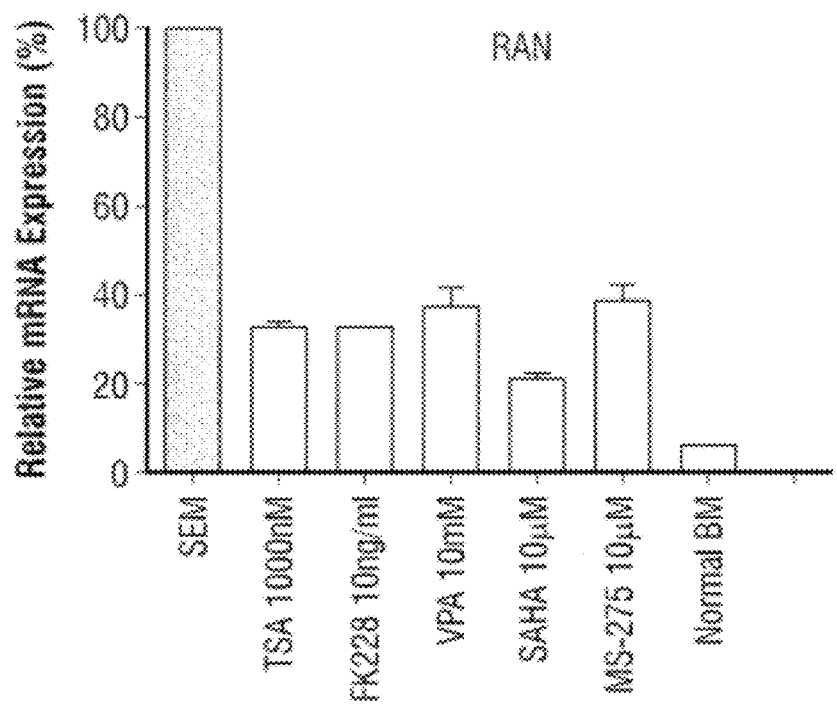
FIGS. 8A, 8B, 8C, 8D, 8E, 8F and 8G show relative proto-oncogene mRNA expression after exposure to HDAC inhibitors in SEM cell line.
Figure 8B:
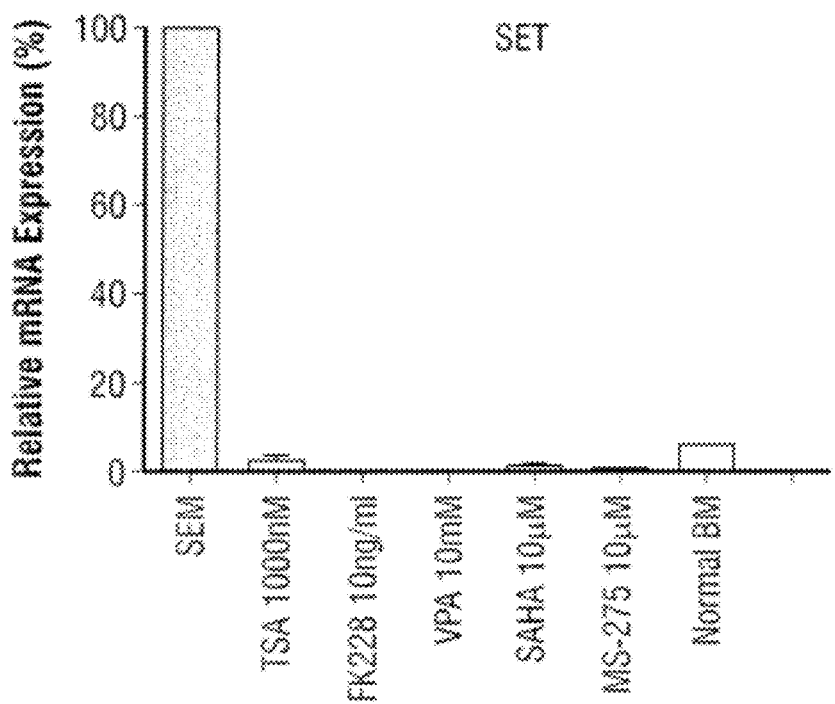
Figure 8C:
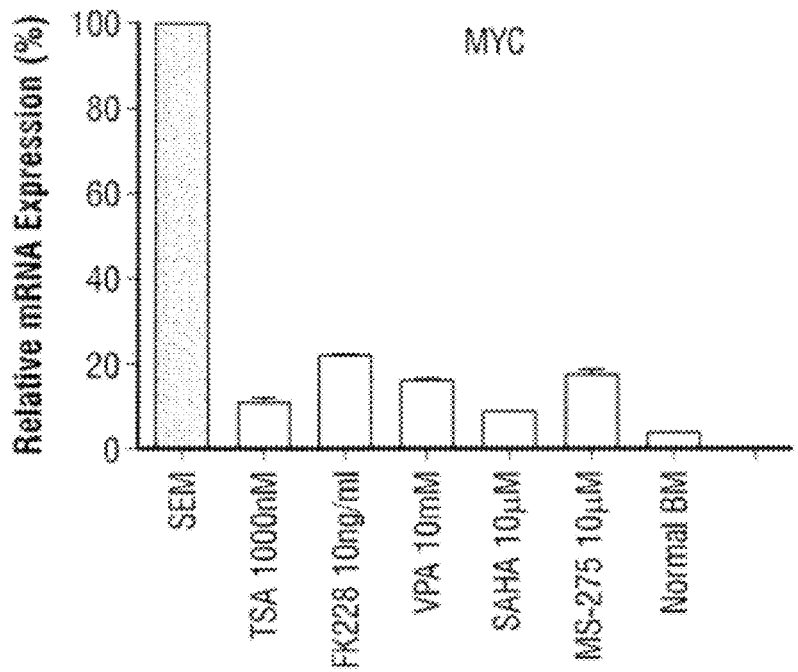
Figure 8D:
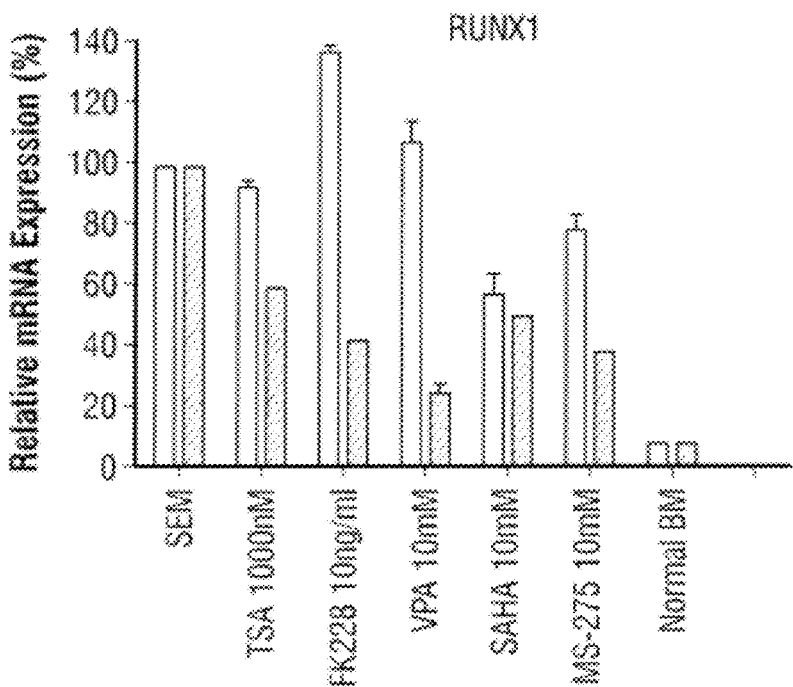
Figure 8E:
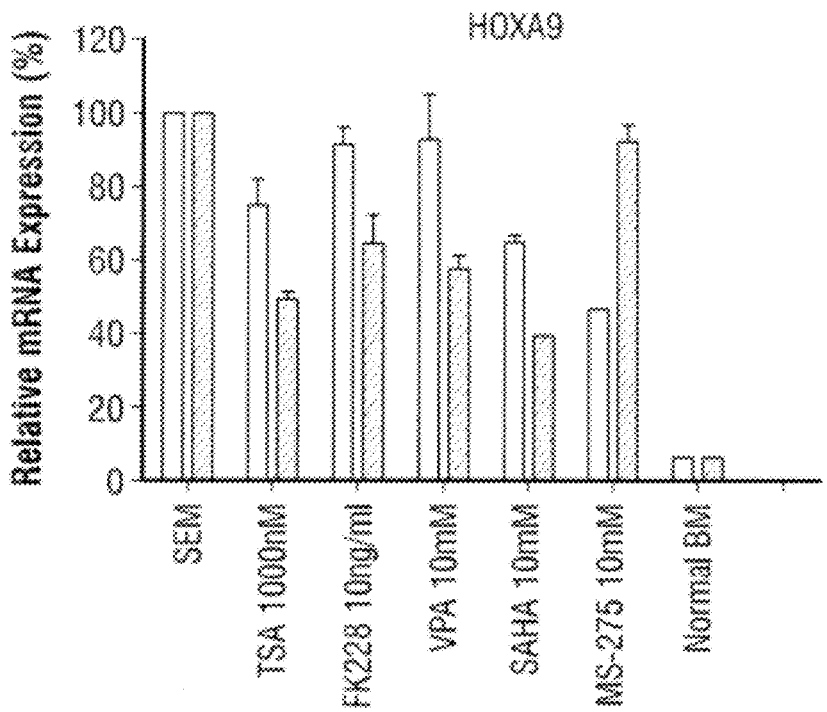
Figure 8F:
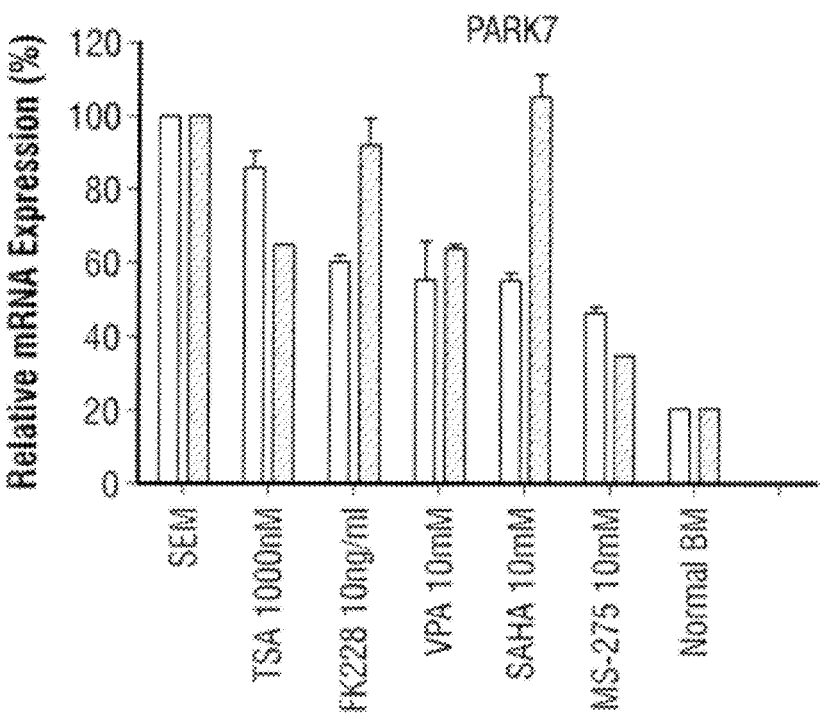
Figure 8G:
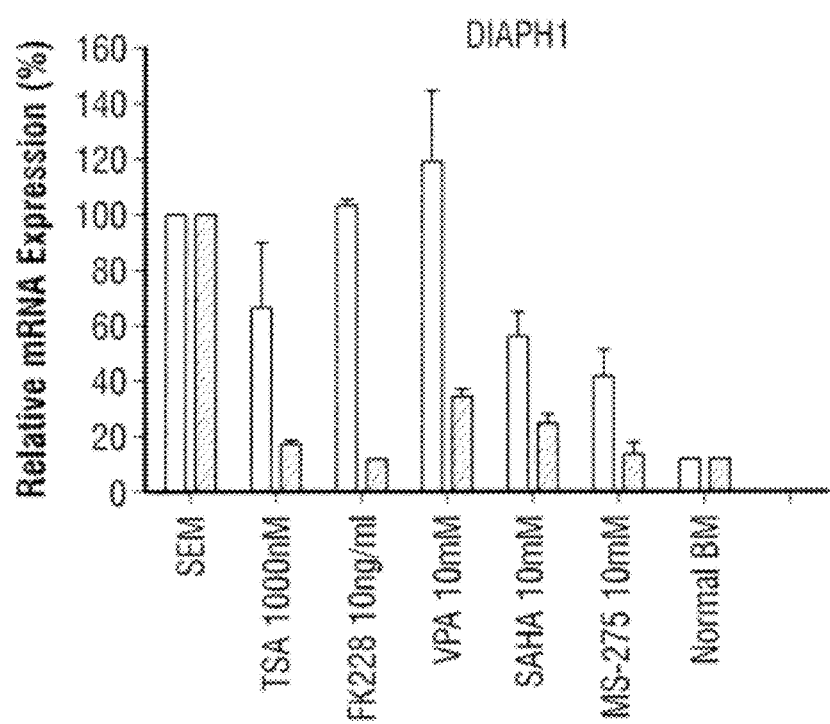
Figure 8A:
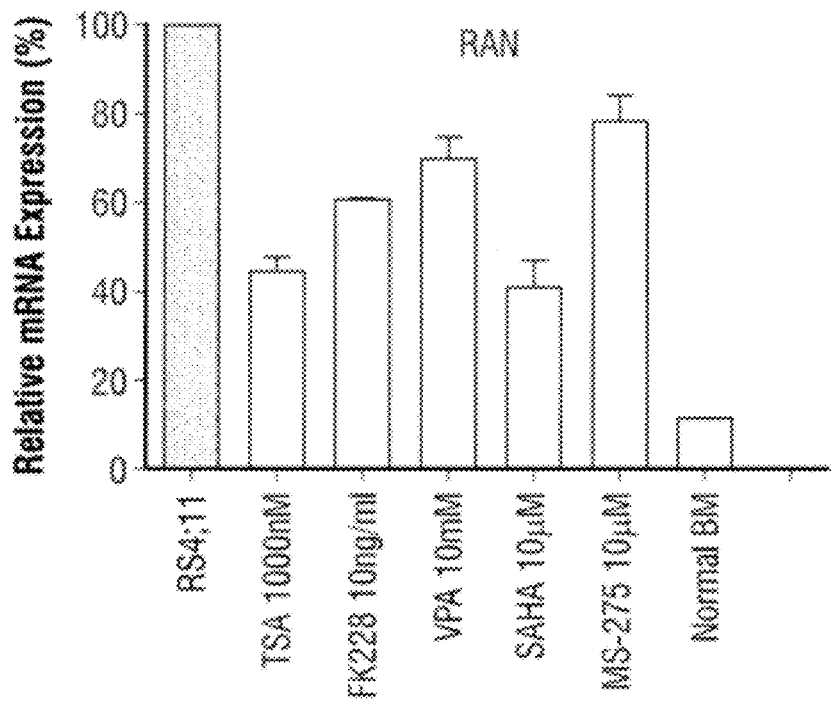
Figure 8B:
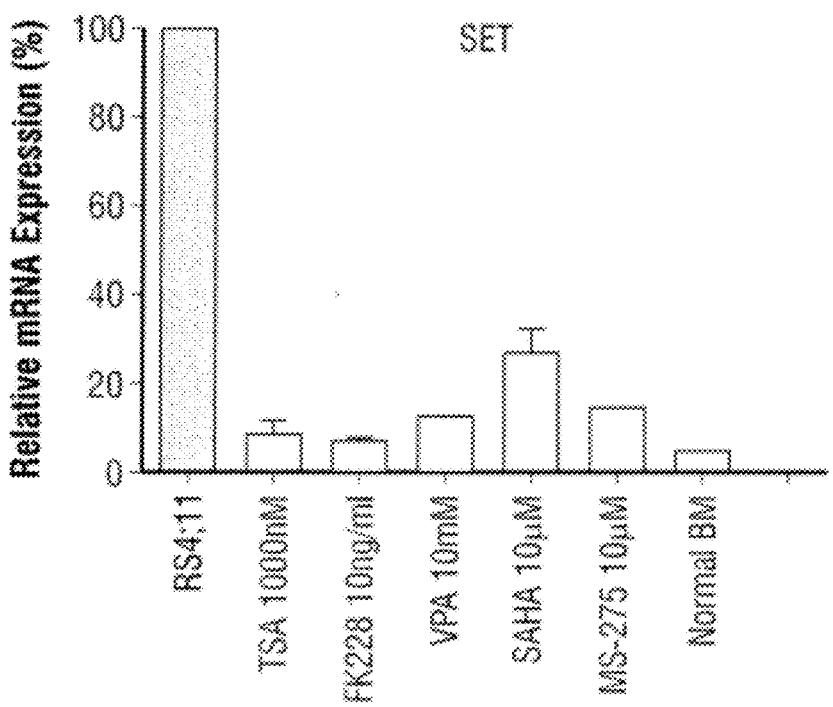
Figure 8C:
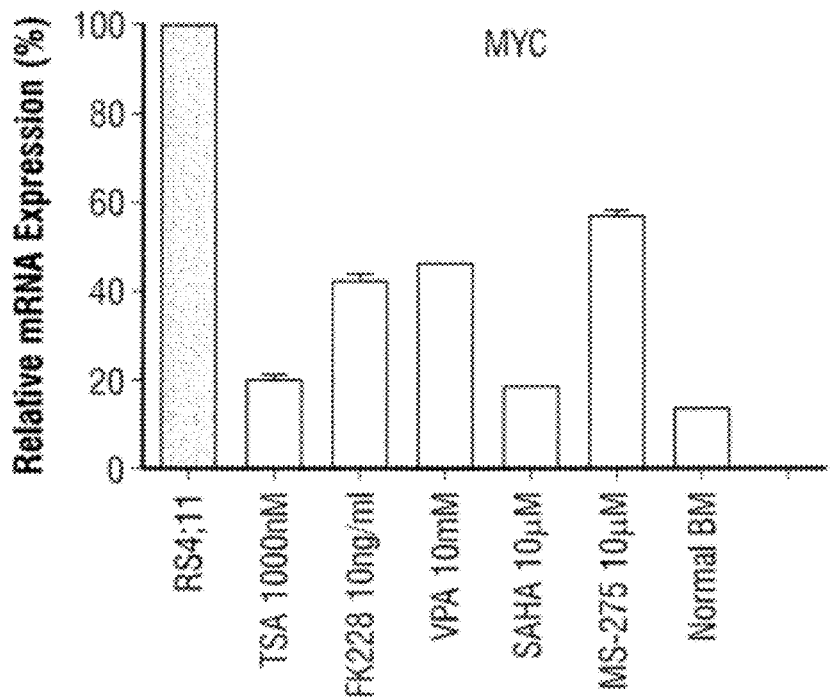
Figure 8D:
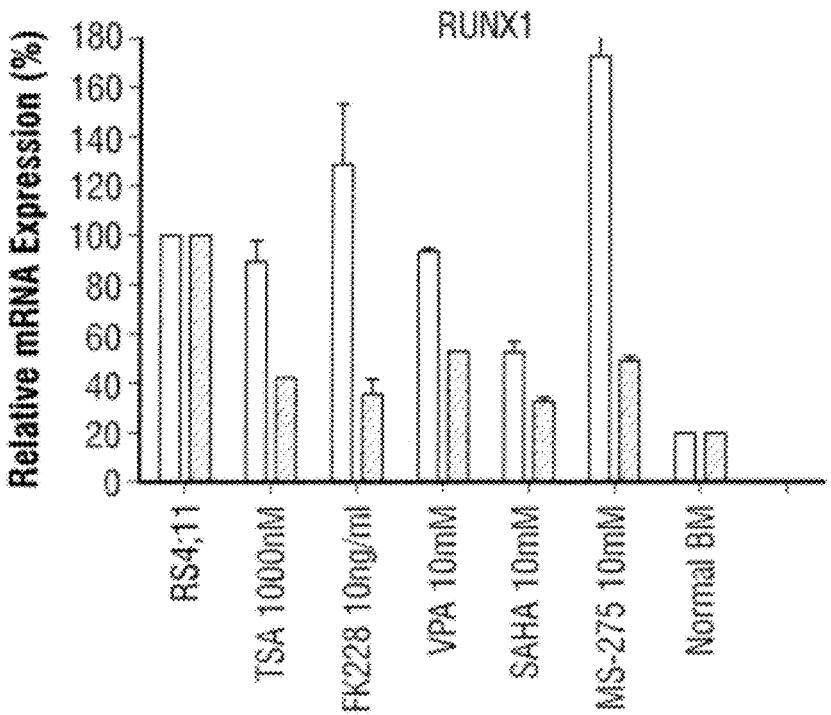
Figure 8E:
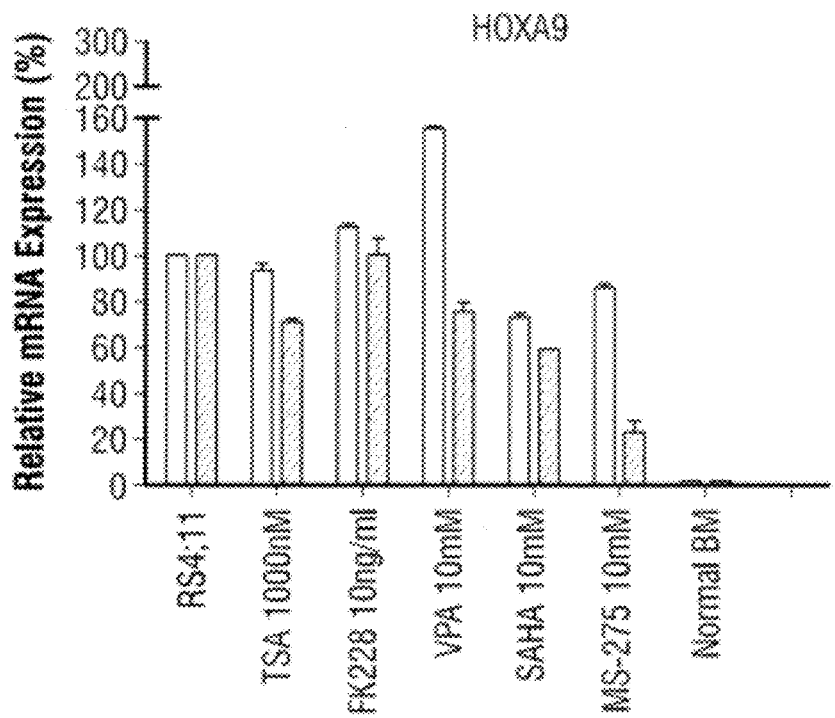
Figure 8F:
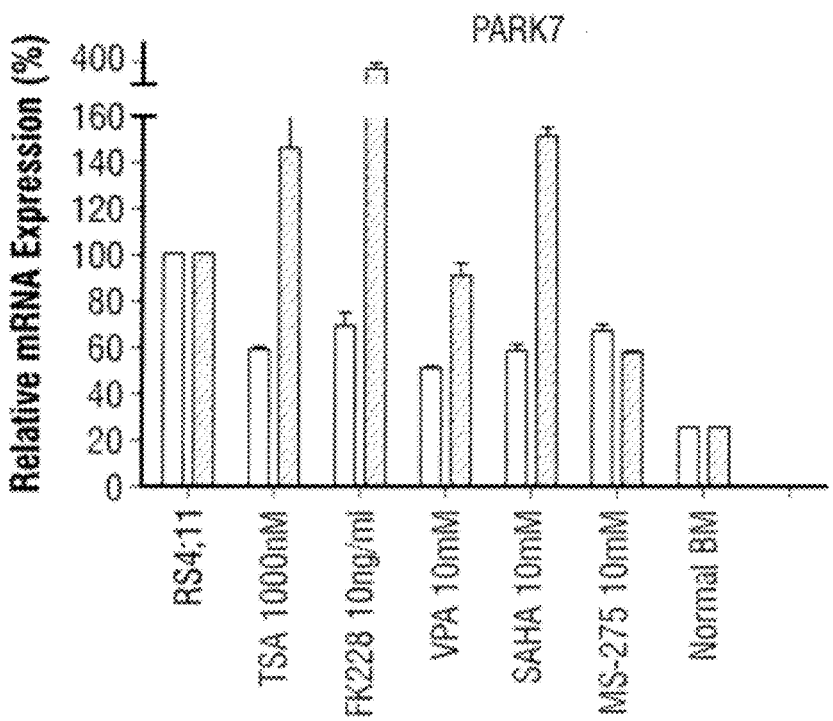
Figure 8G:
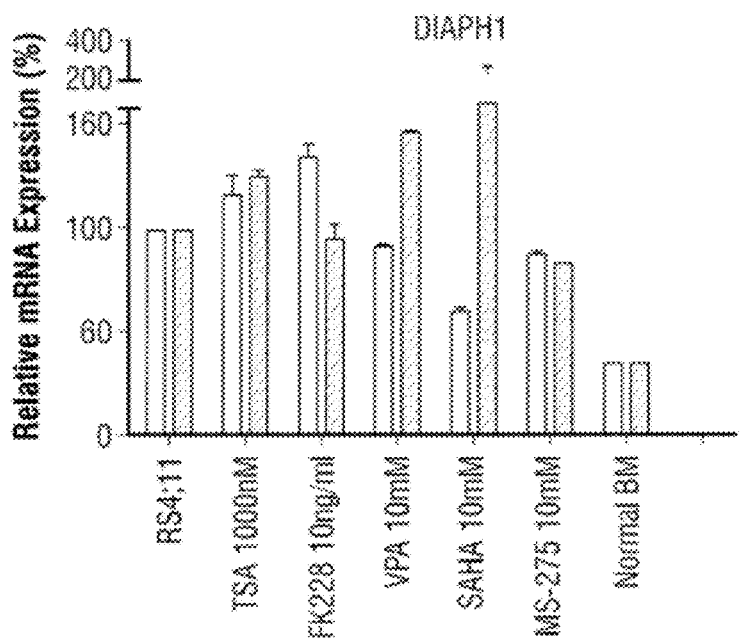

Repression of Activated Proto-Oncogene Expression in MLL-Rearranged ALL Cells by HDAC Inhibitors To explore the mechanism of action of HDAC inhibitors on induced leukemic cell death in MLL-rearranged ALL, the t(4;11)-positive ALL cell lines SEM and RS4;11 were exposed to various concentrations of TSA, SAHA, VPA, MS-275 and romidepsin for 6, 24 or 48 hours. During these exposures, cell viability was monitored by trypan blue exclusion (FIG. 7). Quantitative real-time PCR was used to determine the mRNA expression levels of MYC, SET, RUNXI, RAN, HOXA9, DIAPHI and PARK7 in the cell lines SEM and RS4;11 during exposure to the different HDAC inhibitors. After 6 hours of exposure, at which point no cytotoxicity was observed, several of the genes were notably down-regulated. The expression levels of RAN, SET, and MYC were readily down-regulated to comparable levels displayed by normal bone marrow samples. After 24 hours of exposure RUNXI was substantially down-regulated in both SEM and RS4;11, whereas HOXA9 and PARK7 expression remained largely unaffected or was even increased. DIAPH1 was severely down-regulated by all HDAC inhibitors in SEM but not in RS4;11 cells (FIG. 8). As predicted by cmap analysis, the pan-HDAC inhibitors TSA and SAHA consistently repressed most of the selected proto-oncogenes. The permutation testing was significant for TSA (p=0.00, specificity=0.73), SAHA (p=0.04, specificity=0.71) and MS-275 (p=0.04, specificity=0.19).

Example 9

High Expression of Proto-Oncogenes Reduces Relapse-Free Survival

To investigate the clinical relevance of high-level expression of the selected and aberrantly expressed proto-oncogenes, survival statistics based on the relative expression obtained from quantitative RT-PCR analysis in a larger group of t(4;11)-positive infant ALL patients (n=28) was computed (FIG. 9). The median expression levels were used as cutoff values to divide patients into groups characterized by either high or low proto-oncogene expression. The genes tested were RAN, RUNX1, SET and MYC genes. Elevated expression of each gene separately barely had any influence on the risk of relapse (FIG. 10). However, patients who showed high expression (above the median value from RT-PCR) for 3 or 4 of the proto-oncogenes (n=7) had a significantly increased relapse risk (FIG. 9).

All publications, patents, and patent applications mentioned in this specification are herein incorporated by reference to the same extent as if each individual publication, patent, or patent application was specifically and individually indicated to be incorporated by reference.

The present disclosure has been described above with reference to exemplary embodiments. However, those skilled in the art, having read this disclosure, will recognize that changes and modifications may be made to the exemplary embodiments without departing from the scope of the present disclosure. The changes or modifications are intended to be included within the scope of the present disclosure, as expressed in the following claims.

What is claimed:

1. A method of treating a mixed-lineage leukemia (MLL)-rearranged infant acute lymphoid leukemia (ALL) comprising administering to a patient romidepsin in combination with a DNA demethylating agent selected from the group consisting of 5-azacytidine (azacytidine), 5-azadeoxycytidine (decitabine), zebularine and procaine.

2. The method of claim 1, wherein the dose of romidepsin ranges from about 0.5 mg/m$^2$ to about 28 mg/m$^2$ for intravenous administration.

3. The method of claim 2, wherein the dose of romidepsin ranges from about 8 mg/m$^2$ to about 14 mg/m$^2$.

4. The method of claim 3, comprising infusing the dose of romidepsin to the patient over a 4 hour period.

5. The method of claim 4, comprising infusing the dose of romidepsin to the patient on days 1, 8 and 15 of a cycle.

6. The method of claim 5, comprising repeating the cycle every 28 days.

7. The method of claim 1, wherein the dose of romidepsin ranges from about 1 mg/m$^2$ to about 300 mg/m$^2$ for oral administration.

8. The method of claim 7, wherein the dose of romidepsin ranges from about 25 mg/m$^2$ to about 75 mg/m$^2$.

9. The method of claim 1, wherein the DNA demethylating agent is 5-azacytidine.

10. A method for treating an MLL-rearranged infant ALL comprising administering to an MLL-rearranged infant ALL patient romidepsin in combination with a DNA demethylating agent, comprising intravenously infusing over a 4 hour period the romidepsin in a dose of 14 mg/m$^2$ to the patient on days 1, 8 and 15 of a cycle, wherein the cycle is repeated every 28 days.

11. The method of claim 10, wherein the DNA demethylating agent is 5-azacytidine.

* * * * *